US006379959B1

(12) United States Patent
De Llorens Duran et al.

(10) Patent No.: US 6,379,959 B1
(45) Date of Patent: Apr. 30, 2002

(54) METALOCARBOXYPEPTIDASE INHIBITORS AND DERIVED MOLECULES USED AS ANTITUMOR AGENTS

(75) Inventors: Rafael De Llorens Duran, Banyoles; Carmen Blanco Aparicio, Valencia; Miguel Angel Molina Vila, Girona, all of (ES); Esther Fernandez Salas, Kensington, MD (US); Enrique Querol Murillo, Barcelona; Francesc X. Aviles Puigvert, Cerdanyola, both of (ES); Marsha L. Frazier, Houston, TX (US)

(73) Assignees: Universitat Autonoma de Barcelona, Girona; Universitat de Girona, Barcelona, both of (ES)

(*) Notice: Subject to any disclaimer, the term of this patent is extended or adjusted under 35 U.S.C. 154(b) by 0 days.

(21) Appl. No.: 09/269,126

(22) PCT Filed: Sep. 19, 1997

(86) PCT No.: PCT/ES97/00232

§ 371 Date: Sep. 27, 1999

§ 102(e) Date: Sep. 27, 1999

(87) PCT Pub. No.: WO98/12317

PCT Pub. Date: Mar. 26, 1998

(30) Foreign Application Priority Data

Sep. 20, 1996 (ES) .............................................. 9601986

(51) Int. Cl.$^7$ ........................ A61K 38/04; A61K 38/16; A61K 38/56; C07K 5/10; C07K 14/415
(52) U.S. Cl. ............................. 435/375; 514/2; 514/12; 530/324; 530/330
(58) Field of Search ................................ 435/212, 69.2, 435/375; 424/94.63, 94.67; 514/2, 12; 530/330, 324

(56) References Cited

U.S. PATENT DOCUMENTS 4,906,457 A  3/1990  Ryan ............................ 424/59

OTHER PUBLICATIONS

Querol et al "Innovations in Proteases and their inhibitors" 1993, Walter de Gruyter & Co., pp. 478–493.
Stewart Bates, et al., "p53 in signaling checkpoint arrest or apoptosis", Current Opinion in Genetics & Development, 1996, pp. 12–18.
Mariana Resnicoff, et al., "The Insulin–like Growth Factor I Receptor Protects Tumor Cells from Apoptosis in Vivo", Cancer Research 55, 1995, pp. 2463–2469.
Renato Baserga, "Controlling IGF–receptor function: a possible strategy for tumor therapy", TIBTECH May 1996, (vol. 14), pp. 150–152.
Renato Baserga, "The Insulin–like Growth Factor I Receptor: A Key to Tumor Growth?", Cancer Research 55, 1995, pp. 249–252.

Alexander Levitzki, "Targeting signal transduction for disease therapy", Current Opinion in Cell Biology, 1996, vol. 8, pp. 239–244.
Helmout Modjtahedi, et al., "The Binding of HB–EGF to Tumour Cells is blocked by MABS whick act as EGF and TGFα Antagonists", Biochemical and Biophysical Research Communications, vol. 207, No. 1, 1995, pp. 389–397.
Miquel Juncosa–Ginestà, et al., "Improved Efficiency in Site–Directed Mutagenesis by PCR Using a Pyrococcus sp. GB–D Polymerase", Benchmarks, vol. 16, No. 5 (1994), 2 pages.
J. Sambrook, et al., "Molecular Cloning—A Laboratory Manual, Second Edition", Cold Spring Harbor Laboratory Press, 1989, pp. xi–xxxviii.
M.L. Frazier, et al., "Establishment of a New Human Pancreatic Adenocarcinoma Cell Line, MDAPPanc'", Pancreas, 1990 Raven Press, Ltdl., vol. 5, No. 1, pp. 8–16.
Ester Fernández, M.S., et al., "Expression of Acinar and Ductal Products in Capan–1 Cells Growing in Synthetic Serum and Serum–free Media", Cancer, 1994, vol. 73, No. 9, pp. 2285–2295.
Robert F. Santerre, et al., "Insulin synsthesis in a clonal cell line of simian virus 40–transformed hamster pancreatic beta cells", Proc. Natl. Acad. Sci. USA, 1981, Cell Biology, vol. 78, No. 7, pp. 4339–4343.
Jørgen Fogh, et al., "Absence of HeLa Cell Contamination in 169 Cell Lines Derived from Human Tumors", J. Natl. Cancer Inst., 1977, vol. 58, No. 2, pp. 209–214.
Jørgen Fogh, et al., "One Hundred and Twenty–Seven Cultured Human Tumor Cell Lines Producing Tumors in Nude Mice", J. Natl. Cancer Inst., 1977, vol. 59, No. 1, pp. 221–226.
Michael Lieber, et al., "Establishment of a Continuous Tumor–Cell Line (Panc–1) from a Human Carcinoma of the Exocrine Pancreas", Int. J. Cancer, 1975, vol. 15, pp. 741–747.
E. Barberá, et al., "Noncorrelation between implantation and Growth of Tumor Cells for Their Final Metastatic Efficiency", Invasion Metastasis, 1988, vol. 8, pp. 266–284.
William C. Earnshaw, "Nuclear Changes in apoptosis", Current Opinion in Cell Biology, 1995, vol. 7, pp. 337–343.
Markus M. Borner, et al, "Drug–induced Apoptosis is not Necessarily Dependent on Macromolecular Synthesis or Proliferation in the p53–negative Human Prostate Cancer Cell Line PC–3", Cancer Research 55, 1995, pp. 2122–2128.

(List continued on next page.)

Primary Examiner—Elizabeth Slobodyansky
(74) Attorney, Agent, or Firm—Steinberg & Raskin, P.C.

(57) ABSTRACT

The present invention relates to metalocarboxypeptidase inhibitors and to their natural protein variants or protein variants redesigned by engineering, as well as to peptidomimetic molecules derived from the above and used as antitumor agents.

13 Claims, 31 Drawing Sheets

OTHER PUBLICATIONS

J. Bravo, et al., "A Versatile Negative–Staining Ribonuclease Zymogram", Analytical Biochemistry, vol. 219, 1994, pp. 82–86.

Marion M. Bradford, "A Rapid and Sensitive Method for the Quantitation of Microgram Quantities of Protein Utilizing the Principle of Protein–Dye Binding", Analytical Biochemistry, vol. 72, 1976, pp. 248–254.

Michael G. Ormerod, et al., "Cell Cycle Analysis of Asynchronous Cell Populations by Flow Cytometry Using Bromodeoxyuridine Label and Hoechst–Propidium Iodide Stain", Cytometry, vol. 13, 1992, pp. 678–685.

Z. Darzynkiewicz, et al., "Features of Apoptotic Cells Measured by Flow Cytometry", Cytometry, vol. 13, 1992, pp. 795–808.

Detlef Güssow, et al., "The Human $\beta_2$–Microglobulin Gene Primary Structure and Definition of the Transcriptional Unit", The Journal of Immunology, 1987, vol. 139, pp. 3132–3138.

Ed Harlow, et al., "Molecular Cloning and In Vitro Expression of cDNA Clone for Human Cellular Tumor Antigen p53", Molecular and Cellular Biology, 1985, vol. 5, pp. 1601–1610.

Raymond J. MacDonald, et al., "Rat Pancreatic Ribonuclease Messenger RNA", The Journal of Biological Chemistry, vol. 257, 1982, pp. 14582–14585.

Piotr Chomczynski, et al., "Single–Step Method of RNA Isolation by Acid Guanidinium Thiocyanate–Phenol–Chloroform Extraction", Analytical Biochemistry, vol. 162, 1987, pp. 156–159.

Marsha L. Frazier, et al., "Insulin Gene Expression during Development of the Fetal Bovine Pancreas", Biochemistry, vol. 20, 1981, pp. 367–371.

Andrew P. Feinberg, et al., "A Technique for Radiolabeling DNA Restriction Endonuclease Fragments to High Specific Activity", Analytical Biochemistry, vol. 132, 1983, pp. 6–13.

C.M. Barton, et al., "Abnormalities of the p53 tumour suppressor gene in human pancreatic cancer", Cancer, vol. 64, pp. 1076–1082.

Sheldon Rowan, et al., "Specific loss of apoptotic but not cell–cycle arrest function in a human tumor derived p53 mutant", The EMBO Journal, vol. 15, No. 4, pp. 827–838, 1996.

Michael Reiss, et al., "Activation of the Autocrine Transforming Growth Factor α Pathway in Human Squamous Carcinoma Cells", Cancer Research, vol. 51, 1991, pp. 6254–6262.

Hidenobu Kamohara, et al., "Neutrophil Elastase Inhibitor (Ono–5046.Na) Suppresses the Proliferation, Motility and Chemotaxis of a Pancreatic Carcinoma Cell Line, CAPAN–1", Research Communications in Molecular Pathology and Pharmaology, vol. 98, No. 1, 1997.

Palmer Taylor et al., "Molecular Basis of Pharmacologic Selectivity", Principles of Drug Action, $3^{rd}$ Edition, Churchill Livingstone Inc., 1990, pp. 1–31.

Leo C. Groenen, et al., "Structure–Function Relationships for the EGF/TGF–α Family of Mitogens", Growth Factors, 1994, vol. 11, pp. 235–257.

Nicholas J. Donato, etal., "Early Events in the Antiproliferative Action of Tumor Necrosis Factor Are Similar to the Early Events in Epidermal Growth Factor Growth Stimulation", Journal of Cellular Biochemistry, vol. 41, 1989, pp. 139–157.

U.K. Laemmli, et al., "Cleavage of Structural Proteins during the Assembly of the Head of Bacteriophage T4", Nature, vol. 227, 1970, pp. 680–685.

J.M. Mas, et al., "Protein Similarities Beyond Disulphide Bridge Topology", J. Mol. Biol., (1998), vol. 284, pp. 541–548.

Carmen Blanco–Aparicio, et al., "Potato Carboxypeptidase Inhibitor, a T–knot Protein, is an Epidermal Growth Factor Antagonist that Inhibits Tumor Cell Growth", The Journal of Biological Chemistry, vol. 273, No. 20, 1998, pp. 12370–12377.

Henning Birkedal–Hansen, "Proteolytic remodeling of extracellular matrix", Current Opinion in Cell Biology, 1995, vol. 7, pp. 728–735.

Jeffrey S. Flier, et al., "Clinical Applications of Research on Angiogenesis", Seminars in Medicine of the Beth Israel Hospital, vol. 333, 1995, pp. 1757–1763.

Paolo Mignatti, et al., "Biology and Biochemistry of Proteinases in Tumor Invasion", 1993, Proteinsases in Tumor Invasion, pp. 161–195.

Richard O. Hynes, "The Impact of Molecular Biology on Models for Cell Adhesion", BioEssays, vol. 16, No. 9, 1994, pp. 663–669, Paul C. Billings, et al., "Inhibition of radiation–induced transformation of C3H/10T1/2 cells by carboxypeptidase inhibitor 1 and inhibitor II from potatoes", Carcinogenesis, vol. 10, No. 4, 1989, pp. 687–691.

Elise C. Kohn, et al., "Molecular Insights into Cancer Invasion: Strategies for Prevention and Intervention", Cancer Research, (1995), vol. 55, pp. 1856–1862.

Paul C. Billings, et al., "The interaction of the potatoe–derived chymotrypsin inhibitor with C3H/10T1/2 cells", Carcinogenesis, vol. 12, (1991), pp. 653–657.

Paul C. Billings, et al., "A growth–regulated protease activity that is inhibited by the anticarcinogenic Bowman–Birk protease inhibitor", Proc. Natl. Acad. Sci. USA, vol. 89, (1992), pp. 3120–3124.

Ann. R. Kennedy, et al., "Suppression of Carcinogenesis in the Intestines of Min Mice by teh Soybean–derived Bowman–Birk Inhibitor", Cancer Research, vol. 56, (1996), pp. 679–682.

Stuart A. Aaronson, "Growth Factors and Cancer", Science, vol. 254, (1988), pp. 1148–1152.

Renato Baserga, "Oncogenes and the Strategy of Growth Factors", Cell, vol. 79, (1994), pp. 927–930.

Craig B. Thompson, "Apoptosis in the Pathogenesis and Treatment of Disease", Science, vol. 267, (1995), pp. 1456–1462.

Sharad Kumar, et al., "Role of multiple cellular proteases in the execution of programmed cell death", FEBS Letters, vol. 375, (1995), pp. 169–173.

Atsushi Takahashi, et al., "ICE–related proteases in apoptosis", pp. 50–55.

Tushar Patel, et al., "The role of proteases during apoptosis", The FASEB Journal, vol. 10, (1996), pp. 587–597.

G. Michael Hass, et al., "Carboxypeptidase Inhibitor from Potatoes", Methods in Enzymology, vol. 80 (1981), pp. 778–791.

Peter D. Sun, "The Cystine–Knot Growth–Factor Superfamily", Annu. Rev. Biophys. Biomol. Struct., vol. 24 (1995), pp. 269–291.

Georgina Berrozpe, et al., "Comparative Analysis of Mutations in the p53 and K–ras Genes in Pancreatic Cancer", Int. J. Cancer, vol. 58, (1994), pp. 185–191.

Erkki Koivunen, et al., "Tumor–associated Trypsin Participates in Cancer Cell–mediated Degradation of Extracellular Matrix", Cancer Research, vol. 51, (1991), pp. 2107–2112.

Paul C. Billings, et al., "Internalisation of the Bowman–Birk Protease Inhibitor by Intestinal Epithelial Cells", Int. J. Cancer, vol. 27, (1991), pp. 903–907.

Wen–Tien Chen, "Membrane proteases: roles in tissue remodeling and tumour invasion", Current Opinion in Cell Biology, vol. 4, (1992), pp. 802–809.

Lance A. Liotta, et al., "Cancer Metastasis and Angiogenesis: An Imbalance of Positive and Negative Regulation", Cell, vol. 64, (1991), pp. 327–336.

B. Oliva, et al., "Stability and Fluctuations of the Potato Carboxypeptidase A Protein Inhibitor Fold: A Molecular Dynamics Study", Biochemical and Biophysical Research Communications, vol. 176, (1991), pp. 616–621.

Miguel A. Molina, et al., "Expression of a synthetic gene encoding potato carboxypeptidase inhibitor using a bacterial secretion vector", Gene, vol. 116, (1992), pp. 129–138.

O. Tapia, et al., "Molecular Dynamics as a Tool to Help Design Mutants", Molecular Engineering, vol. 1 (1991), pp. 249–266.

B. Oliva, et al., "A Molecular Dynamics Study of a Model Built Pro–36–Gly Mutant Derived from the Potato Carboxypeptidase A Inhibitor Protein", Biochemical and Biophysical Research Communications, vol. 176, (1991), pp. 627–632.

Miguel A. Molina, et al., "C–tail Valine Is A Key Residue for Stabilization of Co mplex between Potato Inhibitor and Carboxypeptidase A*", The Journal of Biological Chemistry, vol. 269, (1994), pp. 21467–21472.

C. Marino–Buslje, et al., "Overproduction of a recombinant carboxypeptidase inhibitor by optimization of fermentation conditions", Appl. Microbiol Biotechnol, vol. 41, (1994), pp. 632–637.

Jui–Yoa Chang, et al., "The Disulfide Folding Pathway of Potato Carboxypeptidase Inhibitor*", The Journal of Biological Chemistry, vol. 269, (1994), pp. 22087–22094.

B. Oliva, et al., "Structure and atomic fluctuation patterns of potato carboxypeptidase a inhibitor protein", Eur. Biophys. J., vol. 24, (1995), pp. 1–11.

Baldomero Oliva, et al., "On the Entropic and Hydrophobic Properties Involved in the Inhibitory Mechanism of Carboxypeptidase A by its Natural Inhibitor from Potato", J. Mol. Model, vol. 1, (1995), pp. 54–67.

Neil W. Isaacs, "Cystine knots", Current Opinion in Structural Biology, vol. 5, (1995), pp. 391–395.

Shuo Liang Lin, et al., "A disulphide–reinforced structural scaffold shared by small proteins with diverse functions", Nature Structural Biology, vol. 2, (1995), pp. 835–837.

Ann R. Kennedy, "Prevention of Carcinogenesis by Protease Inhibitors", University of Pennsylvania, Dept. of Radiation Oncology, (1993), pp. 1999–2005.

Walter Troll, et al., "Protease Inhibitors as Cancer Chemopreventive Agents", Plenum Press, (1993), pp. xi–xviii.

Francesc X. Avilés, "Innovations in Proteases and their Inhibitors", Universitat Autònoma de Barcelona, (1993), Table of Contents, 5 pages.

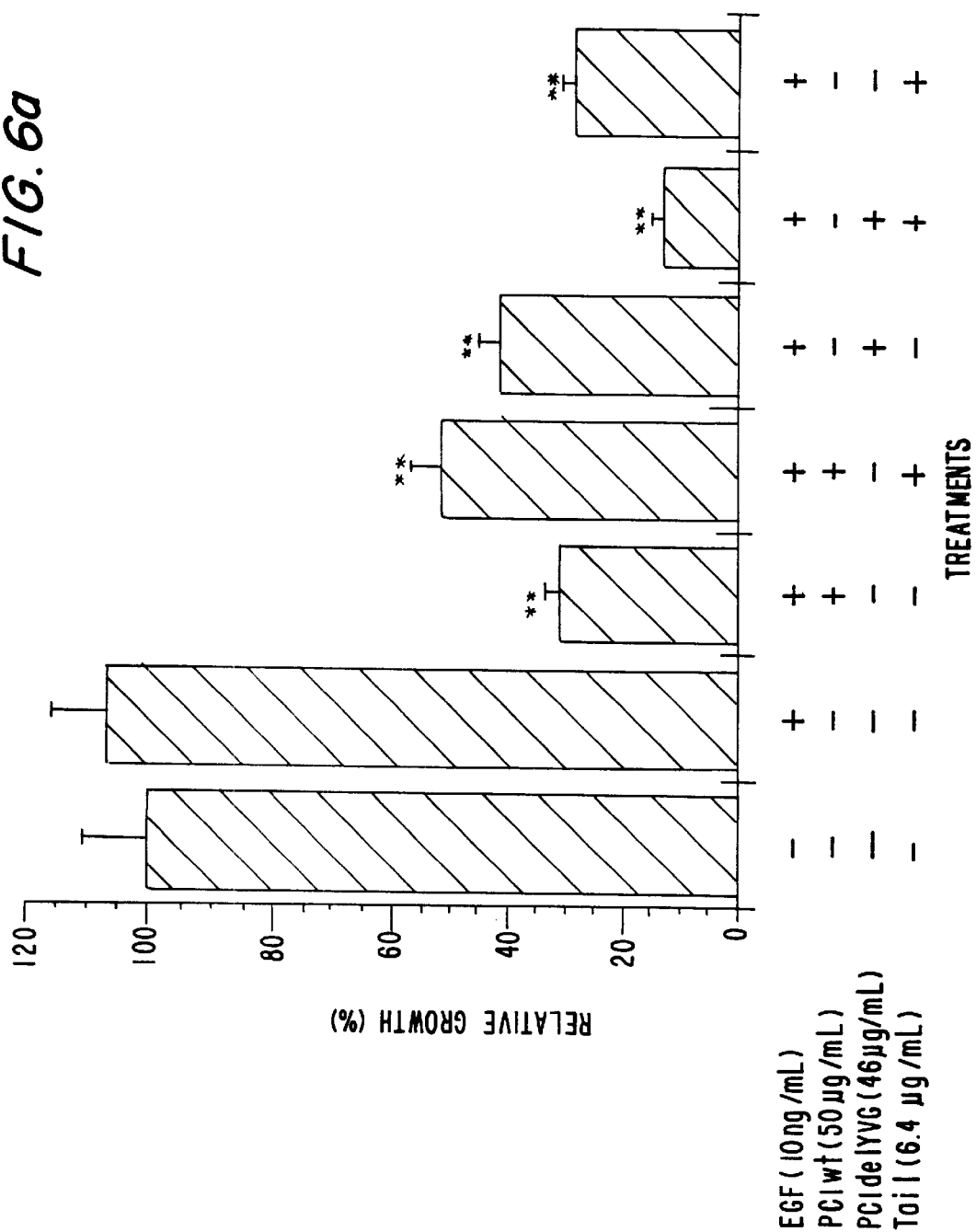

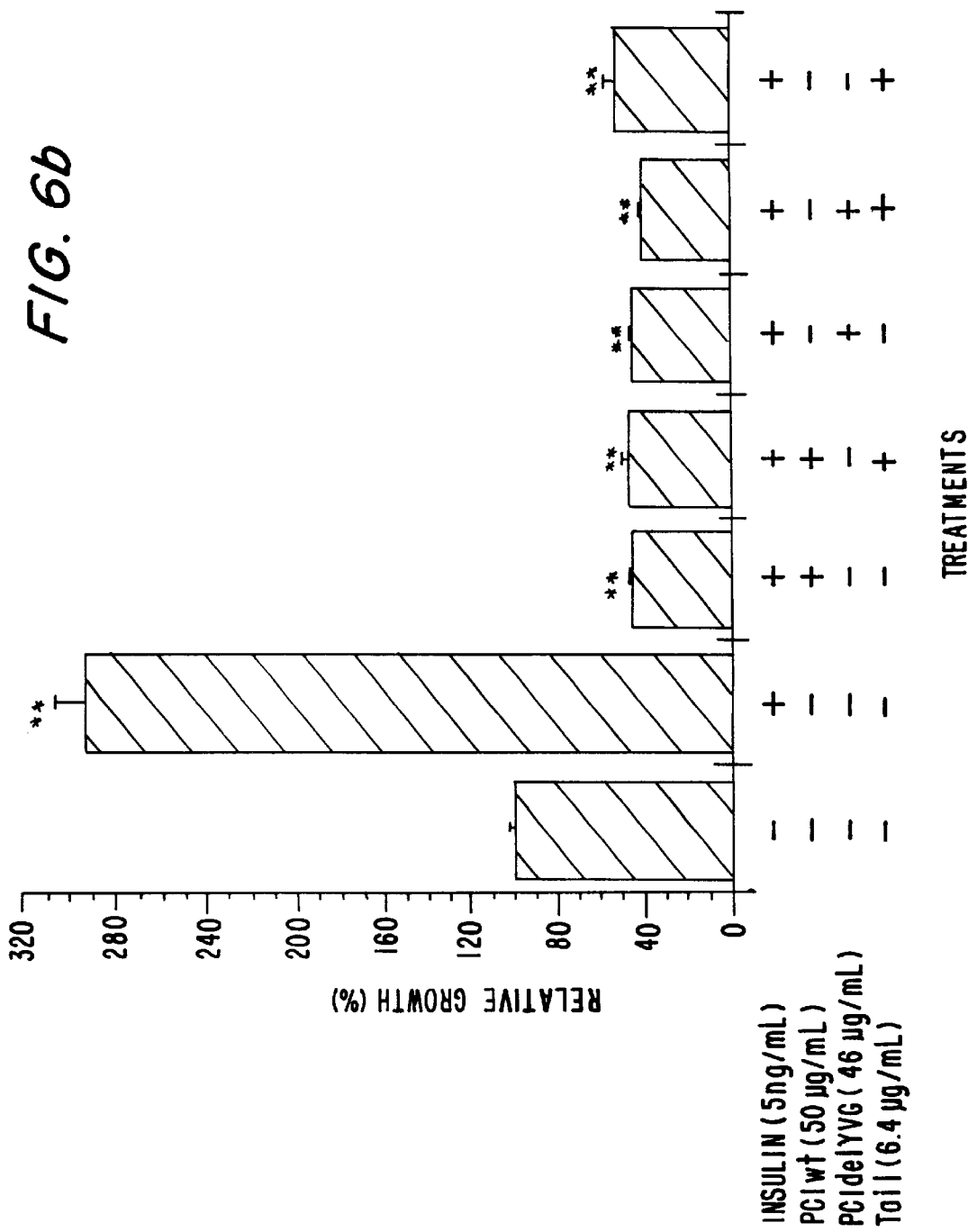

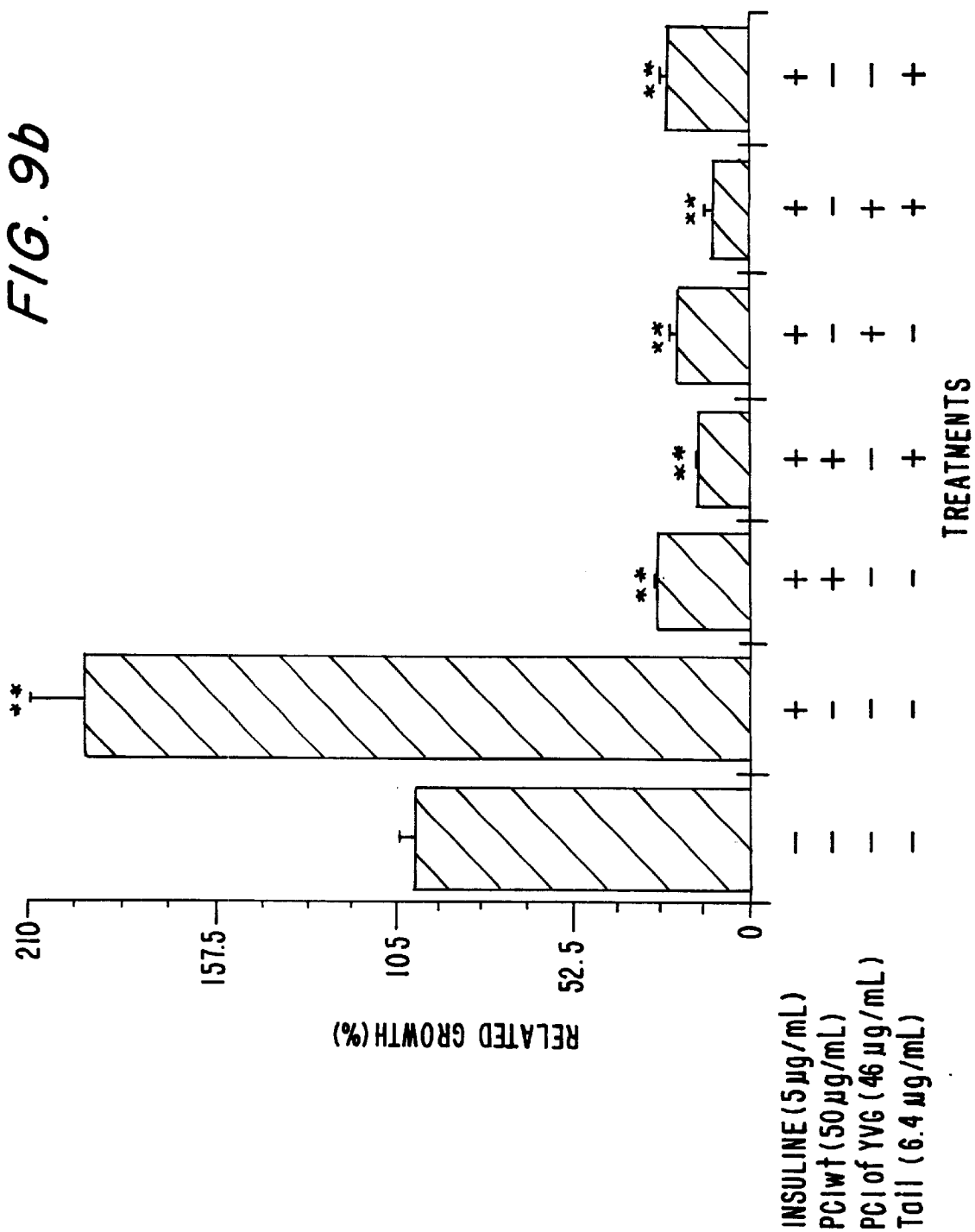

METALOCARBOXYPEPTIDASE INHIBITORS AND DERIVED MOLECULES USED AS ANTITUMOR AGENTS

FIELD OF THE INVENTION

The present invention, in general, refers to the use of carboxypeptidase protein inhibitors and of their natural variants or of forms redesigned by protein engineering as well as peptidomimetic molecules derived from the former as an anticancerous medicament, and more specifically, to control the invasion and the metastatic growth in tumors and to its use for therapeutic purposes.

1. BACKGROUND OF THE INVENTION

Protease inhibitors have been extensively related to processes of biomedical interest, such as the processing of hormone and neuropeptide precursors, inflammatory processes, tumoral processes, etc. (Avilés, F. X., editor of "Innovations in proteases and their inhibitors", Walter de Gruyter, 1993; Trow, W. & Kennedy, A. R. eds. "Protease inhibitors as cancer chemopreventive agents"; Plenum Publishing Corp., 1993; Kennedy, A. R. (1994) *Cancer Res.*, 54: 1995s–2005s). Among the protease inhibitors are the metalocarboxypeptidase inhibitors. One of them, the inhibitor from potato (from now on, referred to as "PCI") has been extensively studied, from the structural and functional point of view, as an inhibitor by our research team (Molina, M. A. et al. (1992) *Gene*, 116: 129–138; Oliva, B. et al. (1991) *Biochem. Biophys. Res. Comm.*, 176: 616–621 and 627–632; Tapia et al. (1991) *J. Mol. Engineer.*, 1: 249–266; Querol, E. et al. (1993) in "Innovations in Proteases and their Inhibitors" (F. X. Avilés, ed.): 447–494. Walter de Gruyter, Berlin, 1993; Molina M. A. et al. (1994) *J. Biol. Chem.*, 269: 22087–22094; Marino-Busjle, C. et al. (1994) *Applied Microb. & Biotech.*, 41: 632–637; Oliva, B. et al. (1995) *J. Mol. Model.*, 5:1–15).

A relevant structural feature of the PCI is that it is a small protein which contains a globular core stabilized by means of three disulfide bridges which constitute a cystine knot. We are referring to a topological pattern shared by other proteins, whether functionally related or not, which employ various cysteines concentrated in a central zone in order to create a stabilizing knot of disulfide bridges. This ensemble of proteins constitutes the so called group of knotins, because of the topological knot they form. We have to underline that, among the proteins which share this structural pattern with PCI, there are various cellular growth factors such as, for instance, the a and β-TGF, NGF, PDGF, EGF and those of the insulin family (Isaacs, N. (1995) *Curr. Opin. Struct. Biol.*, 5:391–395; Lin, S et al. (1995) *Nature Struct. Biol.*, 2, 835–837; Sun P. & Davies, D. (1995) *Ann. Rev. Biphys. Biolmol. Struct.*, 24: 269–291). In the specific case of the PCI, the globular core contains 27 amino acid residues and is flanked by two tails of 7 residues (the N-terminal tail) and of 5 residues (the C-terminal tail). The disulfide bridges are between cysteines 8–24, 12–27 and 18–34. This is the most frequent natural form, the so called IIa form, although there are other isoforms (Hass, G. M. & Ryan, C. A. (1981) *Meth. Enzymol.*, 80: 778–791).

A great number of studies have described the expression of proteases and peptidases in different types of tumoral cells (Chen, W. T. (1992) *Curr. Opin. Cell. Biol.*, 4: 802–809; Birkedal-Hansen, H. (1995) *Curr. Opin. Cell. Biol.*, 7: 728–735). Some of these proteases are related to the processing of peptidic hormones, growth factors, etc. For instance, the existence of proteases responsible for the mobilization of the βFGF (basic fibroblast growth factor) of the extracellular matrix, a factor which has been involved in tumoral angiogenesis (Liotta, L. A. et al. (1991) *Cell*, 327–336. Folkman, J. (1995) *New England J. Med.*, 333: 1757–1763). At the same time, the TGF-β1 factor is also mobilized. It shows opposite effects, thus regulating the angiogenesis process (Mignati, P. & Rifkin, D. B., (1993) *Physiolog. Rev.*, 73: 161–195). The process which has been more intensively studied is the role played by the proteases in invasiveness and metastasis. A feature of the invasive processes, either those which take place in the primary tumor or those related to the establishment of metastasis, is the degradation of the extracellular matrix as a result of which the tumoral cells can penetrate the adjacent tissues (the main components of the extracellular matrix are proteins and proteoglycans) (Hynes, R. O. (1994) *Bioessays*, 16:663–669). In fact, there is a positive relationship between the level of expression of proteases and the aggressivity and malignancy of the tumor due to the greater invasiveness of the tissues of the tumoral cell. These proteases are not specific to the tumoral cells but are also produced by normal cells during the normal recomposition processes of the tissue (wound healing, morphogenesis, etc). The difference is that the tumoral cells links this proteolysis with the motility resulting in an invasion in times and sites which are inappropriate.

Due to the important role which is played by proteases in the tumoral processes and in practically all their stages (concretely, in transformation, invasiveness, adherence and metastasis), various studies have been published in which the possible role of the protease inhibitors as antitumoral agents is analysed (Troll, W. & Kennedy, A. R., editors "Protease inhibitors as cancer chemopreventive agents", 1993). Protease inhibitors would employ their antitumoral properties at various levels among which we may mention:

1. Blocking the transformation of normal cells in tumoral cells, a process in which proteases seem to be involved (Billings, P. C., et al. (1989) *Carcinogenesis*, 10: 687–691).
2. Blocking the proteolytic cascade involved in the process of invasiveness and metastasis (Kohn, E. C. & Liotta, L. A. (1995) *Cancer Res.*, 55: 1856–1862).
3. Altering the processing of growth factors required for the development of the tumor.

Among the relevant studies in relation to the present invention are the following: Billings, P. C. et al. (1989) *Carcinogenesis*, 10: 687–691, where it is described that the addition of PCI in low concentrations (5 µg/mL) inhibits in vitro the tumoral transformation induced by irradiation in embryonic cells of mice. However, up to now, any effect of the PCI in the growth and survival of already transformed cells or in tumoral cells, such as it is described in the present invention, cannot be found in scientific literature. On the other hand, Billings, P. C., et al. (1991) *Carcinogenesis*, 12: 653–657, explain that the chemotrypsin inhibitor 1 of the potato suppresses the transformation provoked by the irradiation in CH3/10T1/2 cells, in vitro. Billings, P. C. et al. (1991) *Eur. J. Cancer*, 27: 903–908, describe another inhibitor derived from soya, the so called Bowman-Birk (from now on, referred to as "BBI") which, in mice, reduces cancer of the colon induced by dimethylhydrazine and in (1992) *Proc. Natl. Acad. Sci. USA*, 889: 3120–3124, characterizes the enzyme target of the BBI as a gelatinase. It has also been described that BBI suppresses carcinogenesis in the intestines (Kennedy, A. R. et al. (1996) *Cancer Res.*, 56: 679–682).

Another relevant aspect for the present invention is the role that growth factors play in the tumoral process. The normal cells are dependent on various growth factors to complete their cellular cycle or to get out of phase $G_0$ (quiescence). In tumoral cells, the system of signal transduction of any of these factors is often found to be altered. For instance, the tumoral cell may present an autocrine loop, or an altered receptor which would be active even in the absence of the growth factor. However, tumoral cells always need some growth factor (IGF-I type) for their proliferation and for the development of the tumor so their absence may provoke apoptosis (Aaronson, S. A. (1991) Science, 254: 1146–1153; Thompson, C. B. (1995) Science, 267, 1456–1462). The migration of the tumoral cell may be regulated by autocrine factors (produced and/or secreted by the same cell), paracrine (growth factors such as those of the PDGF, FGF, EGF and IGF families, whose secretion is stimulated by the stroma), normal cells of the invaded tissue and components of the extracellular matrix. Meantime, the latter also acts as a reservoir for some of these factors.

As regards the present invention, the relationship existing between proteases and the mechanism of cellular apoptosis is also relevant. There is increasing evidence which indicates that apoptosis involves the activation of a cascade of proteases which is not surprising given the fact that the dismantling of a cell requires proteolytic processes (for recent reviews, see Kumar, S. & Harvey, N. (1995) FEBS Letters, 375: 169–173; Takahashi, A. & Earnshaw, W. (1996) Curr. Opin. Genet. & Develop., 6: 50–55; Patel, T. et al. (1996) FASEB J., 10: 587–597). The most important control point to initiate the apoptosis process is in the protein, transcription factor, p53. This factor controls four important cellular mechanisms: (a) the stopping of the cellular cycle in G1 to allow (b) the repairing of the DNA provided that it is not too severely damaged; if the damage is excessive, it stimulates (c) the apoptosis, as well as it inhibits (d) the angiogenesis (Bates, S. & Vousden, K. (1996) Curr. Opin. Genet. & Develop., 6: 12–19).

Due to the suppressing effect that the IGF-IR (receptor of growth factor 1 of the insulin type, from now on referred to as "IGF-IR") has on cellular apoptosis, it presents a potentially therapeutic effect on cancer. An IGF-IR decrease at cellular level is cause of massive apoptosis of the tumoral cell in vivo (Resnikoff, M. et al. (1995) Cancer Res., 55: 2463–2469 and 3739–3741). What is more, the surviving cells are eliminated by the host, apparently by the immune system, prompting a regression of the tumor (Baserga, R. (1996) TIBTECH, 14: 150–152). In short, the IGF-IR has unique features that make it a suitable candidate target for antitumoral therapy; in other words, a molecule that would interfere with the IGF-IR would made way for: (a) massive apoptosis of tumoral cells, (b) would inhibit tumorigenicity, (c) would provoke an immune response in the host, and (d) would have a limited effect on the normal cells (Baserga, R. (1996) TIBTECH, 14: 1501 152). In addition, the IGF-IR would be a more general target than other receptors for growth factors (Baserga, R. (1995) Cancer. Res., 55: 249–252).

The IGF-IR, together with other growth factors, would play a key role in the mechanism of signal transduction. Apparently, many tumoral cells lose the redundancy of signal transduction pathway present in normal cells. This would be the most probable cause of the vulnerability of tumoral cells in front of signal transduction intercepting molecules (Levitzki, A. (1996) Curr. Opin. Cell Biol., 8: 239–244). For this reason, it is very interesting to find molecules that may intercept signal transduction, to be used on their own or in combination with others as antitumoral agents. Some or all of the receptors of growth factors would be a suitable target for intercepting signal transduction pathways.

Finally, another relevant point to take into consideration for the present invention is the structural analogy, topological, previously described between the PCI and the different cellular growth factors of the group of the knotins (Isaacs, N. (1995) Curr. Opin. Struct. Biol., 5: 391–395; Lin, S. et al. (1995) Nature Struct. Biol., 2: 835–837; Sun, P. & Davies, D. (1995) Ann. Rev. Biophys. Biomol. Struct., 24: 269–291). This analogy has made it possible to establish the hypothesis that the antitumoral activity of the PCI may be also totally or partially related to this knotin topology and not only to the protease inhibiting capacity. Thus, the PCI could act as an antagonist of growth factors and would block tumoral growth. As regards this aspect, it deserves to be mentioned that it has been reported that monoclonal antibodies against EGF interacting with heparin block the growth in vitro of some tumors and, therefore, could be used as therapeutic agents (Modjtahedi, H. & Dean, C. (1995) Biochim. Biophys. Res. Commun., 207: 389–397). In the same way, monoclonal antibodies or antisense RNA or genetic ablation or creation of dominant-negative mutants of the IGF-IR have been found to inhibit various types of tumors (for a review, see Baserga, R. (1996) TIBTECH, 14: 150–152).

Patents Relevant to the Present Invention

An exhaustive examination of the data bases on patents has not uncovered anything based on the carboxypeptidase inhibitor (PCI) as an antitumoral medicament, at least in the form and through the mechanisms established in the present invention. There is only a mention of the use of various commercial inhibitors amongst which is the carboxypeptidase inhibitor, found in creams for protection against solar radiation (U.S. Pat. No. 4,906,457). In addition, research carried out on patents in which other protease inhibitors are used has not, in any way, discorvered any other effect other than that of inhibiting proteases. Effects based on the topology of the molecule (knotin) and/or its interaction with various receptors of growth cellular factors have not been identified.

2. SUMMARY OF THE INVENTION

One of the main aims of the present invention is the use of the carboxypeptidase inhibitor (PCI) from potato, whose amino acid sequence of the most studied isoform, the IIa, is:

SEQ ID NO.2

The invention can be extended to other natural isoforms of the PCI from other solanaceous plants as antitumoral agents.

One of the aims of the present invention is to obtain the isoform II1 of the inhibitor of metalocarboxypeptidases (this form is going to be referred to from now on as "PCI", "rPCI" or "wtPCI", indifferently by means of recombinant DNA techniques and heterologous expression. Other natural variants or variants redesigned by protein engineering or chemically synthesized are also the object of the present invention.

The use of previous natural or artificial variants of the PCI as antitumoral agents is also object of the present invention.

A further object of the present invention is the determination, at cellular and molecular level, of the way in which the inhibitor of metalocarboxypeptidases carries out antitumoral activity.

Finally, it is object of the present invention to establish the structural basis responsible for the antitumoral activity of the PCI which would allow for the latter to be redesigned, as well as the design of other peptidomimetic or organomimetic molecules with better characteristics of formulation, pharmacokinetics and pharmacodynamics for their therapeutic use as antitumoral agents.

BRIEF DESCRIPTION OF THE FIGURES

FIG. 11A pretreatment, 28 days, treatment, 11 days; FIG. 11B pretreatment, 30 days, treatment, 5 days, and FIG. 11C pretreatment, 34 days, treatment, 14 days. Bars indicate the average of the number of cells in 8 wells and the vertical line, the standard error.

3. DETAILED DESCRIPTION OF THE INVENTION

Figure 1:
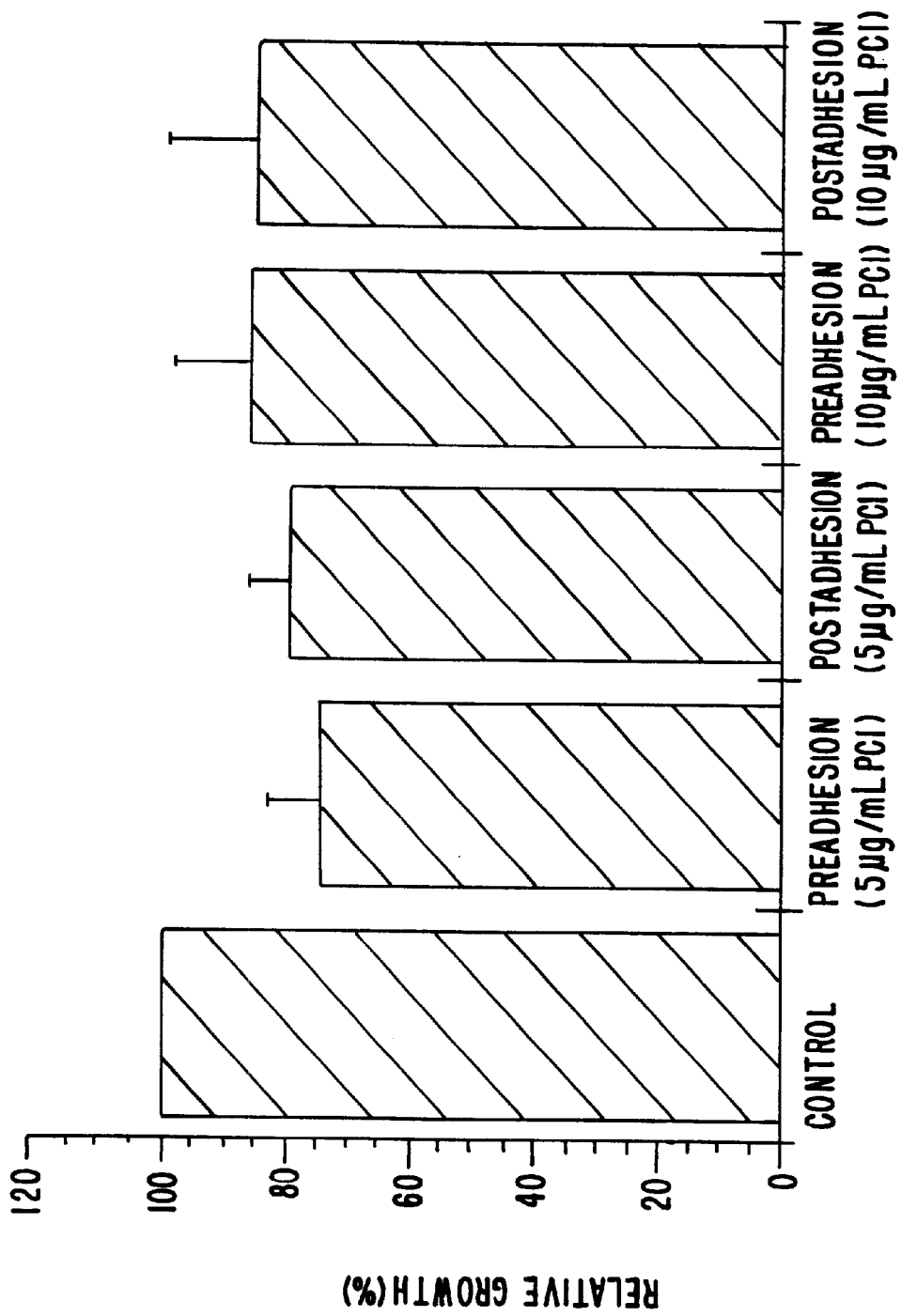
FIG. 1: Effect of the presence of PCI in the culture medium of the human pancreatic adenocarcinoma cell line MDAPanc-3. The cells were cultured in DMEM+10%BMS medium until the controls reached confluence. The results are the average of four experiments. The data are indicated as a percentage of growth in relation to the average of the controls (cells cultured in the absence of PCI). Bars indicate the standard error.

The main aim of this invention is to use a protein inhibitor of carboxypeptidase and natural variants or variants redesigned by protein engineering, as well as peptidomimetic or organomimetic molecules derived from the former, as antitumoral agents by their potential biomedical use.

In the preferred embodiment of the present invention, the previous aims have been achieved by means of a process which includes the subsidiary aims which are described as follows.

In the first place, a detailed protocol has been established for the expression of the PCI gene, obtaining and purifying the isoform IIa of the inhibitor of metalocarboxypeptidase or PCI, as well as other artificial mutant forms. This method can be applied to other variants.

To determine the antitumoral effectiveness of the PCI, various tests of cellular proliferation have been carried out with various tumoral cell lines (Capan-1, Panc-1, IBFCP3, MDAPanc-3, HIT, melanoma B-16, Int-2 and H661), in the absence and in the presence of PCI and employing various concentrations of the same. In the tests of direct recount of the number of viable cells as well as by indirectly measuring their proliferation with tetrazolium salts, an inhibitory effect of the growth in the tested tumoral cellular lines was observed. The growth curve of the cell line Capan-1, in the presence and in the absence of PCI, shows that the cells treated with PCI increase at a significantly slower rate. Growth curves of cells undergoing prolonged treatments with PCI show that the damage produced by the PCI is not reversible given the fact that, after removing the PCI, these cells continue to grow more slowly than the control cells.

The inhibitory capacity of cellular invasiveness in vitro has been determined by analyzing the migration of the cells through the membranes in the presence or in the absence of PCI, finding a significant increase of the already mentioned capacity in the presence of PCI. All the same, the inhibitory capacity of metastasis in vivo has been determined in mouse liver by injection of the murine melanoma cell line B16. In this case, a significant decrease in the metastatic capacity of the cells which had been pretreated with PCI was also found. In order to evaluate the sensitivity to PCI of induced human tumors, tests were carried out with nude mice to which cells of the human pancreatic adenocarcinoma cell line Capan-1 were inoculated subcutaneously. The corresponding analysis indicates that the PCI had a significant effect on the reduction of the growth of such tumors which show a loss of consistency and a lower level of vascularization (which indicates that the PCI would present an anti-angiogenic effect).

To determine whether the inhibiting effect of the PCI growth was due to the fact that it induces cytotoxicity in a unspecific way, or whether, to the contrary, the effect is specific, a test of cytotoxicity in vitro of the PCI on the human pancreatic adenocarcinoma cell line Capan-1 was carried out. The results indicated that the PCI did not induce a normal rate of cell death. To determine whether the treatment with PCI has an inhibitory effect on the cell cycle, the contents of DNA was analysed by means of flux cytometry throughout the cell cycle. It is observed that the PCI produces a variation in the distribution of the phases of the cell cycle, concretely, an increase of the number of cells in $G_1$, stopping the cellular division.

To establish whether the decrease of the cellular growth—from which the PCI is responsible—is related to the induction of apoptosis, those changes that are related with the apoptotic phenomenon were measured: (a) morphological by fluorescence microscope and flux cytometry, and (b) the presence of a ladder of digested DNA, no significant changes being observed.

The previous tests indicate that the potato carboxypeptidase inhibitor, isoform IIa, presents a significant inhibitory effect on the growth of tumor cell lines in culture, on the development of tumors induced in athymic mice by injection of cells of human pancreatic adenocarcinoma and on the appearance of metastasis in the liver of mice by injection of melanoma cells.

With the aim of examining in depth the cellular and molecular mechanism of action of the PCI, various tests were carried out. Firstly, by studying its concentration over a period of time, the process of internalization and disappearance of the PCI in cultures of tumoral cells was identified. Thus, it was observed that the PCI has a cycle of incorporation/release in the medium and reincorporation in the cells. Given the fact that the PCI undergoes a process of quick and massive internalization in the Capan-1 cells, with the aim of determining whether the PCI binds the receptors of growth factors, tests of competitive binding have been carried out with the corresponding receptor of the epidermic growth factor (EGF-R). The results prove the existence in Capan-1 of receptors for the EGF, one of low affinity and the other of high affinity; however, the binding is, for the most part, produced in the receptor of high affinity. Proliferation tests adding at the same time PCI and a growth factor, EGF, insulin or IGF-1, which stimulate the proliferation of the human pancreatic adenocarcinoma cell lines Panc-1 and Capan-1, were also carried out, thus observing a clear decrease in the stimulator effect of the EGF, insulin and IGF-1 in the presence of PCI.

Once it had been determined that the PCI binds the receptor of EGF (EGF-R), it was proven that the PCI acts as an antagonist of the EGF through analysis of the inhibition of the EGF receptor phosphorylation.

In order to determine whether the effect of PCI on cell growth caused important metabolic changes, the process of secretion of the ribonuclease enzyme as well as its pattern of glycosylation was analysed. No significant differences in relation to the secretion of the enzyme were observed. However, a higher level of glycosylation of the latter was observed.

With the aim of determining the putative role that PCI plays in the process of signal transduction, analyses of gene expression in Capan-1 cells were carried out by means of Northern transfer, using as probes various genes of significant proteins. It was determined that the PCI induced a strong increase in the expression of p53 protein and a decrease in the expression of trypsin. The apparent contradiction because of the lack of increase of apoptosis mentioned is not so, given the fact that it is known that the p53 of Capan-1 cells is mutated. On the contrary, the fact that the cells are stopped in $G_1$ phase appears to be coherent. The decrease in the expression of trypsin would indicate that the cell line has lost invasive power. As a whole, the results are indicative that the PCI alters some way of signal transduction; nevertheless, it cannot be specified which one.

To determine whether the inhibitory effect on cell growth of the PCI is related to its inhibitory activity of carboxypeptidase or to the specific topology of its globular core of the knotin type, tests of cell inhibition were carried out with a mutant form designed for this purpose. The three C-terminal amino acids underwent deletion, resulting in the form pCIdelY37V38G39. This form was designed and built because it maintains the structure and topology of the globular core of the wild PCI while, at the same time, it results in a PCI practically without any carboxypeptidase inhibitory activity. Tests of cellular inhibition and internalization in Panc-1 cells were carried out and it was observed that the effect of internalization and of cellular inhibition was maintained. Tests of proliferation were also carried out adding, at the same time, a growth factor, EGF, IGF-1 or insulin, which stimulate the proliferation of the human pancreatic adenocarcinoma cell line Panc-1, Capan-1 and the mutated form of the PCI. A clear decrease of the stimulatory effect of EGF, IGF-1 and insulin, was observed in the presence of the mutant form of the PCI. Apart from this, tests of cell growth inhibition of Capan-1 cells were carried out with a synthetic peptide corresponding to the C-terminal tail of the PCI, a peptide that lacks carboxypeptidase inhibitory activity. A slight inhibiting effect on the cellular growth was found.

In a further embodiment of the present invention, a graphic computerized analysis was made to determine with greater accuracy the structural basis of the cellular growth inhibitory activity of the PCI. The analysis proved that the structure of the PCI and other knotins were well matched, among the latter we have to underline EGF and TGF-α, (Transforming Growth Factor-α), identifying then the potential key residues of its interaction with the receptors. These amino acids are placed not only in the core, but also in the knot defined by the cysteines 27 and 34 residues and some of the C-terminal tail of the PCI. All of which suggests that the PCI would act through introduction with receptors of polypeptide growth factors in which it would play the role of an antagonist.

The hypotheses put forward in this invention in relation to the structural basis involved in the inhibitory effect of the cell growth and therefore of the antitumoral activity of the PCI, which does not correspond to its carboxypeptidase inhibitory activity, makes it possible to establish the physicochemical criteria that determine the design of new variants of the isoform IIa of the PCI and of peptidomimetic molecules with better formulation features -pharmacokinetic and pharmacodynamic—for their therapeutic use as antitumoral agents.

4. EXAMPLE OF THE PREFERRED EMBODIMENT OF THE PRESENT INVENTION

4.A. Expression, Obtention and Purification of the PCI, Natural Variants of the PCI and Artificial Mutants The IIa isoform of the potato carboxypeptidase inhibitor (PCI) is obtained in a recombinant way from a synthetic gene for the same, built with codon optimization for *Escheridia coli*, inserted in a secretion vector and cloned in the strain MC1061 of the afore mentioned bacterium. This is grown in a discontinuous fermenter, and the recombinant PCI is secreted into the culture medium and it is purified by means of a protocol that is made up of various chromatographic steps which are described later on. From the synthetic gene it is possible, by means of site directed mutagenesis by PCR, to obtain variants of the inhibitor, the amino acid sequence being modified. The synthetic gene was built and cloned in *Escherichia coli* in the way described in Molina et al. (1992) *Gene*, 116: 129–138. The expression and production on a large scale of recombinant PCI has been refined and described in Marino, C. et al. (1994) *Appl. Microbiol, Biotechnol.* 41: 632–637. The protocol of purification of recombinant PCI is carried out as it is described in Molina, M. A. et al. (1992) *Gene*, 116: 129–138, and Marino, C. et al. (1994) *Appl. Microbiol. Biotechnol.*, 41: 632–637.

The expression of the recombinant PCI of the wild type and of the various mutant forms is carried out in *E. coli*, employing constructions obtained from the vectors pIN-III-ompA 3, as described in Molina, M. A. et al. (1992) *Gene*, 116: 129–138. The recombinant pIMAM3 vector contains the construction which expresses the PCI of the wild type. In this construction, the first codon of the codifying sequence of the native PCI directly follows the last codon of the OmpA signal peptide. The various mutant forms of the PCI employed in this invention are obtained by site directed mutagenesis from the vector pIMAM3.

4.A.1. Culture Conditions of *E. coli* Cells which Produce Recombinant PCI

The cells of *E. coli* which carry the recombinant plasmids are grown in the following way:

1. Inoculate a night culture of *E. coli* MC1061 which carries the desired plasmid (pIMAM3 or one of its derivatives) in 10 mL of M9CAS+0.5% glycerol+50 μg/ml of Ap. Incubate at 37° C. and 300 rpm.

2. On the next day, inoculate the night culture in 1 L in the same medium. Distribute in erlenmeyers of 250 mL (approximately, 125 mL per erlenmeyer) and incubate at 37° C. and 300 rpm.

3. After 2 h, induce adding isopropyl-β-D-thiogalactotyranoside (IPTG) to a final concentration 0.2 mM from a 200 mM sterile solution.

4. At 24–30 h, distribute the culture in centrifugation tubes and centrifuge at 10,000×g for min. Collect the supernatant and divide it in aliquots of 150 mL. Keep them in the refrigerator if purification is not carried out immediately after.

To produce recombinant PCI on a larger scale, 200×mg/L or more, the following fermentation conditions are used (Marino, C. et al. (1994) *Appl. Microbiol. Biotechnol.*, 41: 632–637):

Medium M9CAS with 0.5% glycerol as source of carbon.
Mixture of oligoelements: $FeSO_4.7H_2O$, 40 mg/L; $MnSO_4.H_2O$, 10 mg/L; $CaCl_2.6H_2O$, 4 mg/L; $ZnSO_4.7H_2O$, 2 mg/L; $Na_2MoO_4$, 2 mg/L; $CuCl_2.2H_2O$, 1 mg/L; $AlCl_3$, 1 mg/L; $H_3BO_3$, 0.5 mg/L)
Temperature of culture: 37° C.
Simultaneously to the inoculation, induction of the expression of the PCI gene with IPTG 0.2 mM.
Maintain the $PO_2$ (oxygen pressure) above 50% of saturation during the entire fermentation process.
Constant shaking at 900 rpm.
Add concentrated components of M9CAS (glycerol, CAS amino acids, salts and thiamine) when an increase of $PO_2$ is observed.
Complete the process 24 h later (A550 in the range of 40–50 units).

4.A.2. Purification of recombinant PCI's

The purification of recombinant PCI's, of the wild type as well as of the mutant type from extracellular culture medium is done as follows:

All the buffers employed in HPLC and FPLC are prepared employing Mono-Q water and are filtered through membranes of 0.22 μm and degassed immediately before use. The HPLC, as well as the FPLC, are done at room temperature. The process of purification is done by determining the global concentration of proteins after each step using the Bradford method; the concentration of recombinant PCI is evaluated by measuring its inhibitory effect of CPA using appropriate blanks; or, in the case of PCI mutants with little or zero carboxypeptidase activity, by ELISA with rabbit polyclonal antibodies against PCI.

The extracellular medium is filtered by means of successive filterings through filters of 0.8, 0.4 and 0.22 μm, respectively. The employed filters are Millex-GV (Millipore, U.S.A.) for they have a low retention of proteins. Afterwards, it is concentrated up to 200 mL using tangential ultracentrifugation with a membrane of H1000-Da (Millipore). Next, it is concentrated using columns "Sep-Pak $C_{18}$ environmental" (Millipore) of 35 mL. The minicolumns Sep-Pak $C_{18}$ are reverse-phase columns already packed which retain the PCI. The samples are injected through them using a syringe. For each one of the aliquots of extracellular medium obtained in the previous step, the following process is used:

1. Pretreat a minicolumn first passing 50 mL of acetonitrile (grade HPLC) and then 100 mL of Mono-Q water through it.
2. Pass the aliquot through a filter of 0.22 μm and after through the column.
3. Wash the column first with 50 mL of acetronitrile at 10% and, then, with acetronitrile at 15% to eliminate impurities in the sample.
4. Wash the column once or twice with 100 mL of water.
5. Elute the retained with 50 mL of isopropanol at 30%. Collect it in a tube of 50 mL.
6. Evaporate the retained in the rotatory evaporator up to a volume of approximately ¹/₁₀ of the initial one. This solution is then used in the following step.

FPLC Anionic Exchange Chromatography

The column of anionic exchange employed in a first purification of recombinant PCI is a TSK-DEAE 5PW Ultropac 7.5×75 mm (LKB). In further purification processes, a column of the same type is employed but of 21.5×150 mm. The protocol here described used this last type. As FPLC kit, the FPLC System® (LKB Pharmacia) to which a computer Tandon PAC 3865x was connected. The process is carried out in the following way:

1. Prepare the buffers of FPLC which, in this case, are:
   A Buffer: Tris-acetic 20 mM pH 8.5. It is obtained by dissolving Tris in a concentration 20 mM and adjusting its 20 pH to 8.5 with glacial acetic.
   B Buffer: Tris-acetic 20 mM pH 8.5 plus ammonium acetate 0.8 M. It is obtained by dissolving the Tris and the ammonium acetate at the already mentioned concentrations and fitting the pH with ammonia. Filter and degas both buffers. Measure the conductivity of the A buffer, which usually does not exceed 400 μS.
2. Equilibrate the column passing the A buffer at a flux of 4 mL/min for at least half hour. At the end of the equilibrating process, the pH and the conductivity at the end of the column must be very similar to those of A buffer.
3. While the column is being equilibrated, centrifuge the material of stage 1 at 10,000×g for 5–10 min. Afterwards, add the A buffer up to 30 mL and measure its conductivity and pH. It must be below 1500 μS; if this happens, the material must be further diluted in A buffer. In relation to the pH, if it is less than 8.25, it has to be raised until this value (or, preferably, until 8.5) adding 1M NaOH. Finally, pass the material through a filter of 0.22 μm.
4. Load the material onto the column and carry out chromatography following this ratio:

| Time (min) | % A | % B | |
|---|---|---|---|
| 1 | 100 | 0 | |
| 30 | 100 | 0 | A: Tris-AcOH 20 mM (pH 8.5) |
| 90 | 80 | 20 | B: Tris-AcOH 20 mM; AcONH4 0.8 M (pH 8.5) |
| 100 | 0 | 100 | Flux: 4 mL/min |
| 125 | 0 | 100 | |
| 130 | 100 | 0 | |

5. Follow the course of the chromatography measuring the $A_{280}$ at the end of the column. Collect the peaks that come out of the column between the minutes 75 and 90, since it is when the recombinant PCI elutes.
6. Localize the fractions collected which contain recombinant PCI by means of determining the CPA inhibiting effect (using as blanks fractions without PCI, for instance, corresponding to the minutes 60–70) or, in the case of non-active mutants, by ELISA. Collect the PCI fractions, which make up the material in stage 2.

Second Concentration by Reverse-phase Chromatography Using Sep-Pak $C_{18}$ Minicolumns This step is not always necessary. The material used in the previous step is concentrated again by means of a Sep-Pak $C_{18}$ minicolumn with the aim of reducing its volume and eliminating the salts. The method to employ is the following:

1. Pretreat a column passing 50 mL of acetonitrile (grade HPLC) and then 100 mL of Mono-Q water.
2. Pass the material used in stage 2 through a filter of 0.22 μm and, immediately afterwards, through the column.
3. Wash the column once with 100 mL of water.
4. Elute the retained with 30 mL of isopropanol at 30%. Collect it in a 50 mL tube.
5. Evaporate the retained in the rotatory evaporator up to a volume approximately ¹/₁₀ of the initial. Such a solution is the material used in stage 3.

Reverse-phase HPLC Chromatography

The last step when purifying recombinant PCI is a reverse-phase HPLC chromatography. The column used was a semipreparatory C4, the Vydac 214TP1010 (1.0×25 cm) which has a particle size of 10 μm and a pore diameter of 30 nm. The method used is the following:

1. Prepare buffers A and B which are the following:
   A buffer: Mono-Q water with a 0.1% of TFA.
   B buffer: Acetonitrile with a 0.1% of TFA.
   Filter and degas both buffers.
2. Equilibrate the column with a mixture 80% A+20% B to a flux of 1.4 mL/min for at least 20 min.
3. While the column is being equilibrated, centrifuge the material of stage 3 at 10,000×g for 5 to 10 min.
4. Load the sample onto the column and carry out chromatography following this ratio:

| Time (min) | % A | % B | |
|---|---|---|---|
| 0 | 80 | 20 | |
| 5 | 80 | 20 | A: $H_2O$ + 0.1% TFA |
| 45 | 60 | 40 | B: $CH_3CN$ + 0.1% TFA |
| 50 | 20 | 80 | The flux is of 1.4 mL/min |
| 55 | 20 | 80 | |
| 57 | 80 | 20 | |

5. Collect in a fraction the peak of the PCI, which appears between 35 and 40 min and which is in a greater majority in relation to the rest of the peaks. If desired, check the presence of PCI by means of determining its CPA inhibiting effect using other fractions as blanks.
6. Lyophilize the previous fraction, thus obtaining purified PCI.

4.A.3. Obtaining a Mutant Variant by Means of Mutagenesis by PCR with the Aim of Determining the Structural Domain of the PCI Responsible for the Inhibiting Effect on Cellular Growth To determine whether the inhibiting effect on cellular growth of the PCI is related to its carboxypeptidase inhibiting effect or with its specific knotin topology, tests of cellular inhibition with a mutant form were carried out. Concretely, the deletion of the three C-terminal amino acids was designed resulting in the form PCIdelY37V38G39 (or PCIdelYVG). This form was designed and constructed because it keeps the structure and the topology of wild PCI. This is inferred from the fact that it presents a similar chromatographic behaviour to that of the wild form and that it can be detected by antibodies antiwtPCI. Also by means of computer simulation (by molecular dynamics using the GROMOS programme) it presented a similar behaviour to the wild form after 300 ps of dynamics. On the other hand, this deletion led to a PCI whose carboxypeptidase inhibiting effect was strongly diminished (Ki at micromolar level, which represents a decrease of the inhibitory capacity of 3 orders of magnitude).

The mutant was constructed using PCR mutagenesis following, in general, a process designed by our research team (Juncosa, M. et al. (1994) *Biotechniques*, 16: 820–821). The construction is carried out on the DNA of the synthetic gene of the PCI (Molina, M. A. et al. (1992) *Gene*, 116: 129–138) in the following way:

4 μL are taken from a solution of DNA at concentration 1.25 μg/mL.

2 mL of dNTPs are added (Boehringer Mannheim), from a 200 mM solution of the same, 17 mL of Taq polymerase (Ecogen) and 10 mL from the buffer (×10) of Taq and 5 mL of the universal oligonucleotide primer. The oligonucleotide employed to obtain the deletion of the PCI object of the present invention is:

5'-CGA ATT CCG GTC GAC CTA TTA CGG GCC GCA GGT ACG AGC-3' (SEQ ID NO:3)

Water is added up to 100 μL.

Thermocycling (Minicycler PTC-150, MJ Research) is done according to the following pattern: after preheating at 94° C., the sample is kept for 1.5 min at 94° C., 1 min at 55° C., 1 min at 72° C. and, finally, the final extension of 5 min at 72° C. 30 cycles are done.

The presence of DNA amplified by means of electrophoresis in agar gel is determined (Sambrook, J. et al., (1989) "Molecular Cloning: A Laboratory Manual"; Cold Spring Harbour Laboratory Press, Cold Spring Harbour, N.Y.).

The DNA of the agar gel is purified employing the Mermaid kit (Amersham).

The DNA is digested by means of the restriction enzymes XbaI and EcoRI (1 unit of each per μg of DNA).

The DNA of the agar gel is purified employing the Mermaid kit (Amersham).

The digested DNA is ligated to the vector M13mp18, previously digested with the same XbaI and EcoRI restriction enzymes and in the same conditions.

10 μL of the binding mixture are transformed in 100 μL of cells *E. coli* made competent according to the standard procedure (Sambrook, J. et al., (1989) "Molecular Cloning: A Laboratory Manual"; Cold Spring Harbour Laboratory Press, Cold Spring Harbour, N.Y.). It is used as strain of *E. coli*, the TG1 (supE hsd_5 thi _(lac-proAB) F'[traD36 proAB$^+$ lacI$^q$ lacZ_M15]).

Aliquots of competent cells transformed with TE and with a solution of RF DNA of M13mp18 are employed as controls. Once the colonies resulting from the transformation have been obtained, they are analysed by DNA sequencing (Sanger F. et al. (1977) *Proc. Natl. Acad. Sci. USA*, 74: 5463–5467) and those which have incorporated the desired mutation are selected.

Finally, the gene muted by digestion with the restriction enzymes is recovered and it is introduced into the expression vector pIN-III-ompA-3 (Molina, M. A. et al. (1992) *Gene*, 116: 129–138; Sambrook, J. et al. (1989) "Molecular Cloning: A Laboratory Manual". Cold Spring Harbour Laboratory Press, Cold Spring Harbour, N.Y.). The obtention, purification and characterization of the mutant PCI is carried out as described in sections 4.A.1 and 4.A.2.

4.A.4. Preparation of the C-terminal Tail of the PCI with the Aim of Determining the Structural Domain of the PCI Responsible for the Inhibiting Effect on Cellular Growth The pentapeptide H-Gly-Pro-Tyr-Val-Gly-OH, (SEQ ID NO:4) corresponding to the C-terminal tail of the PCI, was obtained by solid phase synthesis in a Wang resin (NovaBiochem) (Wang, S. S. (1973) *J. Am. Chem. Soc.*, 95: 1328) employing the strategy Fmoc/$^t$Bu (Chang, C. D. & Meienhoffer, J. (1978) *Int. J. Peptide Protein Res.*, 11: 246). The incorporation of the Fmoc-amino acids (sigma) was done using preactivation with 3 eq. of diisopropylcarbodiimide (DCI) (Sigma) and 1-hydroxybenzotriazol (HOBt) (sigma), being the coupling steps of 1 h. Finally, the peptide was liberated from the resin using a treatment of 95% acid trifluoracetic (TFA) for 90 min. The purity was determined through high performance liquid chromatography (HPLC) (Beckman) and the peptide was identified by MALDI-TOF (KRATOS).

4.B. Assays of Cell Proliferation

Various proliferation assays with various tumor cell lines were carried out, in the absence and in the presence of various concentrations of recombinant PCI. In this way, it was possible to establish that this protein, to a greater or lesser degree, inhibits the growth of the majority of the tested cell lines. The proliferation assays carried out were of three types:

4.B.1. Proliferation Tests by Recount of the Cells Number (by Means of Hemocytometer)

The material, media and solutions employed in this experiment, as well as in various of the following experiments, were:

Basic medium DMEM (Sebak-Fontlab, Germany).

Full medium with 10% of fetal bovine serum (FBS) (DMEM+10%FBS): it is prepared by mixing 200 mL of DMEM, 1 mL of 100 mM pyruvate solution (Whitaker, USA), 0.2 mL of gentamicin solution 50 mg/mL (Gibco, USA) and 20 mL of FBS (Biological Industries, Israel).

Full medium with 10% of artificial serum (BMS) (DMEM+10%BMS): it is prepared in the same way as the full medium, with 10% of FBS, but adding 20 mL of BMS instead of FBS.

Saline solution EBSS (Eagle's Balanced Salt Solution) Its composition is the following: 0.4 g/L of KLC; 6.8 g/L of NaCl; 2.2 g/L of NaHCO$_3$; 0.14 g/L of NaH$_2$PO$_4$.H$_2$O; 1 g/L of glucose and 0.2 g/L of EDTA.

Trypsin solution: it is prepared by dissolving 0.5 g of trypsin (Difco, Germany) with 0.2 g of EDTA, 8 g of NaCl, 400 mg of KLC and 350 mg of sodium citrate in 1 L of distilled water. The mixture is sterilized by filtering with appropriate equipment (Nalgene, USA) with a filter of 0.22 μm of low protein adsorption (Gelman, Germany).

Solution of trypan blue (Merck, Germany).

Plastic and sterile culture Roux flasks of 25 cm$^2$ (Nunc, Denmark).

Sterile centrifuge tubes of 15 and 50 mL (Nunc, Denmark).

In this assay and with the aim of determining whether the presence in the culture medium produces some effect on the growth in vitro of the cell lines, the final number of the cells when the control reaches monolayer is determined, in the presence and in the absence of the inhibitor. The calculation is made by direct recount of the number of cells using trypsinization and subsequent recount in a hemocytometer. The detailed method is as follows:

1. In each of the three culture flasks of 25 cm$^2$, 5×10$^5$ cells are seed and a total volume of the culture medium is added (DMEM with a 10% of fetal bovine serum or synthetic serum, according to the test) of 5 mL:

A first flask is used as control and no PCI is added to it.

PCI is added to a second flask some hours after the culture has started and once the cells have adhered to the bottom of the flask. This type of test is defined as postadherence test.

PCI is added to a third flask at the same time as the culture has begun, before the cells have had time to adhere to the bottom of the flask, thus constituting the preadherence test.

2. The cells are maintained in an incubator at 37° C., 87% of relative humidity and 10% of $CO_2$. The medium contained in the flasks is changed every 3–4 days. Medium free of PCI is added to the control flask; medium with PCI is added to the other two.

3. When the culture of one of the flasks reaches a state of monolayer (or after a specific number of days), we proceed to count the number of cells in each one of them. Firstly and in order to do that, the cells are trypsinized using the following steps:

3.1. The culture medium is removed from the flask. The cells are washed with 1 mL of EBSS buffer during 1 min. EBSS is removed.

3.2. 0.5 mL of a trypsin 0.5 g/L solution are added to the flask and it is maintained until it is observed in the inverted microscope that the cells have detached from the flask (they adopt a round and refringent morphology). To complete the separation, a knock is given to the flask. Trypsin is inactivated adding 1 mL of full medium (which contains trypsin inhibitor).

3.3. With a Pasteur pipette, the medium with the cells is collected and is centrifuged in a conic tube at 1500 rpm for 10 min in order to gather the cells.

3.4. The supernatant is removed, a suspension of the sediment in dry is carried out and 1 mL of culture medium is added.

Immediately after, the recount of the number of cells is done. To do that, an aliquot of 10 μL is taken and it is placed in an eppendorf tube. 10 μL of a solution of trypan blue dye is added. Then, it is well mixed and two aliquots of 10 μL of the mixture are taken and placed in the two zones of an hemocytometer which is placed in the inverted microscope.

The live cells are observed as being refringent and clear, while the dead ones are observed as opaque and dyed blue, for the staining is only able to penetrate dead cells. The total number of cells of the W zone of the hemocytometer is counted, differentiating between the live and the dead ones. Based on this recount, the total number of cells that was in the initial suspension (which will be the total number of cells that was in the culture) is calculated by multiplying the number obtained by 2×10$^4$. The viability (in %) is calculated by dividing the number of live cells by the total number of counted cells and multiplying it by 100.

The effect produced by the presence of PCI in the medium is expressed as % of cell growth inhibition, which is calculated according to the formula $$\% \text{ Inh.} = 100 - \left( \frac{Nr \text{ control live cells} - Nr \text{ live cells in flask with } PCI}{Nr \text{ live control cells}} \times 100 \right)$$

The effect of the presence of the PCI can also be expressed by using the cell growth % in relation to the controls (without PCI) which is calculated as follows:

$$\% \text{ Growth} = \left( \frac{Nr \text{ control live cells} - Nr \text{ live cells in flask with } PCI}{Nr \text{ live control cells}} \times 100 \right)$$

Cell proliferation assays were carried out by recounting the number of cells with the following lines:

MDAPanc-3: Human pancreatic adenocarcinoma cell line established by Frazier (Frazier, M. et al. (1990) *Pancreas*, 5: 8–16) from a liver metastasis of pancreatic adenocarcinoma moderately differentiated.

IBF-CP3: Human pancreatic adenocarcinoma cell line moderately differentiated established by Fernández (Fernández, E. et al. (1994) *Cancer*, 73: 2285–2295).

HIT: Transformed line of insulinoma of hamster (Robert, F. et al. (1981) *Proc. Natl. Acad. Sci. USA*, 78: 4339–4343).

Figure 2:
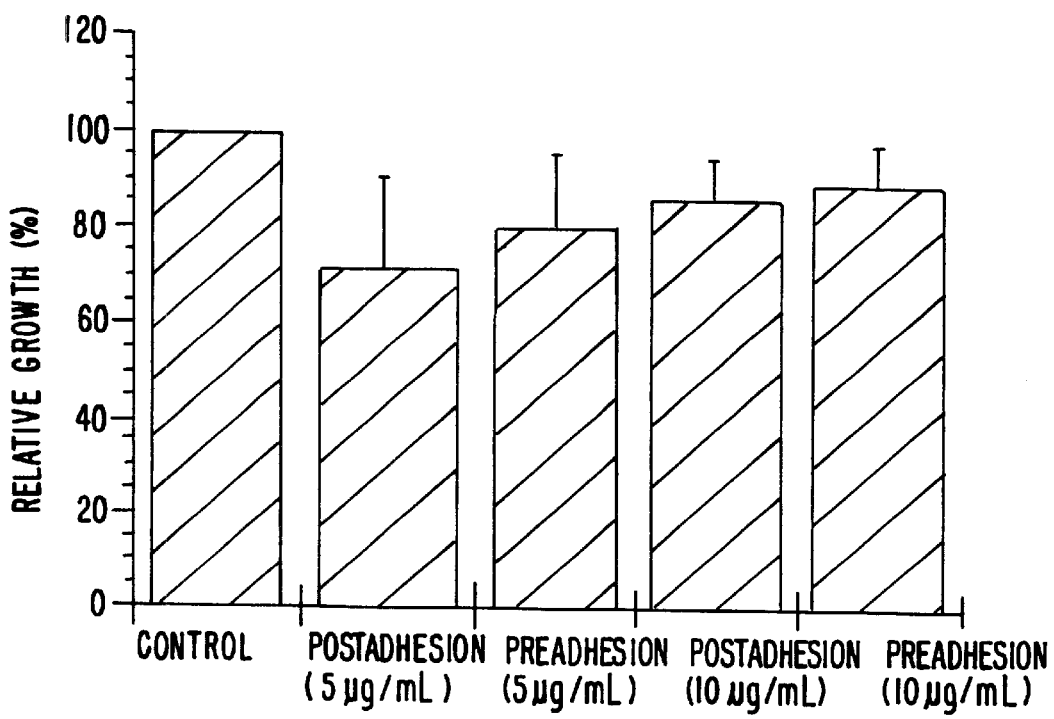
FIG. 2: Effect of the presence of PCI in the culture medium of the human pancreatic adenocarcinoma cell line IBF-CP3. The cells were cultured in DMEM+10%BMS medium until the controls reached confluence. The results are the average of four experiments. The data are indicated as a percentage of growth in relation to the average of the controls (cells in the absence of PCI) Bars indicate the standard error.

With the human pancreatic adenocarcinoma cell lines MDAPanc-3 and IBF-CP3, tests were carried out for pre and postadhesion by employing PCI concentrations of 5 and 10 μg/mL. The recount of the number of cells was done once the control cultures had reached confluence. The results of the tests are presented in Table 1 and FIGS. 1–2.

TABLE 1

| | Percentage of Growth Inhibition | | | |
| Line | 5 mg PCI/mL Preadhesion | 5 mg PCI/mL Postadhesion | 10 mg PCI/mL Preadhesion | 10 mg PCI/mL Postadhesion |
| --- | --- | --- | --- | --- |
| MDAPanc3 | 20.7 ± 6.9 | 19.1 ± 14.5 | 14.6 ± 14.2 | 14.3 ± 12.4 |
| IBF-CP3 | 20.4 ± 14.2 | 23.7 ± 19.3 | 11.6 ± 8.5 | 15.1 ± 8.3 |

As it may be observed, in the case of the two first lines, a significant inhibition of the cell growth takes place, in the preadhesion tests as well as in tests of postadhesion at the two studied PCI concentrations. No significant differences exist in the inhibition percentage of cell proliferation between the four kinds of experiments. In the case of the line of insulinoma of hamster HIT, postadhesion tests were carried out in PCI concentrations of 10 and 50 μg/mL. The PCI was added a day after the cultures had started and the recount of the number of cells was done 4 days later.

TABLE 2

| | Percentage of Growth Inhibition | |
| Line | 10 mg PCI/mL Postadhesion | 50 mg PCI/mL Postadheson |
| --- | --- | --- |
| HIT | 43.0 ± 22.8 | 60.1 ± 28.3 |

Figure 3:
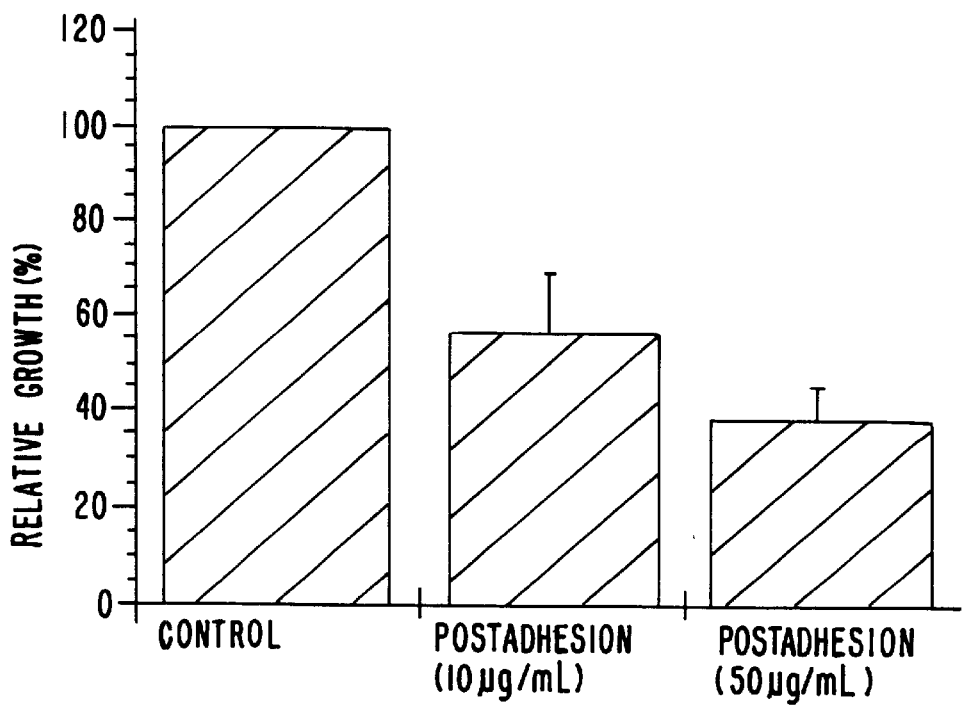
FIG. 3: Effect of the presence of PCI in the culture medium of the hamster insulinome cell line HIT. The cells were cultured in DMEM medium +10%FBS for 4 days. The results express the average of three experiments. The data are indicated as a growth percentage in relation to the average of the controls (cells cultured in the absence of PCI). Bars indicate the standard error.

The result, which is presented in Table 2 and FIG. 3, was a clear cell growth inhibition, higher than the one observed in the case of the previous lines and more noticeable at a concentration of 50 μg/mL of PCI.

4.B.2. Proliferation Test by Indirect Determination of the Number of Cells by Means of Tetrazolium Salts 4.B.2.a. Proliferation Test by Indirect Determination of the Number of Cells by Means of Tetrazolium Salts Human Pancreatic Adenocarcinoma Cell Line Capan-1 Growing in Medium with Serum Apart from the details of section 4.B.1., the material employed in this experiment was the following:

Kit EZ4U (Biomedica, Austria).

PBS buffer. Its composition is the following: 140 mM NaCl; 7.5 mM $Na_2HPO_4$; 2.5 mM $NaH_2PO_4$. Its pH is fitted to 7.5 with NaOH or phosphoric acid.

Culture plates of 96 wells (Nunc, Denmark).

In this test, with the aim of determining whether the presence of PCI in the culture medium produces some effect on the growth in vitro of the cellular lines, the final amount of cells was evaluated after a specific number of days, in presence and absence of inhibitor. The final number of cells was determined by means of tetrazolium salts (kit EZ4U) which, being added to the cultures, are reduced by mitochondrial enzymes of the cells, producing derivatives of formazan of a different colour. The amount of formed derivatives depends on the number of existing cells.

The detailed protocol that was followed was:

1. In a culture plate of 96 wells, in 48 of them, 5,000 cells were seed. Of these 48:

In 8 wells (control), 200 μL of full medium (DMEM+ 10%FBS) were added without PCI.

In 8 wells, 200 μL of full medium with 0.1 μg PCI/mL were added.

In 8 wells, full medium with 1 μg PCI/mL.

In 8 wells, full medium with 10 μg PCI/mL.

In 8 wells, full medium with 50 μg PCI/mL.

In 8 wells, full medium with 200 μg PCI/mL.

2. The cells were kept in an incubator at 37° C., 87% of relative humidity and 10% of $CO_2$. The medium contained in the wells was changed every 3–4 days. The old medium was sucked out with a Pasteur pipette. Medium free of PCI was added to the control wells and, to the others, a medium with identical concentration of PCI to which they had previously, was also added.

3. After a specific number of days, the number of cells per well was evaluated by means of the following procedure:

3.1. The culture medium of each well was sucked out and all of them were washed with 200 μL of PBS buffer which was then removed.

3.2. To each well, 200 μL of fresh PBS were added. 200 μL of PBS were placed in three wells which had no cells (the blank ones).

3.3. In each well, 20 μL of susbstrate solution (tetrazolium salt) were placed. It was incubated for 2 to 5 h at 37° C.

3.4. Then, it was lightly shaken, and the absorbency at 450 and at 620 nm of each well was determined. $A_{450}$ indicated the amount of formazan derivatives that appeared, $A_{620}$ the presence of cellular debries.

To calculate the result of the test, the following was done: the average of the $A_{620}$ of the blank ones was substracted from the $A_{620}$ of each well. Immediately after, the result of the previous subtraction, as well as the average of the $A_{450}$ of the blank ones was substracted from the $A_{450}$ of each well. The result thus obtained is directly proportional to the amount of cells present in the well. Next, the average and the typical deviation was obtained from the results of the wells which had undergone identical treatment.

The effect of the presence of the PCI can be expressed employing the cell growth percentage in relation to the controls (without PCI) which is easily calculated:

$$\% \ Growth = \frac{Average \ results \ wells \ with \ PCI}{Average \ results \ control \ wells} \times 100$$

A proliferation test with indirect determination of the number of cells by means of tetrazolium salts using the cell line Capan-1 was carried out. This is a human pancreatic adenocarcinoma cell line (ATCC nr. HTB-79), established by Fogh, G. et al. (1977) *J. Natl. Cancer Inst.,* 58: 209–214, and Fogh, J. et al. (1977) *J. Natl. Cancer Inst.,* 59: 221–226, from a liver metastasis.

As it has been explained, the cells were cultivated for 23 days, after which the cell growth was evaluated per well by means of tetrazolium salts. The results obtained are expressed in Table 3, where the average, the standard deviation and the standard error of the cell growth in relation to the controls are shown.

From these data, a Student's t test was carried out. The growth averages in each treatment were contrasted with the average of the controls. The result was that, for all the treatments, the averages are significantly different compared with the control average with a very high level of significance (inferior to 0.001 which is equal to a confidence level higher than 99.9%). Therefore, it may be concluded that the PCI has very significant inhibitory effects on the growth of Capan-1 cell line in medium DMEM+10%FCS.

TABLE 3

Growth (Percentage in relation to the average of the controls)

| Concentration of PCI in the medium (mg/mL) | Media | Standard Deviation | Standard Error |
|---|---|---|---|
| 0 (control) | 100 | 26.1 | 9.9 |
| 0.1 | 19.4 | 8.3 | 2.9 |
| 1 | 17.1 | 9.6 | 3.4 |
| 10 | 50.0 | 16.5 | 5.8 |
| 50 | 44.8 | 14.5 | 5.2 |
| 200 | 43.3 | 10.1 | 3.6 |

Figure 4:
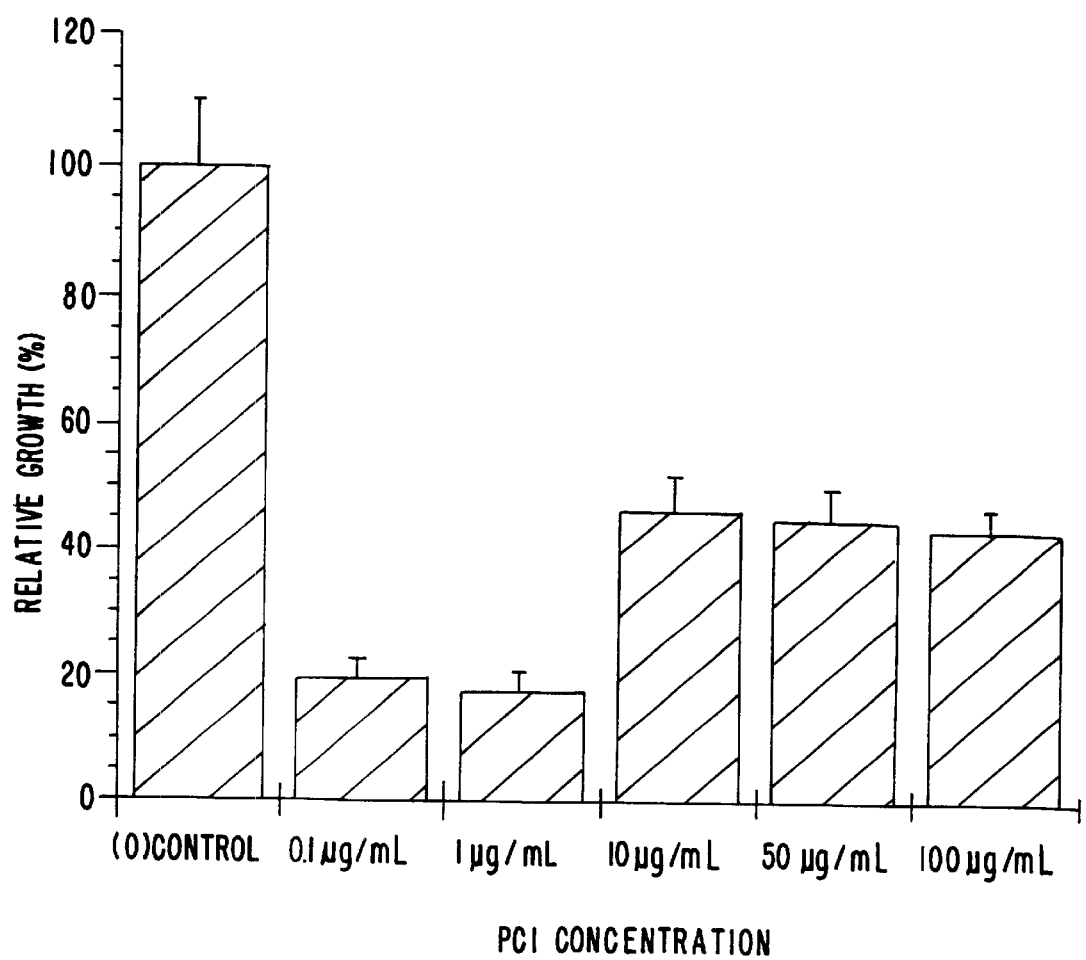
FIG. 4: Effect of the presence of PCI in the culture medium of the human pancreatic adenocarcinoma cell line Capan-1. The cells were cultured in DMEM medium +10%BMS for 23 days, with changes in medium every five days. For each concentration of PCI, eight replicas were made. The data are indicated as a percentage of growth in relation to the average of the controls (cells cultured in the absence of PCI). Bars indicate the standard error.

The data are graphically represented in FIG. 4. As it can be seen, after 23 days of culture, the growth of Capan-1 cells is inhibited in a very significant way due to the presence of PCI in the culture medium in all the tested concentrations. In concentrations of 0.1 and 1 μg/mL it has been observed that the cell growth does not reach 20% of the growth of the control cells, that is to say, PCI provokes an inhibition of the growth higher than 80%. In concentrations of 10, 50 and 200 μg/mL, the inhibition of the growth appears to be similar: approximately, 50%.

4.B.2.b. Proliferation Test by Indirect Determination of the Number of Cells of the Human Pancreatic Adenocarcinoma Cell Line Capan-1 Growing in Free-serum Medium Plus Variants of PCI Tests such as those mentioned in Section 4.B.2.a. were carried out, the main difference being that the cells were grown in medium without bovine fetal serum on the days of the test. In addition to the material detailed in Sections 4.B.1. and 4.B.2., the material used in this assay was the following:

Free-serum medium (DMEM-FBS) it is prepared by mixing 200 mL of DMEM, 1 mL of 100 mM pyruvate solution (Whitaker, USA), 0.2 mL of 50 mg/mL gentamicin solution (Gibco, USA), BSA (bovine serum albumin) at a final concentration of 1%.

Tail: synthetic peptide corresponding to the last five amino acids of the C-terminal tail of the PCI, H-Gly-Pro-Try-Val-Gly-OH (SEQ ID NO:4).

Serum-free medium (SFM): it is prepared by mixing 200 mL of DMEM, 1 mL of 100 mM pyruvate solution, 0.2 mL 50 mg/mL gentamicin solution, BSA (bovine serum albumin) at a final concentration of 1%, transferrin at a final concentration 5 $\mu$g/mL and sodium selenite at a final concentration 5 ng/mL.

Full medium with 10% of fetal bovine serum (FBS) (DMEM+10%FBS): it is prepared by mixing 200 mL of DMEM, 1 mL of 100 mM pyruvate solution, 0.2 mL of 50 mg/mL gentamicin solution and 20 mL of FBS (Biological Industries, Israel).

Mutant delYVG: mutant obtained in a recombinant form to which the last three amino acids of the C-terminal tail have undergone deletion; that is to say, Tyr-Val-Gly.

EGF solution: a solution is made using 100 $\mu$g/mL of EGF in 1 mM acetic acid-0.2%BSA, which is sterilized by filtering. Then, a solution 1:10 of the mother solution is obtained also using 10 mM acetic acid-0.2%BSA.

Insulin solution: a insulin stock solution 10 mg/mL in milliQ grade water is prepared and sterilized by filtering. Later dilutions are carried out in PBS-0.1%BSA.

IGF-1 solution: a solution 3.3 $\mu$p of IGF-1 is prepared using 10 mM acid acetic-0.2%BSA, which is sterilized by filtering. After, a dilution 1:10 of the mother solution is made also using 10 mM acetic acid-0.2%BSA.

Two kinds of tests were carried out; the first one is the treatment of cells of the human pancreatic adenocarcinoma cell line Capan-1 with wtPCI and tail added to the culture medium in absence of serum.

The protocol that was followed is detailed here:

1. In a culture plate with 96 wells, 5,000 cells were seed per well, in 24 of them. The cells were placed in full medium (DMEM+10%FBS).

2. After 24 h, once the adhesion of the cells to the surface of the well had taken place, the medium of the wells was removed and these were treated as follows:

In 6 wells (control): 200 $\mu$L of serum-free medium (DMEM-FBS) and free of tail were added.

200 $\mu$L of serum-free medium with 50 $\mu$g/mL of native PCI were added.

In 6 wells, 200 $\mu$L of serum-free medium with 0.128 $\mu$g of tail/mL were added.

In 6 wells, serum-free medium with 6.4 $\mu$g of tail/mL was added.

3. The cells were kept in an incubator at 37° C., 87% of relative humidity and 10% of $CO_2$. The medium contained in the wells was changed every 3–4 days. The old medium was sucked out using a Pasteur pipette. Medium free of tail was added to the control wells and to the others, medium with an identical concentration of tail as they had.

4. After 16 days, the cell growth per well was evaluated according to the method detailed in the protocol of Section 4.B.2.a.

Table 4 contains the results obtained in the proliferation tests with indirect determination of the number of cells by means of tetrazolium salts using the Capan-1 cell line, growing in serum-free medium for 16 days under the conditions previously outlined.

TABLE 4

Growth (Percentage in relation to the average of the controls)

| Treatment | Average | Standard Deviation | Standard Error |
|---|---|---|---|
| Control | 100 | 14.62 | 6.5 |
| 50 mg/mL wtPCI | 107.6 | 10.64 | 4.7 |
| 0.128 mg/mL tail | 81.95 | 14.39 | 6.4 |
| 6.4 mg/mL tail | 77 | 10.59 | 4.7 |

From these data a Student's t test was carried out. The growth averages were contrasted in each treatment with the average of the controls. The result was that when we grow cells in conditions which are not optimal, that is to say, without either serum or sodium selenite or transferrin, essential for these cells (as is shown in Fernández et al., 1994), the cells do not g row normally and the wtPCI has no effect, possibly because the cells are not growing optimally anymore in the control situation. However, even in these conditions, an inhibitory effect of the tail is observed, an effect which is clearly significant ($\alpha=0.025$) in low concentrations of tail and less significant ($\alpha=0.1$) in high concentrations of tail.

Figure 5:
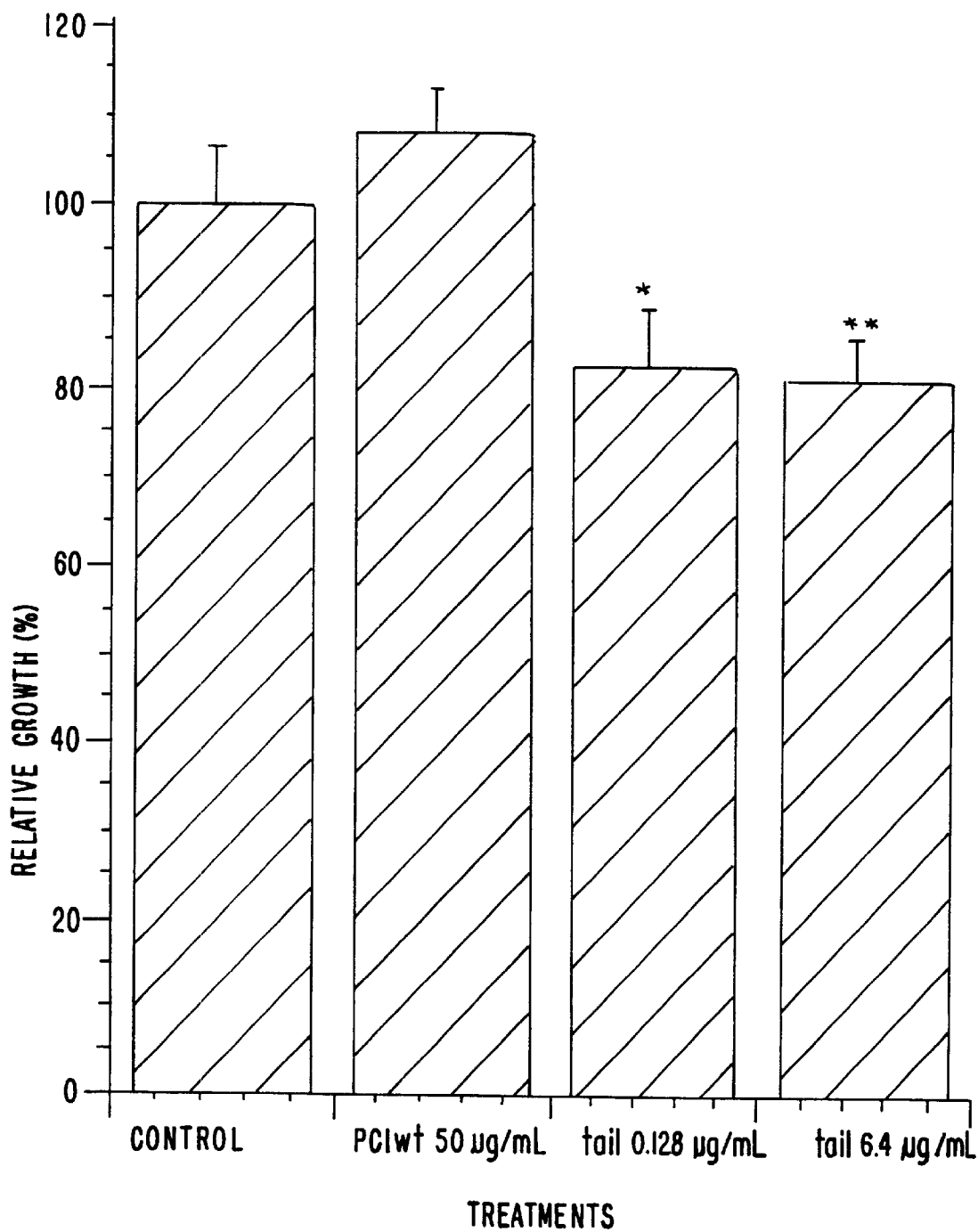
FIG. 5: Effect of the presence of PCI of the wild type (from now on referred to as "wtPCI") and tail (pentapeptide having the sequence of residues 35–39 of the PCI) in the culture medium of the growth of the human pancreatic adenocarcinoma cell line Capan-1. The cells were cultured in DMEM medium without FBS or sodium selenite, or transferrin for 16 days, with changes in medium every 4 days. For each treatment, 6 replicas were made. The data are indicated as a growth percentage in relation to the average of the controls (cells cultured in the absence of wtPCI or tail). Bars indicate the standard error. $*p<0.1$, $**p<0.025$.

The data are graphically represented in FIG. 5. As it can be seen, after 16 days of culture with serum-free medium, the growth of Capan-1 cells is not altered by the presence of wtPCI in the medium. The presence of the tail at a concentration of 0.128 $\mu$g/mL inhibits 19.34% the growth and at a concentration of 6.4 $\mu$g/mL, the inhibition is similar —18%—, although less significant.

Other kinds of tests were also carried out, the cells growing in serum-free medium as well; these were studies at short periods of time, 72 h, and of competitiveness with a growth factor plus wtPCI, PCIdelYVG or tail. There were three growth factors which were studied: EGF, insulin and IFG-1. The protocol followed was the same for the three growth factors and the only thing which was different was the concentration used in each one of them which was 10 ng/mL, 5 $\mu$g/mL and 20 ng/mL, respectively, for the EGF, the insulin and the IGF-1. The protocol employed was as follows:

1. In a culture plate of 96 wells, in 42 of which 5,000 cells per well were seed. The cells were placed in full medium (DMEM+10%FBS).

2. After 72 h, once the adhesion of the cells to the surface of the well had taken place, as well as their division, the medium was removed from the wells and to eliminate the remainder of the serum, 200 $\mu$L of PBS were added to each well.

3. The PBS was removed and 200 $\mu$L of DMEM-FBS were added.

4. After 24 h, the medium was removed and the following treatments were applied:

In 6 wells (control): 200 $\mu$L of serum-free medium (SFM) were added.

200 $\mu$L of SFM at a final concentration 10 ng/mL of EGF or 5 $\mu$g/mL of insulin or 20 ng/mL of IGF-1 were added to 6 wells.

200 $\mu$L of SFM plus the indicated concentration of one of the growth factors and wtPCI were added in 6 wells at a final concentration of 50 $\mu$g/mL.

In 6 wells, 200 $\mu$L of SFM plus the indicated concentration of one of the growth factors and PCIdelYVG were added at a final concentration of 46 $\mu$g/mL.

In 6 wells, 200 $\mu$L of SFM plus the indicated concentration of one of the growth factors and tail at a final concentration of 6.4 $\mu$g/mL were added.

In 6 wells, 200 μL of SFM plus the indicated concentration of one of the growth factors and wtPCI were added at a final concentration of 50 μg/mL combined with tail at a final concentration of 6.4 μg/mL.

In 6 wells, 200 μL of SFM plus the indicated concentration of one of the growth factors and PCIdelYVG were added at a final concentration of 46 μg/mL combined with tail at a final concentration of 6.4 μg/mL.

4. Cells were kept in an incubator at 37° C., 87% of relative humidity and 10% of $CO_2$.

5. After 72 h, the cellular growth per well was evaluated using the method detailed in the protocol of Section 4.B.2.a.

In Tables 5, 6 and 7, we can see the results obtained in the proliferation test with indirect determination of the number of cells by means of tetrazolium salts and carried out with the Capan-1 cell line, growing in SFM for 72 h under the conditions already outlined.

TABLE 5

Growth (Percentage in relation to the average of the controls)

| Treatment | Average | Standard Deviation | Standard Error |
|---|---|---|---|
| Control | 100 | 21.11 | 8.62 |
| EGF 10 ng/mL | 106.66 | 20.98 | 8.85 |
| EGF 10 ng/mL + 50 mg/mL wtPCI | 30.63 | 6.65 | 2.71 |
| EGF 10 ng/mL + 50 mg/mL wtPCI + 6.4 mg/mL tail | 51.25 | 12.87 | 5.25 |
| EGF 10 ng/mL + 46 mg/mL PCIdelYVG | 40.83 | 9.98 | 4.07 |
| EGF 10 ng/mL + 46 mg/mL PCIdelYVG + 6.4 mg/mL tail | 2.63 | 4.43 | 1.8 |
| EGF 10 ng/mL + 6.4 mg/mL tail | 28.33 | 4.65 | 1.9 |

TABLE 6

Growth (Percentage in relation to the average of the controls)

| Treatment | Average | Standard Deviation | Standard Error |
|---|---|---|---|
| Control | 100 | 7.46 | 3.04 |
| Insulin 5 mg/mL | 292.86 | 31.73 | 12.95 |
| Insulin 5 mg/mL + 50 mg/mL wtPCI | 44.10 | 4.66 | 1.90 |
| Insulin 5 mg/mL + 50 mg/mL wtPCI + 6.4 mg/mL tail | 46.10 | 5.94 | 2.42 |
| Insulin 5 mg/mL + 46 mg/mL PCIdelYVG | 44.60 | 2.80 | 1.14 |
| Insulina 5 mg/mL + 46 mg/mL PCIdelYVG + 6.4 mg/mL tail | 39.94 | 3.34 | 1.36 |
| Insulina 5 mg/mL + 6.4 mg/mL tail | 52.58 | 10.95 | 4.47 |

TABLE 7

Growth (Percentage in relation to the average of the controls)

| Treatment | Average | Standard Deviation | Standard Error |
|---|---|---|---|
| Control | 100 | 4.69 | 1.92 |
| IGF-1 20 ng/mL | 157.87 | 8.10 | 3.31 |

TABLE 7-continued

Growth (Percentage in relation to the average of the controls)

| Treatment | Average | Standard Deviation | Standard Error |
|---|---|---|---|
| IGF-1 20 ng/mL + 50 mg/mL wtPCI | 31.11 | 9.55 | 3.89 |
| IGF-1 20 ng/mL + 50 mg/mL wtPCI + 6.4 mg/mL tail | 53.76 | 10.10 | 4.12 |
| IGF-1 20 ng/mL + 46 mg/mL PCIdelYVG | 36.81 | 4.09 | 1.67 |
| IGF-1 20 ng/mL + 46 mg/mL PCIdelYVG + 6.4 mg/mL tail | 58.48 | 11.62 | 4.75 |
| IGF-1 20 ng/mL + 6.4 mg/mL tail | 73.31 | 19.13 | 7.81 |

From these data a Student's t test was carried out. The growth averages in each treatment were contrasted with the average of the controls. The result was that in presence of growth factors (insulin and IGF-1) only a clear stimulation in relation to the control is observed, 193% for the case of the insulin and of 58% for the IGF-1 ($\alpha=0.001$); meantime, in the case of the EGF alone, at the tested concentration, no differences in relation to the control situation were observed. For the treatments with compounds of wtPCI, PCIdelYVG or tail, together with EGF, a very significant inhibition of the growth is observed in relation to the control situation ($\alpha=0.001$) which oscillates between 60 and 70% of inhibition. This effect is maintained when doing a combined treatment of wtPCI or PCIdelYVG plus tail and EGF. The treatments combined with insulin prove to be equally strongly inhibiting ($\alpha=0.001$) for any of them, in this case the inhibition oscillating between 50 and 60% in relation to the control situation. Finally, in the case of combination treatments with IGF-1, clear inhibiting effects ($\alpha=0.001$, in most of the treatments) are observed, the inhibition oscillating from 30 to 70% in relation to the control situation.

Figure 6C:
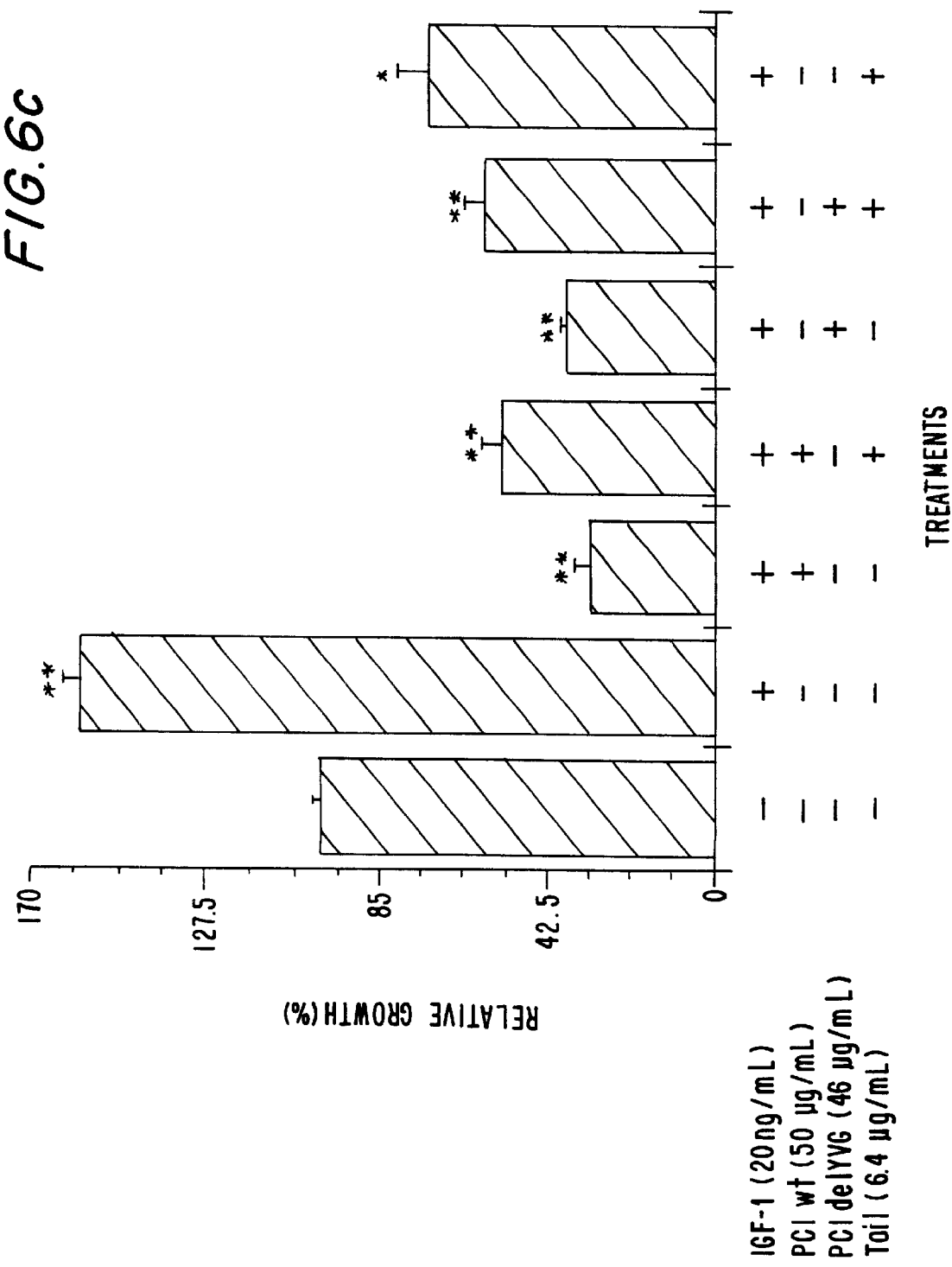
FIG. 6: Effect of the presence of growth factors alone or combined with wtPCI, PCIdelYVG or tail in the culture medium of the human pancreatic adenocarcinoma cell line Capan-1. The cells were cultured in DMEM medium plus FBS for 72 h; after washing with PBS, the cells were cultured for a further 24 h in DMEM without FBS. Afterwards, treatments in DMEM without FBS, sodium selenite, transferrin and BSA, but with growth factors and the PCI or variants for 72 h were carried out. a) Treatment with EGF alone or combined with PCI, PCIdelYVG and tail; b) Treatment with insulin alone or combined with PCI, PCIdelYVG and tail and c) Treatment with IGF-1 alone or combined with PCI, PCIdelYVG and tail. For each treatment, 6 replicas were made. The data are indicated as a growth percentage in relation to the average of the controls (cells cultured in the absence of the factors object of the study). Bars indicate the standard error. $*p<0.005$, $**p<0.001$.

The data are graphically represented in FIG. 6. As it can be seen, after 72 h of culture in SFM, the growth of the Capan-1 cells is clearly stimulated by the presence of insulin and IGF-1 in the medium, while the EGF does not affect the growth. The presence of wtPCI, PCIdelYVG, tail or combinations with tail in competitiveness with EGF, insulin or IGF-1 produces a clear reduction in cell growth.

4.B.2.c. Proliferation Test by Indirect Determination by Means of Tetrazolium Salts Using Cells of the Pancreatic Adenocarcinoma Cell Line Panc-1.

It was performed the same kind of test which had been carried out for the Capan-1 cell line but with Panc-1, another human pancreatic adenocarcinoma cell line. We are referring to a human pancreatic adenocarcinoma ATCC nr. CRL 1469, established by Lieber, M. et al. (1975) *In. J. Cancer*, 15: 741–747. Of ductal origin, it is not highly differentiated.

In addition to the material detailed in Sections 4.B.1. and 4.B.2., the material used was the following:

Serum-free medium (RPMI-FBS): it is prepared by mixing 200 mL of RPMI, 1 mL of 100 mM pyruvate solution, 0.2 mL of 50 mg/mL gentamicin solution, BSA (bovine serum albumin) at a final concentration of 1%, transferrin at a final concentration of 5 μg/mL and sodium selenite at a final concentration of 5 μg/mL.

Full medium with a 10% of fetal bovine serum (FBS) (RPMI+10%FBS): it is prepared by mixing 200 mL of RPMI, 1 mL of 100 mM pyruvate solution, 0.2 mL of 50 mg/mL gentamicin solution and 20 mL of FBS.

Serum-free medium (SFM); it is prepared by mixing 200 mL of RPMI, 1 mL of 100 mM pyruvate solution, 0.2 mL of 50 mg/mL gentamicin solution, BSA (bovine serum albumin) at a final concentration of 1%, transferrin at a final concentration of 5 μg/mL and sodium selenite at a final concentration of 5 ng/mL.

Mutant delYVG: mutant of the PCI obtained in a recombinant form, the last three amino acids of the C-terminal tail having undergone deletion, that is to say, Tyr-Val-Gly.

EGF solution: a solution 100 μg/mL of EGF in 10 mM acetic acid-0.2%BSA is prepared and is sterilized by filtering. After, a dilution 1:10 of the mother solution is also carried out in 10 mM acetic acid-0.2%BSA.

Insulin solution: an insulin stock solution 10 μg/mL in milliQ grade water, which is sterilized by filtering was prepared. Later dilutions were carried out in PBS-0, 1%BSA.

Solution of IGF-1: a solution 3.3 μM of IGF-1 in 10 mM acetic acid-0.2%BSA was prepared and sterilized by filtering. Then, a solution 1:10 of the mother solution was carried out also in 10 mM acid acetic-0.2%BSA.

As for the Capan-1 cell line, two types of experiments were carried out with and without bovine fetal serum. The protocol followed for the test, growing in RPMI plus bovine fetal serum, was the same as that used with Capan-1 cell line but with small variations, given the difference in the duplication times between the two lines. The tests were carried out with the native PCI (wtPCI) and with the mutant PCI (PCIdelYVG). The protocol is detailed as follows:

1. In a culture plate with 96 wells, 2,000 cells were seed in 30 wells for the tests with wtPCI and in 36 for the tests with PCIdelYVG. From these 30 or 36:

In 6 wells (control), 200 μL of full medium (RPMI+10%FBS) without wtPCI or PCIdelYVG/mL were added.

In 6 wells, 200 μL of full medium with 0.1 μg wtPCI/mL or 0.092 g PCIdelYVG/mL were added.

In 6 wells, full medium with 1 μg wtPCI/mL or 0.92 μg PCIdelYVG/mL.

In 6 wells, full medium with 10 μg wtPCI/mL or 9.2 μg PCIdelYVG/mL.

In 6 wells, full medium with 50 μg wtPCI/mL or 23 μg PCIdelYVG/mL.

In 6 wells, full medium with 46 μg PCIdelYVG/mL.

2. The cells were kept in an incubator at 37° C., 87% of relative humidity and 10% of $CO_2$. The old medium was sucked out with a Pasteur pipette. Medium free of wtPCI or PCIdelYVG was added to the control wells and to the others a medium was added with identical concentration of wtPCI or PCIdelYVG.

3. After 10 days, the cell growth was evaluated per well, according to the method detailed in the protocol of Section 4.B.2.a.

Table 8 shows the results obtained in the proliferation test with indirect determination of the number of cells by means of the tetrazolium salts carried out with the Panc-1 cell line, growing in medium with serum for 10 days treated with various concentrations of wtPCI.

TABLE 8

Growth (Percentage in relation to the average of the controls)

| Treatment | Average | Standard Deviation | Standard Error |
|---|---|---|---|
| Control | 100 | 8.14 | 3.64 |
| 0.1 mg/mL wtPCI | 90.85 | 1.89 | 0.85 |
| 1 mg/mL wtPCI | 84.55 | 6.41 | 2.87 |
| 10 mg/mL wtPCI | 82.22 | 6.19 | 2.77 |
| 50 mg/mL wtPCI | 71.14 | 8.11 | 3.63 |

From these data a Student's t test was carried out. The growth averages in each treatment were contrasted with the average of the controls. The result was that, for all the treatments, the averages are significantly different to the average of the control with a level of significance of 0.05, 0.005, 0.005 and 0.001 for the treatments of 0.1, 1.10 and 50 μg/mL, respectively. We may conclude that PCI has significant inhibiting effects on the growth of the Panc-1 cell line in medium RPMI+10%FCS.

Figure 7:
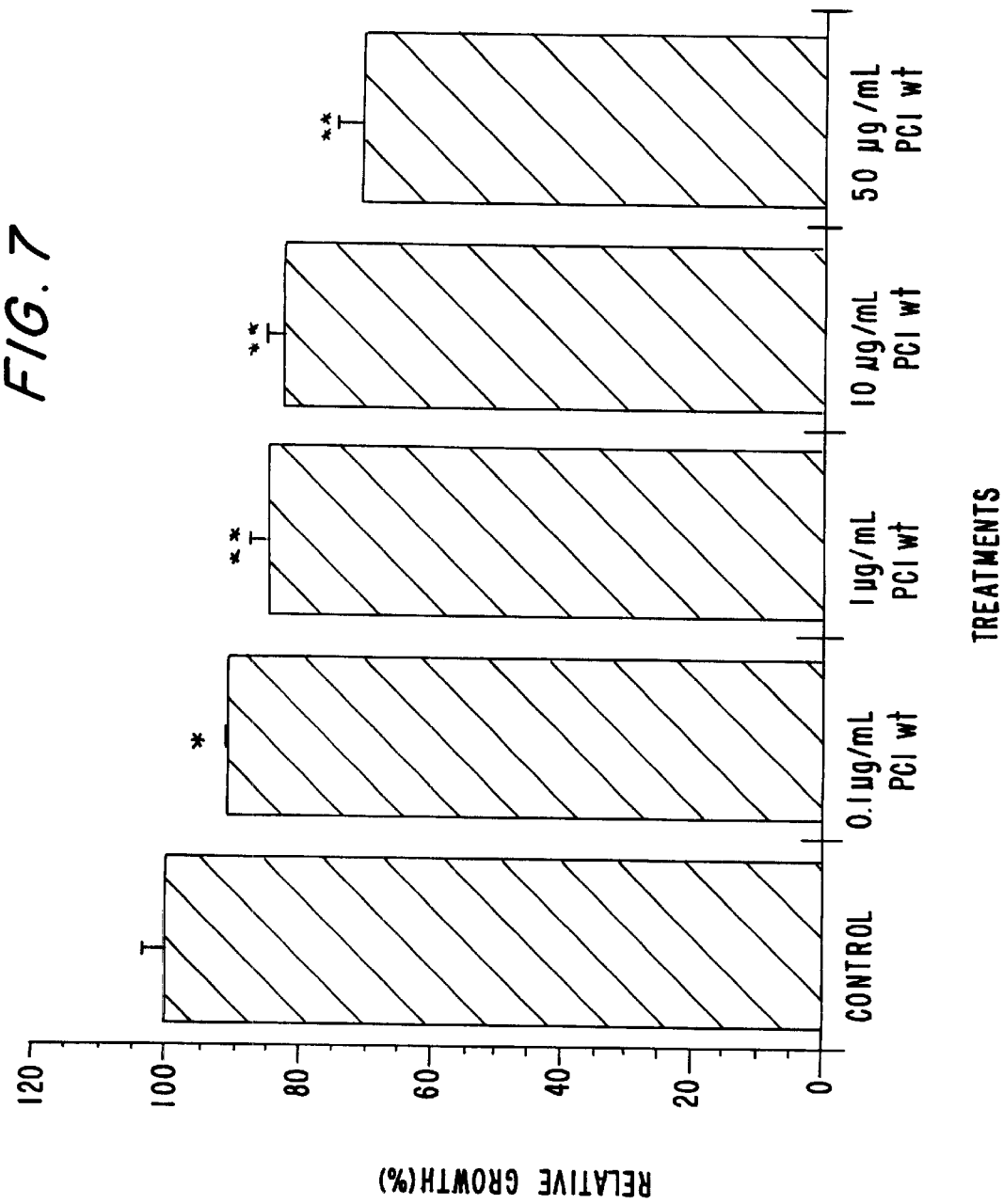
FIG. 7: Effect of the presence of PCI in the culture medium of the human pancreatic adenocarcinoma cell line Panc-1. The cells were cultured in RPMI medium+10%FBS for 10 days, with changes in medium every 3 days. For each treatment, 6 replicas were made. The data are indicated as a growth percentage in relation to the average of the controls (cells cultured in the absence of wtPCI). Bars indicate the standard error. $*p<0.05$, $p<0.005$, $*p<0.001$.

The data are graphically represented in FIG. 7. As we can see, after 10 days of culture, the growth of the Panc-1 cells is inhibited in a significant way by the presence of wtPCI in the culture medium in all the tested concentrations. The inhibition increases as the concentration of PCI in the medium also increases, the lowest level of inhibition being of 9.15% for the concentration of 0.1 μg/mL and the highest level of inhibition being of 28.86% and corresponding to the concentration of 50 μg/mL.

Table 9 presents the results obtained in the test carried out with the Panc-1 cell line, growing in medium with serum for 10 days and treated with various concentrations of PCIdelYVG.

TABLE 9

Growth (Percentage in relation to the average of the controls)

| Treatment | Average | Standard Deviation | Standard Error |
|---|---|---|---|
| Control | 100 | 6.28 | 2.81 |
| 0.092 mg/mL PCIdelYVG | 112.92 | 6.28 | 2.81 |
| 0.92 mg/mL PCIdelYVG | 105.43 | 3.74 | 1.67 |
| 9.2 mg/mL PCIdelYVG | 105.16 | 14.24 | 6.37 |
| 23 mg/mL PCIdelYVG | 94.85 | 5.69 | 2.54 |
| 46 mg/mL PCIdelYVG | 85.51 | 2.75 | 1.23 |

From these data a Student's t test was carried out. The growth averages in each treatment were contrasted with the average of the controls. The result was that the PCIdelYVG at low concentrations, 0.092 μg/mL, significantly stimulates the growth of the Panc-1 cell line ($\alpha=0.005$) while at high concentrations, 46 μg/mL, it inhibits very significantly the growth ($\alpha=0.001$). We may conclude that the PCIdelYVG has stimulating effects as well as inhibiting effects (depending on the concentration) on the growth of the Panc-1 cells in medium RPMI+10%FCS)

Figure 8:
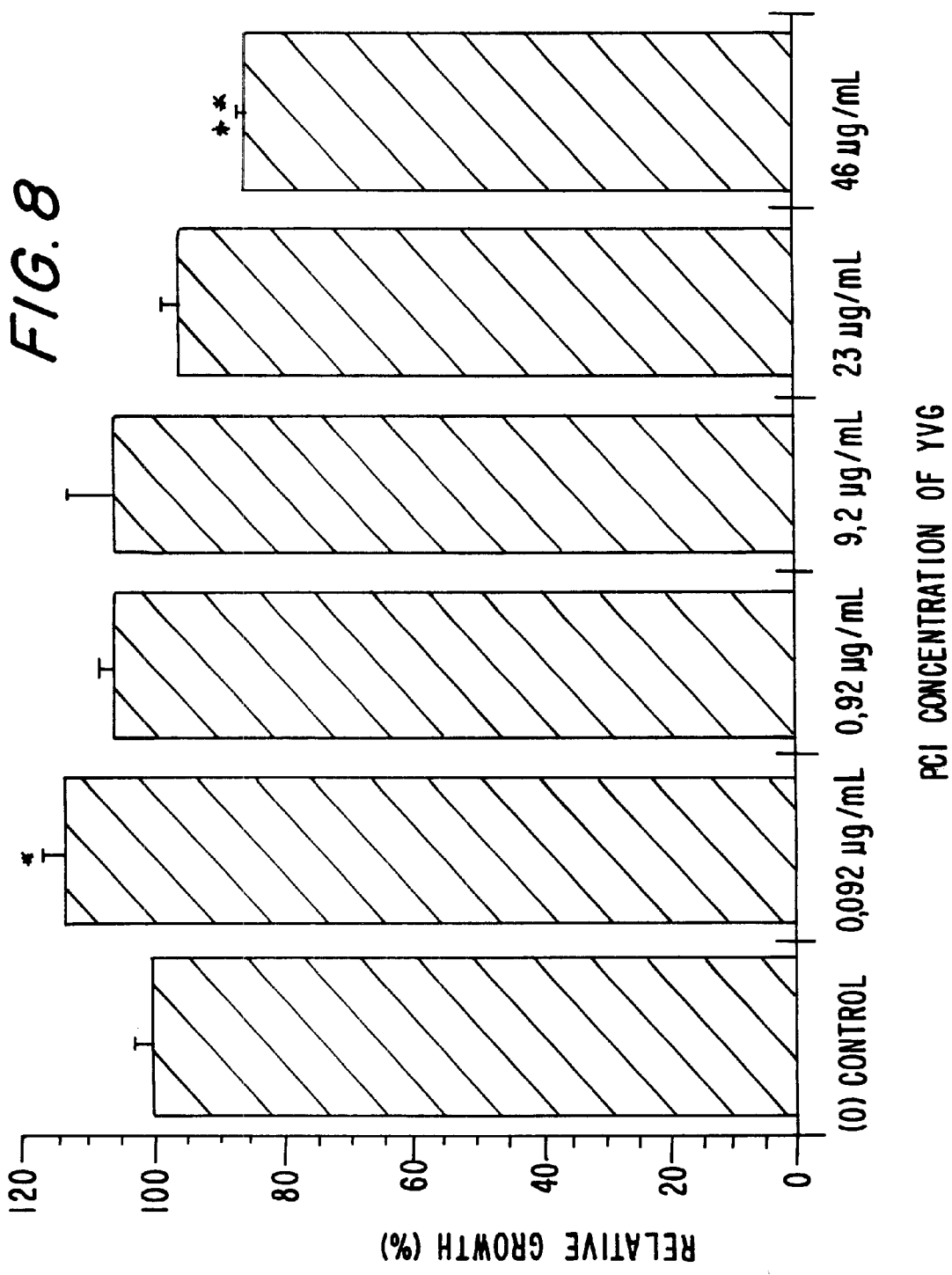
FIG. 8: Effect of the presence of PCIdelYVG in the culture medium of the human pancreatic adenocarcinoma cell line Panc-1. The cells were cultured in RPMI medium+10%FBS for 10 days, with changes in medium every 3 days. For each treatment, 6 replicas were made. The data are indicated as a growth percentage in relation to the average of the controls (cells cultured in the absence of PCIdelYVG). Bars indicate the standard error. $*p<0.005$, $**p<0.001$.

The data are graphically represented in FIG. 8. As it can be seen, after 10 days of culture, the growth of the Panc-1 cells is stimulated in a very significant way by the presence of PCIdelYVG in the culture medium in the concentration 0.092 μg/mL, this stimulus being of 13%. Contrarily, in the 46 μg/mL concentration, a very significant inhibition of the growth of 15% takes place.

The tests that were carried out growing in free bovine fetal serum medium were very similar to those used in the line Capan-1 described in Section 4.B.2.b. The protocol employed is as follows:

1. A culture plate with 96 wells, in 42 of which 5,000 cells were seed per well. The cells were placed in full medium (RPMI+10%FBS).

2. After 48 h, after the cells had adhered to the surface of the well and they had divided as well, the medium was drained from the wells and to eliminate the rest of the serum, 200 μL of PBS were added to each well.

3. The PBS was removed and 200 μL of RPMI-FBS were added.

4. After 48 h, the medium was removed and the following treatments were applied:

In 6 wells (control): 200 μL of serum-free medium (SFM) were added.

200 μL of serum-free medium (SFM) with a final concentration 10 ng/mL of EGF or 5 μg/mL of insulin or 20 ng/mL of IGF-1 were added to 6 wells.

In 6 wells, 200 μL of SFM plus the indicated concentration of one of the growth factors and wtPCI at a final concentration of 50 μg/mL were added.

In 6 wells, 200 μL of SFM plus the indicated concentration of one of the growth factors and PCIdelYVG at a final concentration of 46 μg/mL were added.

In 6 wells, 200 μL of SFM plus the indicated concentration of one of the growth factors and tail at a final concentration of 6.4 μg/mL were added.

In 6 wells, 200 μL of SFM plus the indicated concentration of one of the growth factors and wtPCI at a final concentration of 50 μg/mL combined with tail at a final concentration of 6.4 μg/mL were added.

In 6 wells, 200 μL of SFM plus the indicated concentration of one of the growth factors and PCIdelYVG at a final concentration of 46 μg/mL combined with tail at a final concentration of 6.4 μg/mL were added.

The cells were kept in an incubator at 37° C., 87% of relative humidity and 10% of $CO_2$.

5. After 72 h, the cell growth per well was evaluated using the method detailed in the protocol of Section 4.B.2.a.

Tables 10, 11 and 12 show the results obtained in the proliferation test with indirect determination of the number of cells by means of tetrazolium salts used for the Panc-1 cell line, growing in SFM for 72 h using the treatment already detailed above.

TABLE 10

Growth (Percentage in relation to the average of the controls)

| Treatment | Average | Standard Deviation | Standard Error |
|---|---|---|---|
| Control | 100 | 7.07 | 2.87 |
| EGF 10 ng/mL | 63.52 | 1.99 | 4.89 |
| EGF 10 ng/mL + 50 mg/mL wtPCI | 15.81 | 3.45 | 1.41 |
| EGF 10 ng/mL + 50 mg/mL wtPCI + 6.4 mg/mL tail | 25.95 | 5.80 | 2.37 |
| EGF 10 ng/mL + 46 mg/mL PCIdelYVG | 5.53 | 4.93 | 2.01 |
| EGF 10 ng/mL + 46 mg/mL PCIdelYVG + 6.4 mg/mL tail | 17.61 | 6.39 | 2.61 |

TABLE 10-continued

Growth (Percentage in relation to the average of the controls)

| Treatment | Average | Standard Deviation | Standard Error |
|---|---|---|---|
| EGF 10 ng/mL + 6.4 mg/mL tail | 16.23 | 6.24 | 2.55 |

TABLE 11

Growth (Percentage in relation to the average of the controls)

| Treatment | Average | Standard Deviation | Standard Error |
|---|---|---|---|
| Control | 100 | 7.45 | 4.62 |
| Insulin 5 mg/mL | 193.47 | 31.73 | 15.55 |
| Insulin 5 mg/mL + 50 mg/mL wtPCI | 26.34 | 3.42 | 1.40 |
| Insulin 5 mg/mL + 50 mg/mL wtPCI + 6.4 mg/mL tail | 14.03 | 3.18 | 1.30 |
| Insulin 5 mg/mL + 46 mg/mL PCIdelYVG | 21.41 | 3.46 | 1.41 |
| Insulin 5 mg/mL + 46 mg/mL PCIdelYVG + 6.4 mg/mL tail | 10.49 | 4.76 | 1.96 |
| Insulina 5 mg/mL + 6.4 mg/mL tail | 24.84 | 3.18 | 1.30 |

TABLE 12

Growth (Percentage in relation to the average of the controls)

| Treatment | Average | Standard Deviation | Standard Error |
|---|---|---|---|
| Control | 100 | 11.41 | 4.66 |
| IGF-1 20 ng/mL | 125.65 | 12.65 | 5.16 |
| IGF-1 20 ng/mL + 50 mg/mL wtPCI | 43.43 | 9.70 | 3.96 |
| IGF-1 20 ng/mL + 50 mg/mL wtPCI + 6.4 mg/mL tail | 15.09 | 3.51 | 1.43 |
| IGF-1 20 ng/mL + 46 mg/mL PCIdelYVG | 33.30 | 8.12 | 3.32 |
| IGF-1 20 ng/mL + 46 mg/mL PCIdelYVG + 6.4 mg/mL tail | 21.23 | 7.19 | 2.94 |
| IGF-I 20 ng/mL + 6.4 mg/mL tail | 17.35 | 3.95 | 1.61 |

From these data a Student's t test was carried out. The growth averages in each treatment were contrasted with the average of the controls. The result was that in presence of the growth factors (insulin and IGF-1) only a clear stimulation in relation to control is observed, 93% for the insulin and 26% for IGF-1 ($\alpha=0.001$), while for the case of the EGF alone, in the tested concentration, an inhibition of 36% ($\alpha=0.001$) is observed in relation to the control situation. For the treatments with combinations of wtPCI, PCIdelYVG or tail together with the EGF, a very important growth inhibition is observed in relation to the control situation ($\alpha=0.001$) which oscillates between 75 and 85%. This effect is maintained when a combined treatment of wtPCI or PCIdelYVG plus tail and EGF is used. The combined treatments with insulin prove to have equally strong inhibiting effects ($\alpha=0.001$) for any of them, in this case the inhibition oscillating between 75 and 90% in relation to the control situation. And finally, in the case of treatments combined with IGF-1, clear inhibiting effects are also observed ($\alpha$=0.001), the inhibition oscillating from 56 to 85% in relation to the control situation.

Figure 9A:
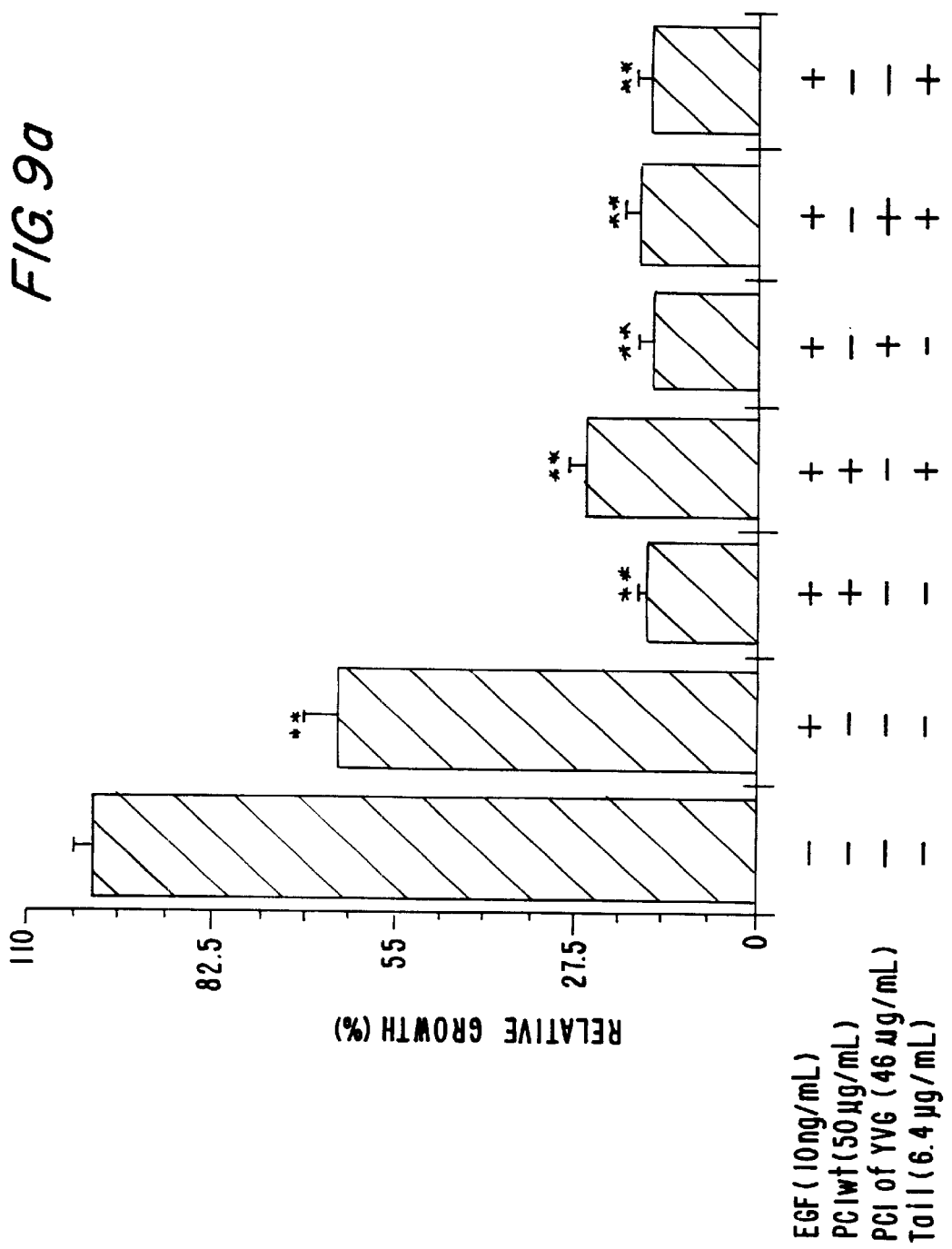
FIG. 9: Effect of the presence of growth factors alone or combined with wtPCI, PCIdelYVG or tail in the culture medium of the human pancreatic adenocarcinoma cell line Panc-1. The cells were cultivated in DMEM medium plus FBS for 48 h; after washing with PBS, the cells were cultivated for a further 48 h in DMEM without FBS. Afterwards, treatment in DMEM was carried out without FBS, plus sodium selenite, transferrin and BSA, with the growth factors and the PCI or variants for 72 h. a) Treatment with EGF alone or combined with PCI, PCIdelYVG and tail; b) treatment with insulin alone or combined with PCI, PCIdelYVG and tail, and c) treatment with IGF-1 alone or combined with PCI, PCIdelYVG and tail. For each treatment, 6 replicas were made. The data are indicated as a growth percentage in relation to the average of the controls (cells cultured in the absence of the factors object of the study). Bars indicate the standard error. $*p<0.005$, $**p<0.001$.
Figure 9C:
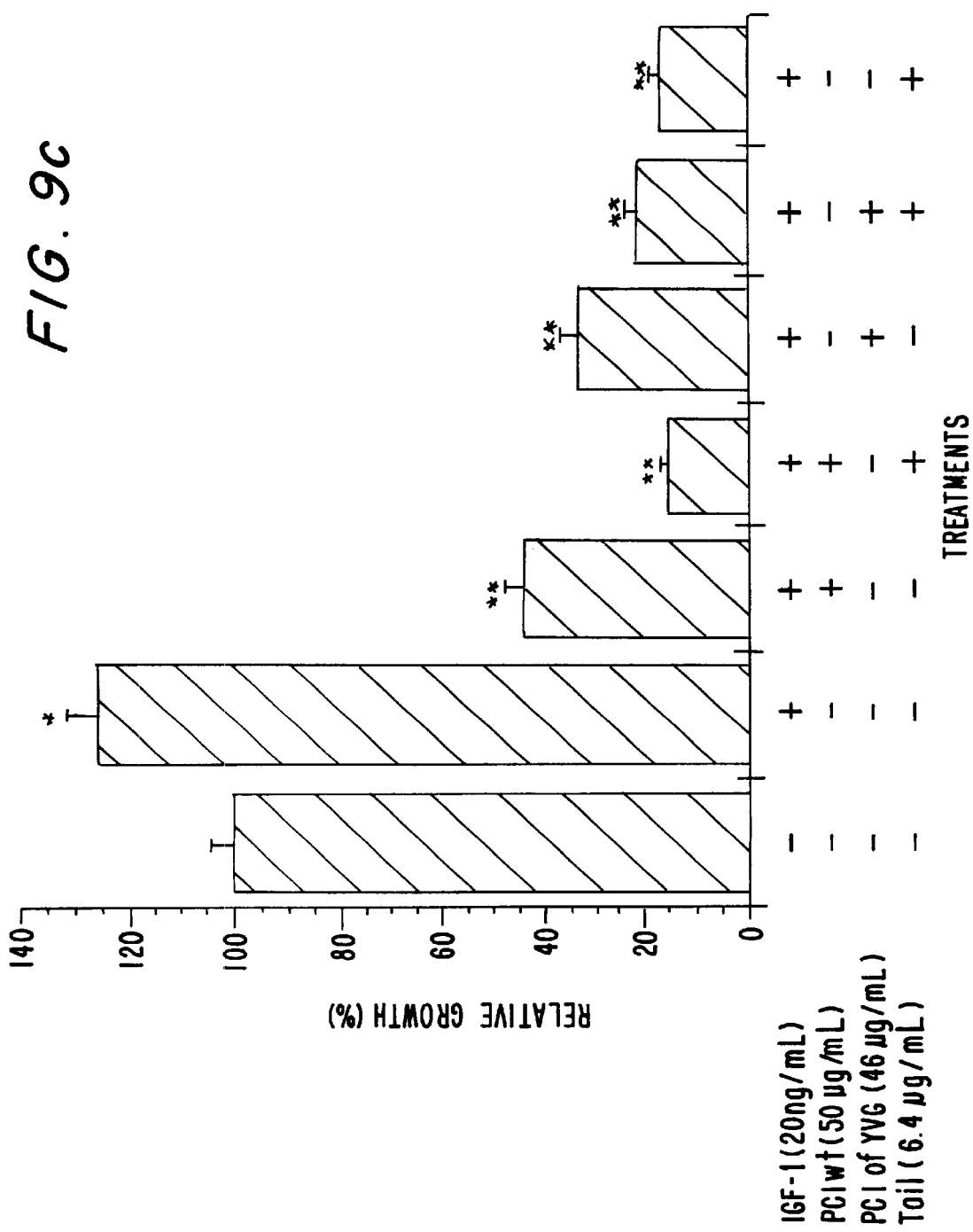

The data are graphically represented in FIG. 9. As we can observe, after 72 h of culture in SFM, the growth of the Capan-1 cells is clearly stimulated by the presence of insulin and IGF-1 in the medium, while the EGF produces an inhibition of the growth. The presence of wtPCI, PCIdelYVG, tail or combination with the tail in competition with the EGF, the insulin or the IGF-1, produces a clear decrease in cell growth.

4.B.3. Determination of the Growth Curve of the Cell Line Capan-1 in Presence or Absence of PCI The growth curve of the human pancreatic adenocarcinoma cell line Capan-1 was determined by culturing the cells in medium DMEM supplemented with 10% of FBS (see Section 4 ..B.1.). Plates with wells were used, each with a surface of 10 cm$^2$ (Nunc, Denmark). The number of cells initially placed per well was 1×10$^5$, and changes of medium were made every four days, adding new PCI in the medium in the case of the cells treated with PCI.

Figure 10:
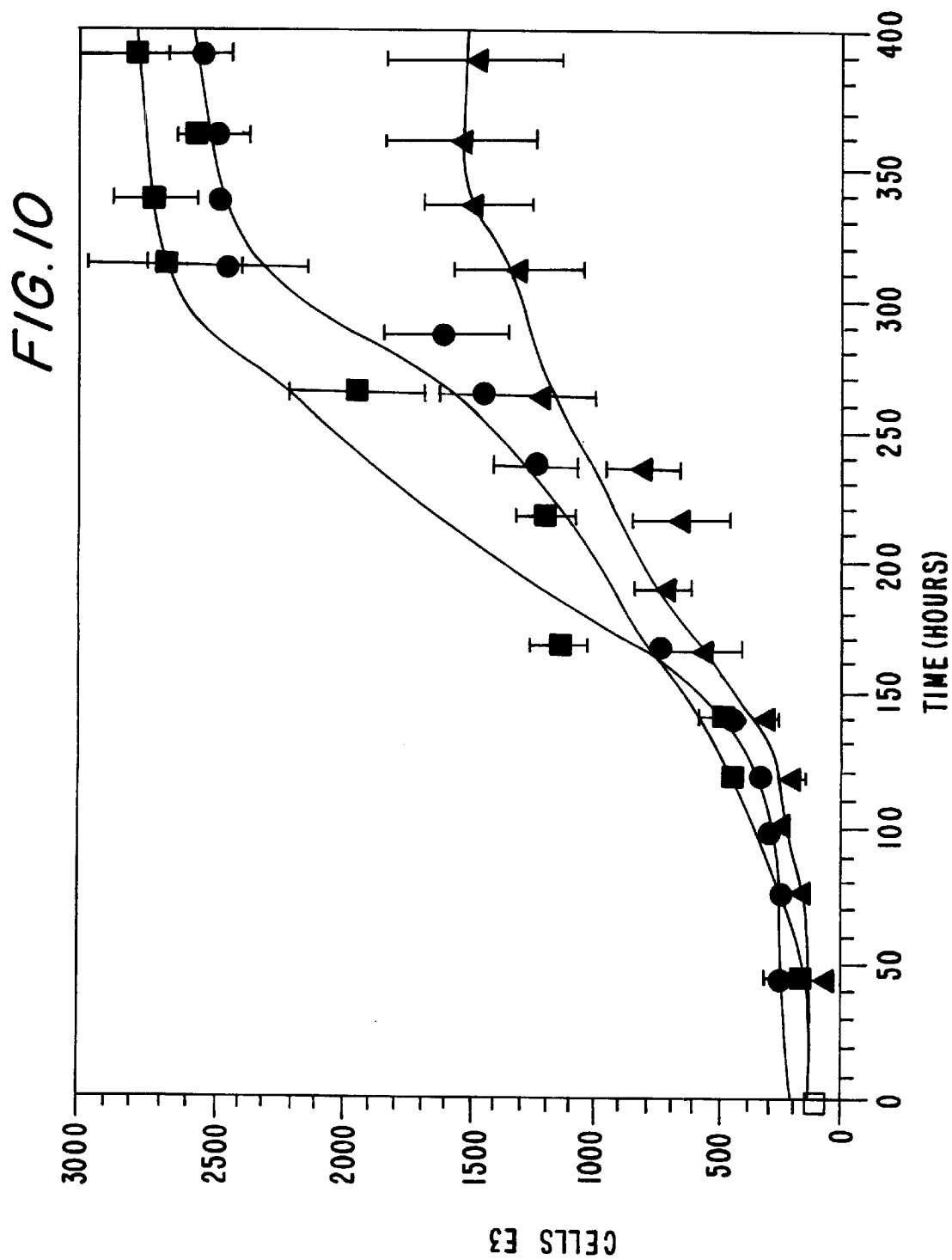
FIG. 10: Growth curves of the human pancreatic adenocarcinoma cell line Capan-I growing in DMEM supplemented with 10% FBS: control (circles), treated with 1 µg/mL of PCI (squares) and 10 µg/mL of PCI (triangles) added to the culture medium. The medium was changed every 4 days adding fresh PCI in each change in medium. Initially, $1 \times 10^5$ cells were seed in wells of 10 cm$^2$, in plates of 6 wells. Each point is the average of three measures. Bars show the standard error.

Three growth curves were determined (FIG. 10) in absence of PCI and in presence of PCI, in concentrations of 1 $\mu$g/mL and of 10 $\mu$g/mL. Initially, 45 replica-wells were placed for each treatment. After 15 days, three of the replica-wells of each treatment were taken and their number of cells counted by means of trypsinization and recount employing hemocytometer (for a description of the technique, see Section 4.B.1.). The results of the tests are shown in Table 13, which presents the duplication times calculated from the data.

TABLE 13

Cell duplication times in terms of the treatment with PCI

| Cells | Duplication time (h) |
|---|---|
| Control | 85 |
| Treated with 1 mg/mL | 90 |
| Treated with 10 mg/mL | 130 |

It can be seen that the cells treated with a concentration of 10 g/mL of PCI show a growth significantly slower than the growth of the control cells, clearly observable from 300 h onwards. In addition, the density reached by the stationary stage, that is to say, when the cells stop dividing, is significantly lower than in the control cells (approximately, a half). In relation to the cells treated with 1 $\mu$g/mL of PCI, for some reason they seem to grow more quickly than the control cells but reach the stationary stage with a similar density.

4.B.4. Studies on the Pretreatment with PCI on Cell Growth

Various experiments have been carried out to study the effect of the prolonged treatment with PCI on the growth of the tumoral cell lines. The general conclusion of such studies is that in the analysed lines, the treatment with PCI for over 15 days has a strong inhibiting effect on their growth. Such an effect being maintained even when the PCI is removed from the medium.

The analysed cell lines were Capan-1, already described, and Int-2. This latter being a murine insulinoma cell line derived from transgenic mice developed in the lab of Dr. M. Frazier. The medium employed for the growth of both lines was DMEM+10%FBS and the culture techniques that were used were identical to those previously described.

In the case of the Capan-1 cell line, two different tests and which are described as follows were carried out:

a) Proliferation Tests:

1. 5,000 cells were seed in 2 wells of a plate of 12 wells. One of the wells was grown with medium (non-pretreated cells), and the other with medium with 50 $\mu$g/mL of PCI (pretreated cells). The cells were kept in such conditions for the period of time that is indicated in the results section as time of pretreatment.

2. Twice a week, the medium of the wells was replaced by fresh medium with or without PCI, and each time that in any of the wells confluence was reached, the cells were trypsinized and ¹/₁₀ of them was placed again in the original well, the other cells being discarded or frozen.

3. Once the desired time of pretreatment elapsed, the cells were trypsinized and counted, being employed to start proliferation tests such as those described in Section 4.B.2.1. The number of cells that was placed per well in the proliferation plate (of 96 wells) was 2,000, 7 replicas being put for each treatment. The cells underwent treatment with or without various PCI concentrations.

4. Once the treatment time elapsed, the number of cells per well was estimated as previously described in Section 4.B.2.a.

b) Growth Curves

The growth curves were made for the Capan-1 cells pretreated with PCI, as well as for those non-pretreated cells. The protocol employed was identical to that described for proliferation tests, with the peculiarity that they were placed the same day, the same cells employing five different plates with 96 wells that were covered at 3, 6, 9, 13 and 17 days.

In the case of the Int-2 cell line, only proliferation tests were performed. They were carried out in the same way as that described in the case of Capan-1, with the unique difference that the number of cells that was put per well in the plate of 96 was 500 instead of 2,000.

Figure 11A:
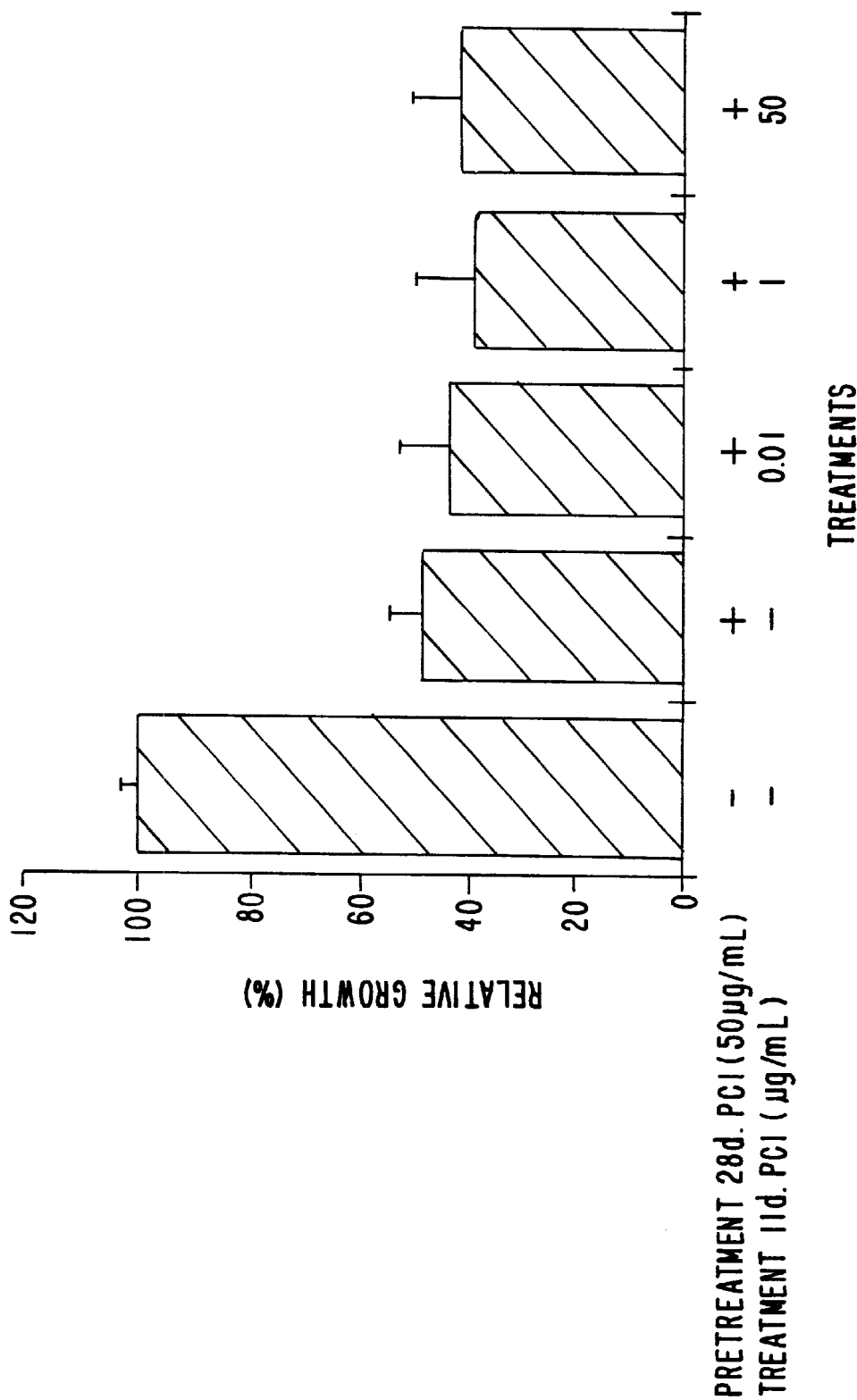
FIGS. 11A 11B and 11C: Proliferation of the cell line Capan-1 pretreated with PCI. The number of cells is expressed in relation to the number of not pretreated control cells (cultivated without PCI in the pretreatment). The pretreatment in all cases is of 50 µg/mL of PCI. The result of three experiments is presented.
Figure 11B:
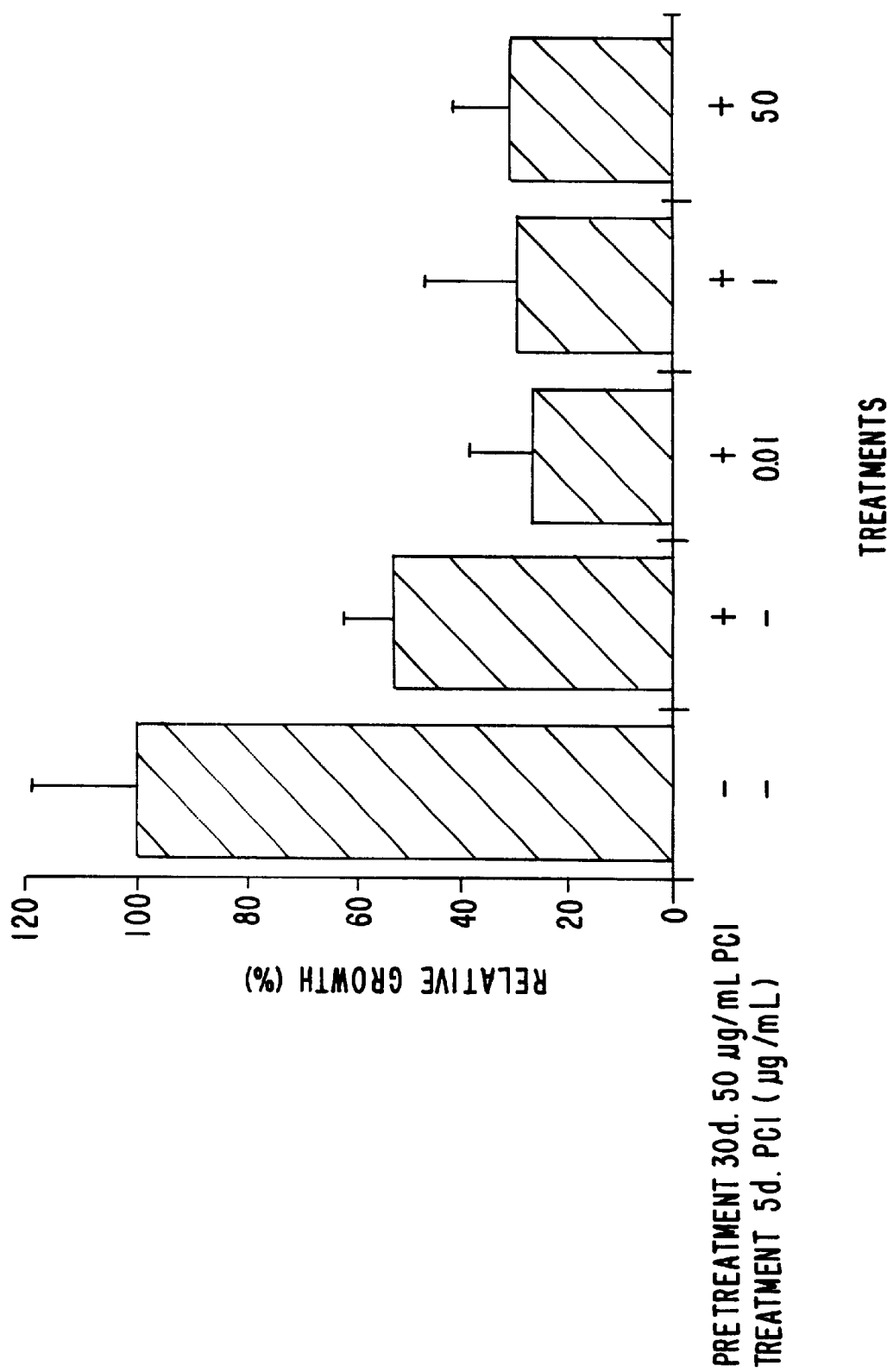
Figure 11C:
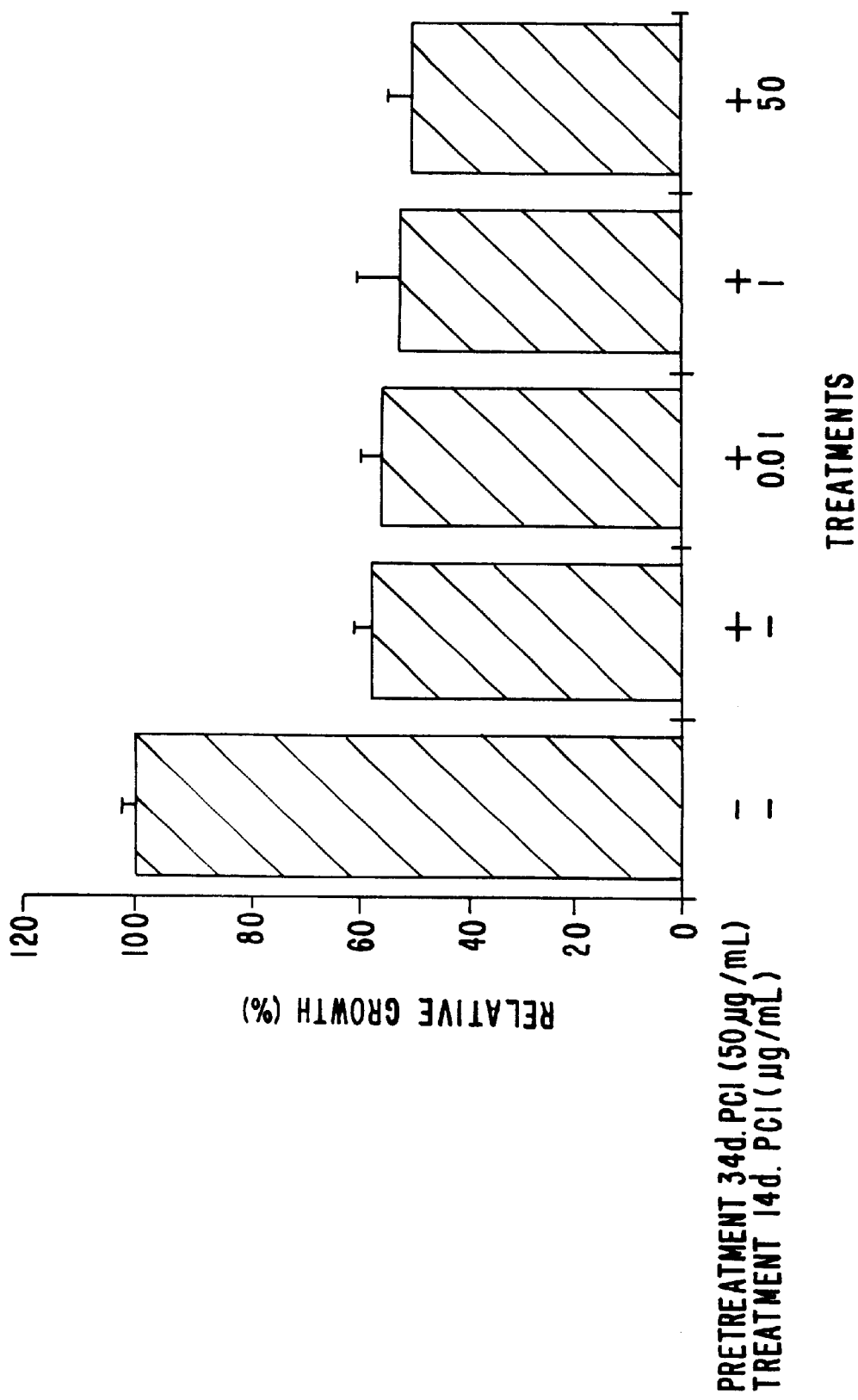

FIGS. 11A–11C shows the result of the three proliferation tests carried out with the Capan-1 cell line. In one of them, pretreatment was extended to 28 days and treatment took 11 days, in the other 34 and 18 days, and in the other 30 and 5 days. The results obtained in all the cases were similar. The final number of cells in the wells where pretreated cells were placed and which were cultivated afterwards in absence of PCI is approximately half that of those in the wells with non-pretreated cells cultivated in the same medium. In the wells in which the PCI was maintained in the medium, the growth of the pretreated cells somehow resulted even inferior to that observed in the absence of PCI.

Figure 12:
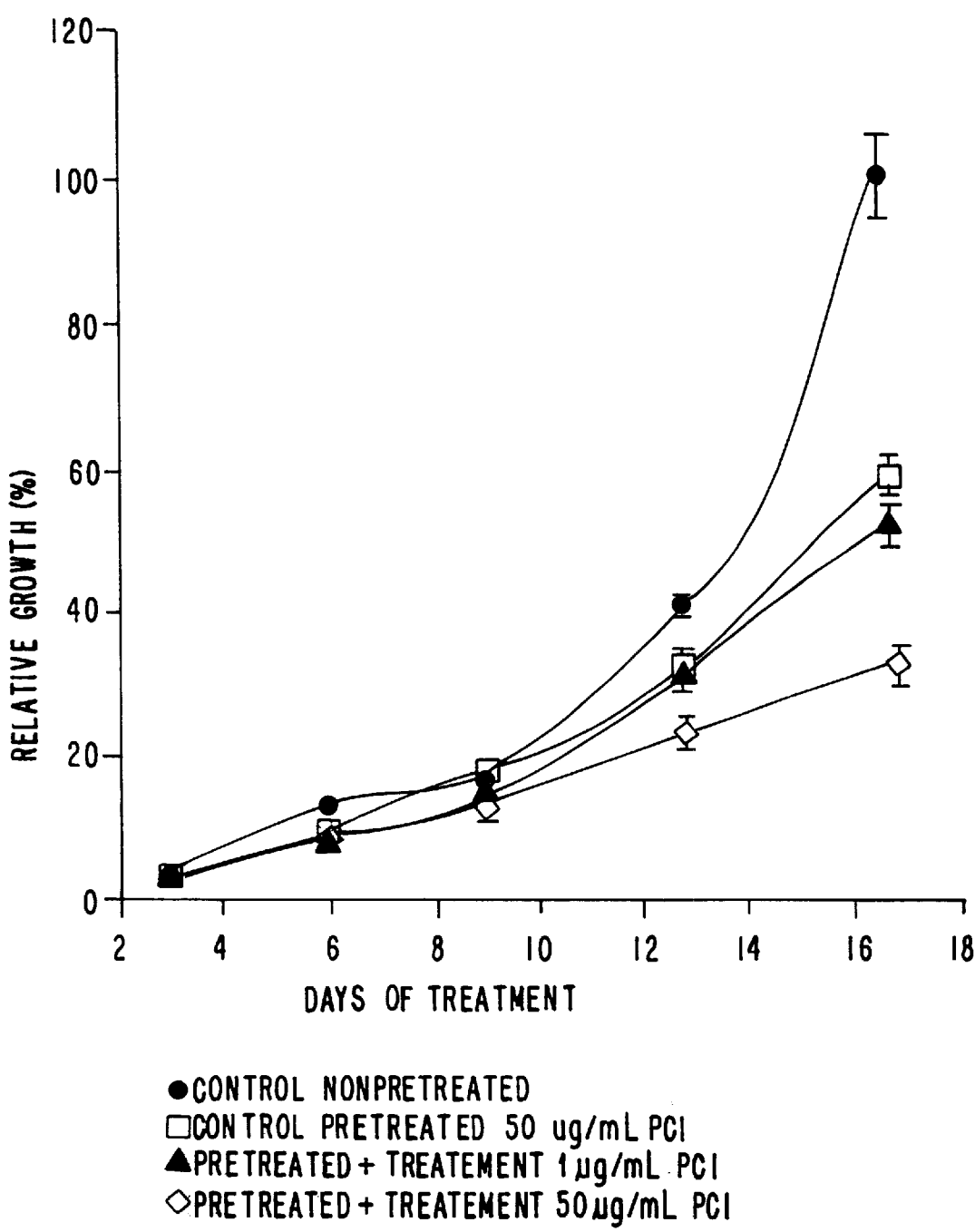
FIG. 12: Growth curve of Capan-1 cells pretreated and not pretreated with PCI. The number of cells is expressed in relation to the final number of control cells not pretreated (cultivated without PCI in the pretreatment). The pretreatment in all cases is 50 µg/mL of PCI. Bars indicate the average of the number of cells in 8 wells and the vertical line, the standard error.

These results led us to carry out a new series of experiments with the aim of obtaining a growth curve for the pretreated cells Capan-1 (over 43 days) and for the non-pretreated with PCI, a curve that is presented in FIG. 12. As we may clearly observe, the growth of the cells pretreated in absence of PCI is much slower than that of the non-pretreated cells, the difference becoming clearly significant after 13 days of culture. The pretreated cells maintained in the presence of PCI showed an even slower growth rate.

The conclusion that may be derived from these tests is that the cells cultivated for at least 28 days with PCI (at a concentration of 50 $\mu$g/mL) grow much more slowly than the control cells, even if the PCI is taken out of the medium. In other words, in the long run the treatment with PCI for at least 4 weeks seems to have an inhibitory effect on the cell growth, an effect which is maintained even if the protein is removed from the medium.

Figure 13A:
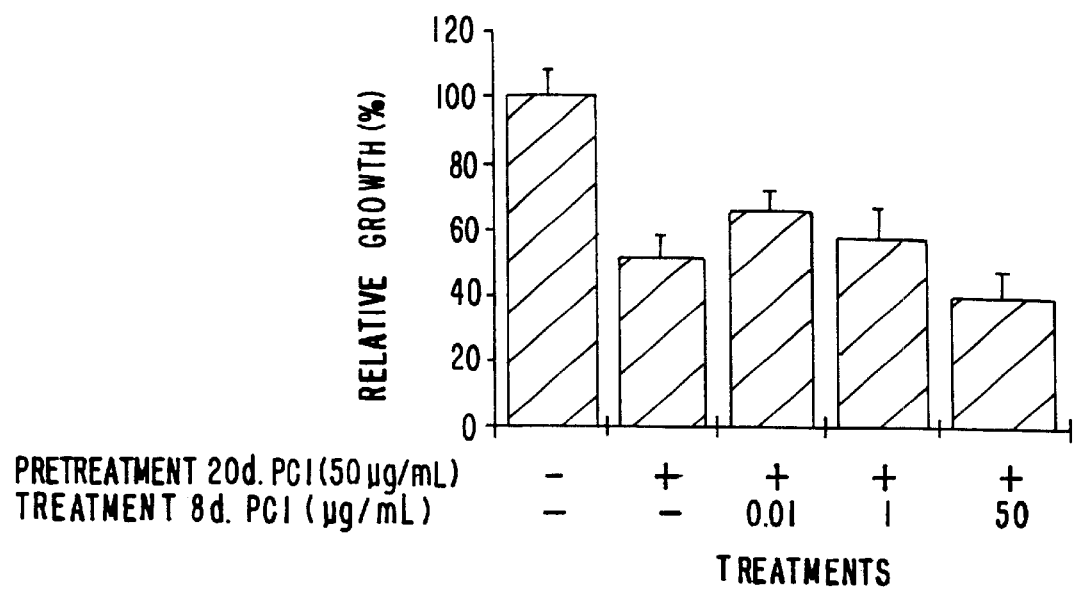
FIG. 13: Proliferation of the cell line Int-2 pretreated with PCI. The number of cells is expressed in relation to the final number of control cells not pretreated (cultivated without PCI in the pretreatment). The pretreatment in all cases is 50 µg/mL of PCI. The result of three experiments is presented: (a) pretreatment, 13 days, treatment, 7 days; (b) pretreatment, 20 days, treatment, 8 days, and (c) pretreatment, 30 days, treatment, 5 days. Bars indicate the average of the number of cells in 8 wells and the vertical line, the standard error.
Figure 13B:
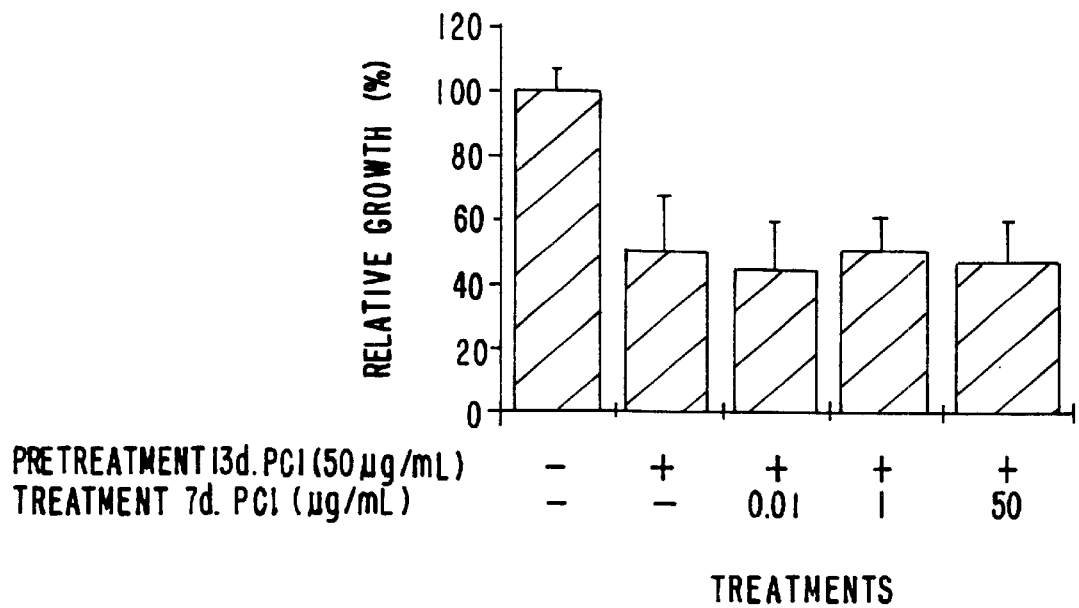
Figure 13C:
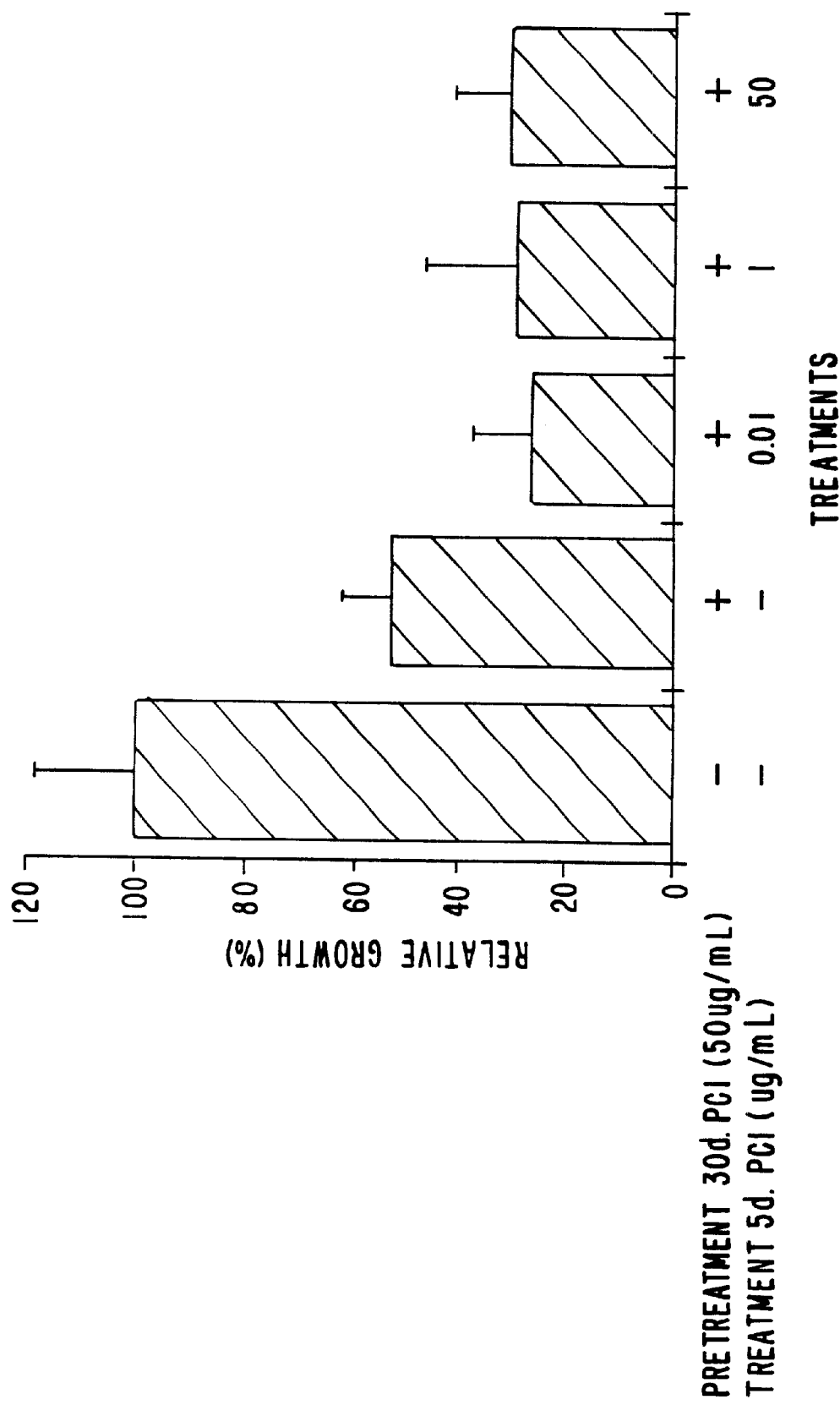

In FIG. 13 we can see the results of the proliferation tests carried out with the Int-2 cell line which are very similar to those obtained in the case of Capan-1. Three different tests with various kinds of pretreatment and treatment were carried out. The pretreatments were of 7, 20 and 30 days and the corresponding treatments were of 7, 8 and 5 days. As happened with Capan-1, the Int-2 cells pretreated with PCI and cultured later on in the absence of the protein show a much more inferior growth, approximately half compared to that of the non-pretreated cells. If the PCI is maintained in the culture medium, the rate of growth of the pretreated cells is even more reduced, the longer the treatment, the more important the effect. Therefore, the observed long-term inhibiting effect of the treatment with PCI in the case of Capan-1 also takes place in the Int-2 cell line, its magnitude being very similar.

4.C. Metastasis Inhibition

4.C.1. In vitro Invasiveness Assays

In order to study the possible influence of PCI in the invasive and metastatic capacity of the tumoral cells, we have analysed the migration of the cells through a membrane of Matrigel© in presence or absence of PCI.

The material, media and solutions employed in this experiment were the following:

Invasion chambers BIOCOAT©, MATRIGEL©, (Becton Dickinson Labware, Bedford).

Basic medium DMEM (Sebak, Fontlab, Germany).

Full medium with 10% of bovine fetal serum (FBS) (DMEM+10%FBS): it is prepared by mixing 200 mL of DMEM, 1 mL of 100 mM pyruvate solution, 0.2 mL of 50 mg/mL gentamicin solution and 20 mL of FBS.

Culture plates with 24 wells.

Delafield hematoxylin: firstly, the solutions A (4 g Hematoxylin, 25 mL of absolute alcohol) and B (40 g ammonium aluminium sulphate in 400 mL of distilled $H_2O$) are prepared. Once mixed and after 4 or 5 days, they are filtered and 100 mL glycerine and 100 mL of methyl alcohol are added. 4 o 5 days later, it is filtered and it is ready for use.

Chlorhydric water: 1 mL HCl 1N, 199 mL distilled $H_2O$.

Eosine: 1 g eosine in 100 mL of distilled $H_2O$. Once prepared, some drops of acetic acid are added.

Alcohol 96°.

Assemble medium (Merck, Germany).

Laminar flux culture cabinet (Telstar, Germany).

Inverted microscope of phases' contrast (Zeiss, Germany).

Optical microscope.

Incubator with water mantle (Forma Scientific, USA).

In this test, with the aim of determining whether the PCI causes some difference in the invasive capacity of tumoral cells in vitro, the number of cells which had migrated through a membrane of Matrigel© in presence or absence of PCI in the culture medium was determined. The detailed protocol is as follows:

1. The wells of Matrigel© which are going to be employed are placed at room temperature on an empty plate of 24.

2. The wells are hydrated by adding 250 µg/mL of tempered full medium and kept for 1.5–2.0 h.

3. After the hydration, take the medium carefully out of the wells; later on, 200,000 cells are added to two wells, respectively. In one of them, we will add the medium in which the cells grow and in the other, medium with PCI.

4. After 17 h of culture in an incubator at 37° C., 90% of relative humidity and 5% of $CO_2$, the samples are processed as follows:

4.1. Wash the cells on the filter with a small stick.
4.2. Wash in distilled $H_2O$.
4.3. Dye with the solution of hematoxylin for 12 min.
4.4. Wash again with distilled $H_2O$.
4.5. Submerge for 1–2 seconds in chlorhydric water.
4.6. Wash with distilled $H_2O$.
4.7. Dye with eosine solution for 6 min.
4.8. Wash with distilled $H_2O$.
4.9. Submerge in alcohol of 96° for 10 min.
4.10. Set up on the slide with the assemble medium.
4.11. Look at the microscope and count the number of cells that have migrated through the Matrigel filter.

The invasiveness tests in vitro were carried out with the mouse melanoma B16HM cell line selected as previously described (Barberàr-Guillem, E. et al. (1988) *Invasion Metastasis*, 8: 266–284). The wells were placed with medium in absence of PCI (control) and in presence of PCI, at a concentration of 50 µg/mL. We observed that, in the control case, 29 cells passed through the membrane; 110 cells treated with PCI passed through the same as well. Therefore, it is observed that the PCI, in this concentration, stimulates the migration 3.5 times more compared to the control case without PCI.

4.C.2. Metastasis tests in vivo

In order to study the effect of the PCI on the metastatic capacity of the tumoral cells, mouse melanoma B16 cell line are used used because this line is singeneic with the mice. These cells, intrasplenically inoculated in singeneic mice, after 7 days, start to develop metastasis in the liver of the mouse. The following material was employed:

Reagents and required material for cell culture such as that described in Section 4.B.1.

Surgical material required for carrying out an incision and stitching.

Nembutal: anaesthetic which is administered in a dose of 50 mg/kg.

Alpha MEM Hepes (Gibco, USA).

Male mice C57BL/6J of 6 to 8 weeks (IFFA Credo, France).

PBS buffer. Its composition is the following: 140 mM NaCl; 7.5 mM $Na_2HPO_4$; 2.5 mM $NaH_2PO_4$. Its pH is adjusted to 7.5 with NaOH or phosphoric acid.

Formalin 10%.

Solutions of hematoxylin-eosine (Section 4.C.1.).

Ultramicrotome.

Optical microscope.

Various treatments were studied. They are detailed as follows:

A control group: consisting of 5 mice to which 300,000 cells dissolved in 0.1 mL of alphaMEM-Hepes were inoculated. The mice, previously anaesthetized with nembutal, were inoculated by way of intrasplenic injection, by means of a little incision and subsequently closed with stitches. These mice were killed 11 days after injection of the tumoral cells by cervical dislocation.

Treatment 1: again, 5 mice were inoculated in the same way as those of the control group. Six days after the injection, a daily treatment with 0.1 mg/mL of PCI in 0.1, mL of PBS by way of intraperitoneal injection was started. The animals were also killed on the eleventh day after the injection.

Treatment 2: in this case, the cells inoculated to the mice (also 5 of them) were previously treated in vitro for 4 days in a concentration of 0.1 mg/mL of PCI. The inoculation of the cells and the posterior killing of the mice was identical to that of the control group.

Once killed, their liver was extracted. It was then fixed with a formalin solution at 10% and sections were obtained by employing the ultramicrotome. Afterwards, the sections were dyed with hematoxyline-eosine and the number of metastatic focuses was counted.

As the recount of metastatic focuses was carried out, we found that, for the control group, there was an average of 32±7 focuses, for the mice of treatment 1 there were 27±focuses, and for the mice of treatment 2, the number of focuses was 4±1; thus we observed a clear decrease in the metastatic capacity of the cells pretreated with PCI.

4.D. Tests with Athymic Mice

With the aim of evaluating the sensitivity to PCI of induced human tumors, studies were carried out with nude mice. Human pancreatic adenocarcinoma cells Capan-1 were inoculated in these mice subcutaneously and once the tumor reached a minimum size of 3×3 mm2, a daily treatment begun, also subcutaneous, with different doses of PCI for 32 days. The following materials were employed:

Reagents and material required for cell culture such as described in Section 4.B.1.

Nude mice, CD-1 nude/females six weeks old.

Syringes of insulin (Becton Dickinson Labware, Bedford).

Metaphane (anaesthetic).

PBS buffer. Its composition is the following. 140 mM NaCl; 7.5 mM $Na_2HPO_4$; 2.5 mM $NaH_2PO_4$. Its pH is adjusted to 7.5 with NaOH or phosphoric acid.

Vernier calibrator.

In order to determine whether the PCI had any effect on tumoral growth, the growth of subcutaneous tumors induced in nude mice, whether treated with PCI or not, was followed over a period of time. The detailed protocol was the following:

1. $10^7$ Capan-1 cells were dissolved in 100 $\mu$L of DMEM and injected subcutaneously to the mice. 19 mice were inoculated and divided into 4 groups.

Control group: consisting of 5 mice. They were treated with PBS.

Group 1: also consisting of 5 mice. They were treated with 0.11 mg/mL of PCI dissolved in PBS.

Group 2: consisting of 5 mice to which a treatment with a dose of 0.6 mg/mL of PCI was applied.

Group 3: consisting of 4 mice for which, in this case, the dose of PCI was 1.2 mg/mL of PCI.

2. 12 days after the inoculation of the cells, the daily treatment with PBS or PCI by direct injection in the tumor of 100 $\mu$L of such solutions was started. At this moment, the tumors were palpable and measured, at least, 2 mm of diameter.

3. During the treatment, the size of the tumor was determined every two days using a Vernier calibrator which made it possible to measure the size of the tumor in all its dimensions. The volume of the tumor was determined by means of the following formula:

$$V = \frac{W^2 \times L}{2}$$

where W is the width of the tumor and L the length.

As the volumes of the tumors became known, the relative growth of such tumors was calculated every 7 days using the following formula:

Relative volume =

$$\frac{\text{Volume of the tumor at time } t \text{ of the treatment}}{\text{Volume in relation to time 0 of the beginning of the treatment}}$$

Once the treatment had finished, the duplication time of the tumor (td) was calculated for each treatment with the following formula:

$$t_d = \frac{2 \times d}{V_t - V_0}$$

where d corresponds to the days of treatment, $V_t$ to the volume of the tumor at the end of the treatment and $V_0$ to the volume at the beginning of the treatment.

Figure 14:
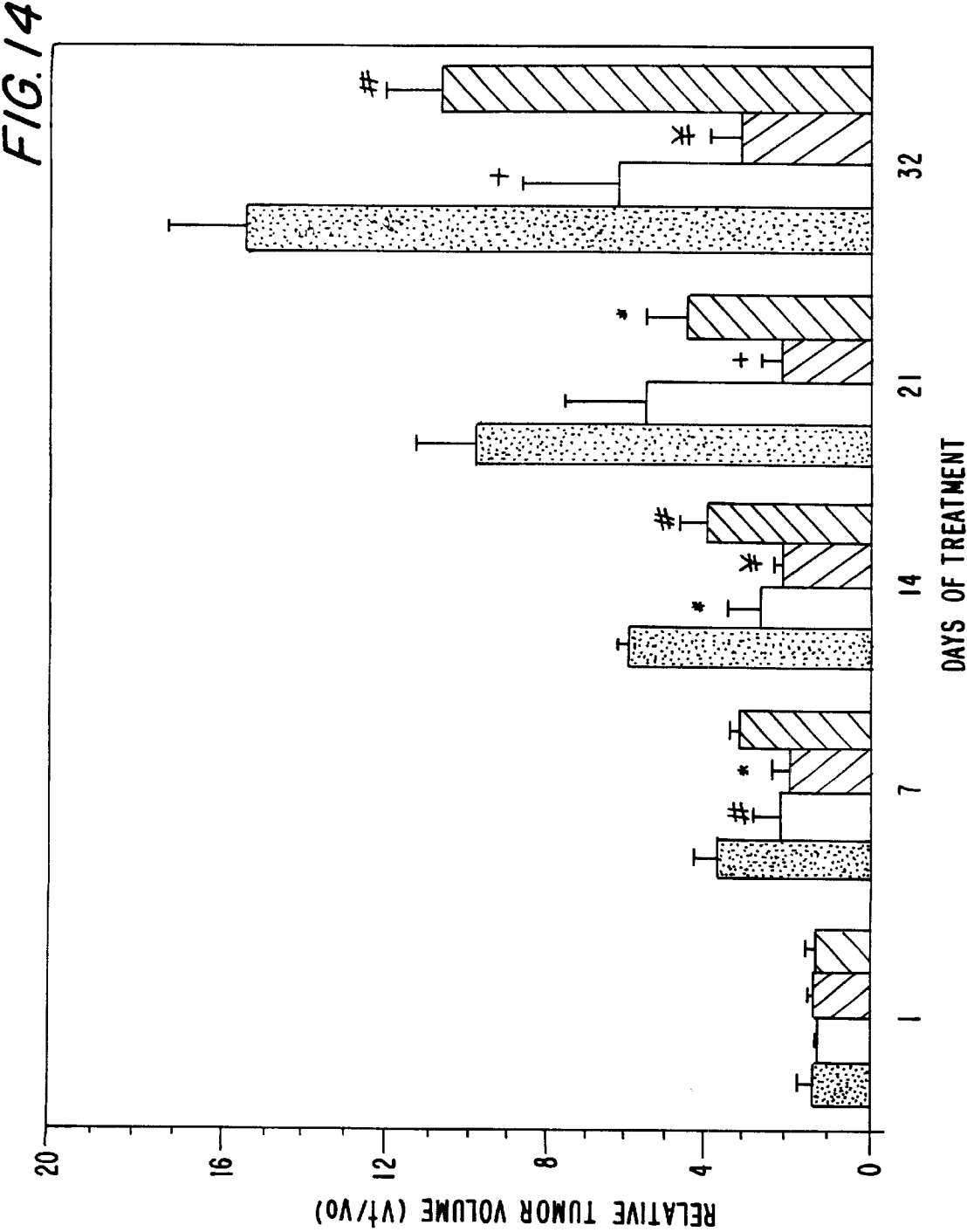
FIG. 14: Effect of the PCI on the tumoral growth in mice. The tumors are induced in nude mice by subcutaneous injection of $10^7$ cells of the human pancreatic adenocarcinoma cell line Capan-1. 12 days after the injection of the cells it is started the daily treatment with phosphate buffer (PBS) or PCI by directly injecting the tumor. The size of the tumor is measured every 2 days using a vernier calibrator. In the graph, the relative volume is represented at various stages of the treatment for the control (first column, starting from the left), and for the groups treated with various doses of PCI: 0.11 mg/mL, 0.6 mg/mL and 1.2 mg/mL which are represented in the columns consecutive to the control column. The data represent the average of the 5 mice. Bars indicate the standard error. The statistic value is represented as: #$P<0.1$, *$P<0.025$, +$P<0.01$ and ¥$P<0.001$ versus the control for a Student's t.

The effect of the PCI on the tumoral growth of the human pancreatic adenocarcinoma cell line Capan-1 was measured after 32 days of treatment of the tumors induced in the nude mice. This effect being determined by comparing the relative growth of the tumors of the control mice in relation to that of the mice treated with various doses of PCI. The results obtained are represented in FIG. 14. From these data a Student's t test was carried out. The averages of growth in relation to each dose of PCI were contrasted with the control groups.

According to such results, we may conclude that, from the beginning of the treatment, differences were already observed in the growth of the treated tumors compared to the controls. These differences were very clear at the end of the treatment for the three tested doses. The dose with the highest level of significance for the test carried out was 0.6 mg/mL, with a level of confidence of over 99.9%, followed by the dose of 0.11 mg/mL with a confidence level of over 99% and, finally, the dose of 1.2 mg/mL with a level of confidence of over 90%.

Also from the volumes of the tumors, the duplication times of the tumor for the various treatments were calculated. The results obtained are presented in Table 14, where the average and the standard error of the duplication time for the five mice of each group is expressed.

TABLE 14

Duplication times of the tumor according to the treatment

| Treatment | Duplication time (days) | Standard error |
|---|---|---|
| Control | 4.32 | 0.68 |
| 0.11 mg/mL PCI | 9.06 | 1.99 |
| 0.6 mg/mL PCI | 19.49 | 3.02 |
| 1.2 mg/mL PCI | 5.78 | 0.61 |

Also, from these data, the same contrast of hypothesis was made as that of the relative volumes. The result was that for the two doses in which the variation in relative volume had appeared as most significant, that is to say, 0.6 mg/mL and 0.11 mg/mL, the averages of the duplication time were significantly different from the control average with a very high level of significance (concretely, lower than 0.005 for the dose of 0.6 mg/mL and lower than 0.1 for the dose of 0.11 mg/mL). Therefore, it may be concluded that the PCI significantly increases, in some concentrations, the duplication time of the tumors.

Figure 15:
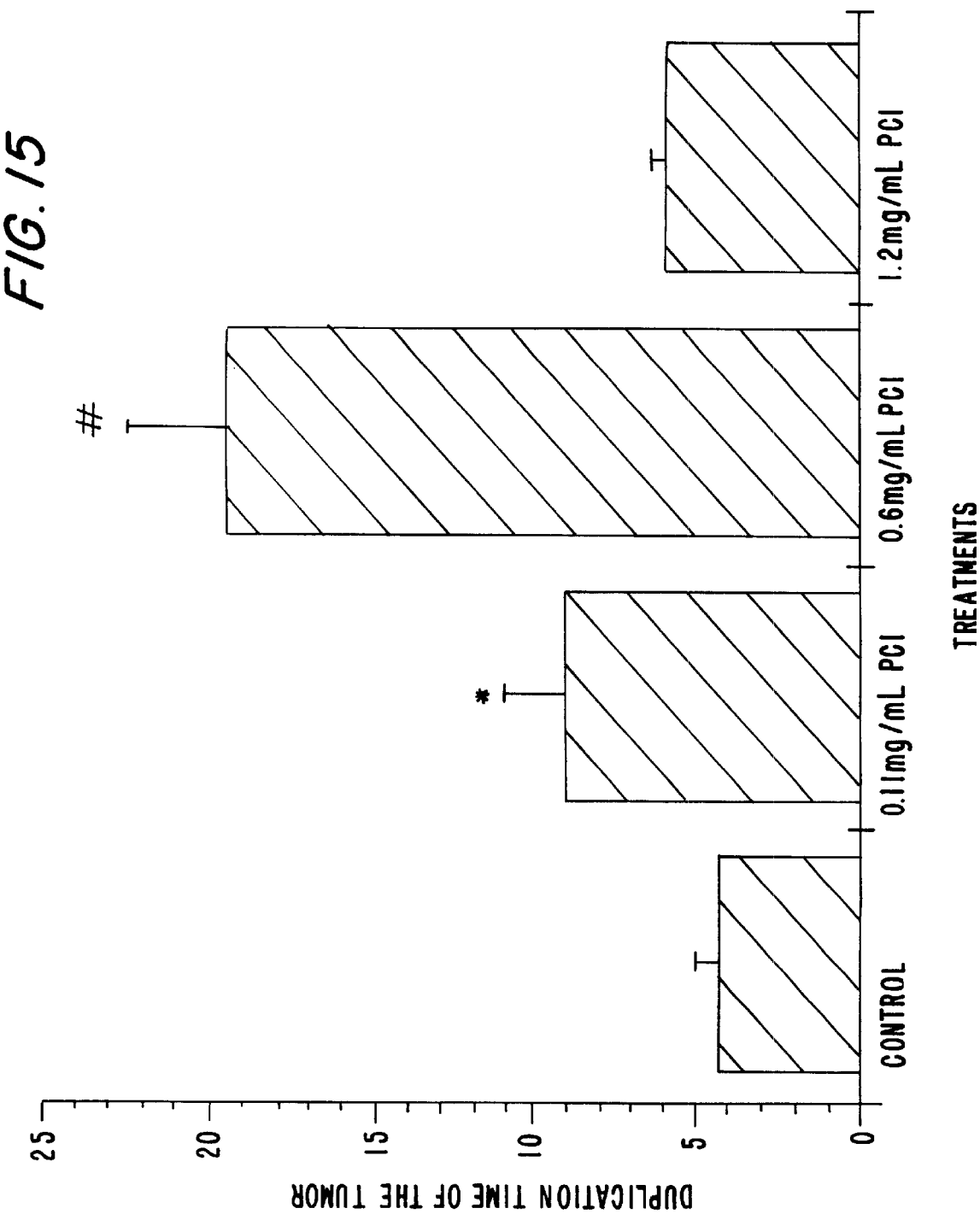
FIG. 15: Effect of the PCI on the tumoral growth, in mice, according to the experiment described in the previous figure. The duplication times were calculated from the volume of the tumors. The data represent the average ±SEM, n=5. *$P<0.1$ and #$P<0.005$ compared to the control in a test of Student's t.

The data are graphically represented in FIG. 15. As we can observe, the duplication time of the tumor when it is treated with a dose of 0.11 mg/mL of PCI is twice as high as that of the control tumors and, for doses of 0.6 mg/mL, the effect is much higher, the duplication time being 4.5 times higher than that of the control group.

Table 15 presents a summary of all the results obtained from the tests with nude mice. Thus, it may be concluded that the tumors produced by the inoculation of the human pancreatic adenocarcinoma Capan-1 cell line in nude mice when they are treated with a dose of PCI of 0.6 mg/mL, appears to have a significant activity in the reduction of the growth of such tumors; also, the dose of 0.11 mg/mL shows a moderate activity.

During the treatment it was observed that, in the process of injection, the tumors of the control animals bled three days after initiating the treatment; on the other hand, the tumors of the animals treated with PCI took 8 days to start bleeding.

TABLE 15

Activity of the PCI in "human tumor xenografts"

| | | | administration | | s.c. |
|---|---|---|---|---|---|
| Tumoral line | Histologic type | Treatment Drug (days)[a] | Dose (mg/kg/day) | Optimal T/C %[b] | SGD[c] |
| Capan-1 | Pancreatic Adeno- carcinoma | PCI 0–32 | 0.55 | 39.79 | 1.09(+) |
| | | | 3 | 21.36 | 3.51(+++) |
| | | | 6 | 69.4 | 0.34(−) |

[a]The treatment started 12 days after the inoculation of the tumor cells and the mice were treated daily for 32 days.
[b]The values of T/C were determined after finalizing the treatment. T/C = (average Vt/V0 treated/average Vt/V0 control) × 100. T/C < 50% moderate activity; T/C < 25%, significant activity.
[c]Td treated- Td control/Td control (Td, duplication time of the tumor). SGD < 1 expressed as −; >expressed +; and <3 expressed as +++

The control tumors maintained a quite reddish appearance throughout the test, while those treated with PCI never reached such tonality. What is more, we also have to emphasize the fact that the control tumors always had a great consistency which they maintained throughout the test, while those treated with PCI never reached such consistency. As the treatment went on, the skin surrounding the treated tumors lost its capacity to retain liquid, the supply of PCI resulting increasingly difficult. The previous verifications indicate clearly that the treatment had an effect on the process of neo-vascularization and of angiogenesis and, according to Folkman, M. D. (1995) *New England J. Med.,* 33: 1757–1763, an antiangiogenic therapy in mice causes a decrease in the interstitial pressure with the consequent decrease in the compaction (consistency) of the tumoral mass.

4.E. Cytotoxicity

With the aim of establishing whether the growth inhibitory effect of the PCI is due to the fact that it induces cytotoxicity in a unspecific way, or whether, contrarily, the effect is specific, originated by the alteration of some cellular processes, an in vitro cytotoxicity test of the PCI using the human pancreatic adenocarcinoma cell line Capan-1 was carried out with a wide range of PCI concentrations.

Besides the material described in Section 4.B.1. required for cell culture, in this experiment, the materials and solutions required for the cytotoxicity test were the following:

Culture plates of 24 wells (Nunc, Denmark).
BCECF-AM (2′,7′-bis-(2-carboxy-ethyl)-5-(6) carboxyfluorescein, aminoxy- methyl ester), is prepared by resuspending 100 $\mu$g of such reagent in 10 $\mu$l of DMSO. Then they are added to 12 mL of medium (DMEM+0°%BMS) (Molecular Probes, Inc., USA).
Propydium iodure (Boehringer Mannheim, Germany).
CytoFluor 2300/2350 Fluorescence Measurement System (Millipore, USA).

The cytotoxicity test is based on the use of two fluorophores, BCECF-AM and propydium iodure. The first one is employed to mark the viable cells because it quickly penetrates into the cellular cytoplasm where it is fragmented by the action of the esterases, becoming a fluorescent molecule. These esterases only being active when the cells are alive. Propydium iodine is a derivative of the phenanthrene which specifically joins the polynucleotide structure of nucleic acids intercalating between their pairs of bases. Due to its ionic structure it cannot penetrate into the live cells but it can do so into the dead ones, labeling DNA and RNA. Thus, the fundament of the test is to bring into contact the cells with PCI and to follow their viability and mortality rate over a 24 hour period; it is considered that a product is cytotoxic if, at a specific concentration, in this period of time, it produces a decrease in the viability rate in relation to the control cells (not treated with such product) which implies an increase in the mortality rate. The procedure that was followed was:

In a plate with 24 wells, 160,000 cells of the human pancreatic adenocarcinoma cell line Capan-1 were placed in each one. They were left in the incubator for 24 h, a period of time long enough for the cells to be completely adhered to the surface and, at this moment, the test started.

1. The absorbancy of the plate was read using cytofluor. The cytofluor is a fluorometer especially designed for reading the fluorescence of the cells; it is controlled by computer which makes it possible to employ various filter combinations of excitation-emission at the same time. In our case, a filter of excitation of 485 nm and another one of emission of 530 and 645 nm were employed. These filters allow us to detect the fluorescence of the two reagents employed for the cytotoxicity test such as BCECF-AM and propydium iodide. This first reading corresponds to the self-fluorescence of the cells, which it will later be deducted from the final value of the fluorescence.

2. Next, the cells were incubated with the BCECF-AM for 30 min at 37° C. The amount of BCECF-AM that was added to each well was 500 $\mu$L of the solution described in the material section.

3. Afterwards, the absorbancy of the plate was read. This measure corresponds to the total fluorescence.

4. We washed the plate, twice, with medium (DMEM+ 10% BMS). Thus, we eliminated the fluorescence that had not been incorporated by the cells.

5. 200 $\mu$L of medium were added to each well with the various concentrations of PCI to be tested and quadruplicates of each tested concentration were carried out. In our case, they were of 0.10 $\mu$g/mL, 30 $\mu$g/mL, 45 $\mu$g/mL, 60 $\mu$g/mL, 75 $\mu$g/mL. At the same time, 50 $\mu$L of propydium iodure were added to each well in order to have a 2 $\mu$M final concentration of such product.

6. Reading of the plate. This reading corresponds to time 0 and, from this moment, readings were carried out every half hour while the test lasted.

Once all the values of intensity of fluorescence (i.f.) at the various times had been obtained, the real value of fluorescence due to the BCECF-AM and propydium iodure was calculated using the following formula:

*I.F.=i.f.* at a specific time–*i.f.* self-fluorescence of the cells

Figure 16:
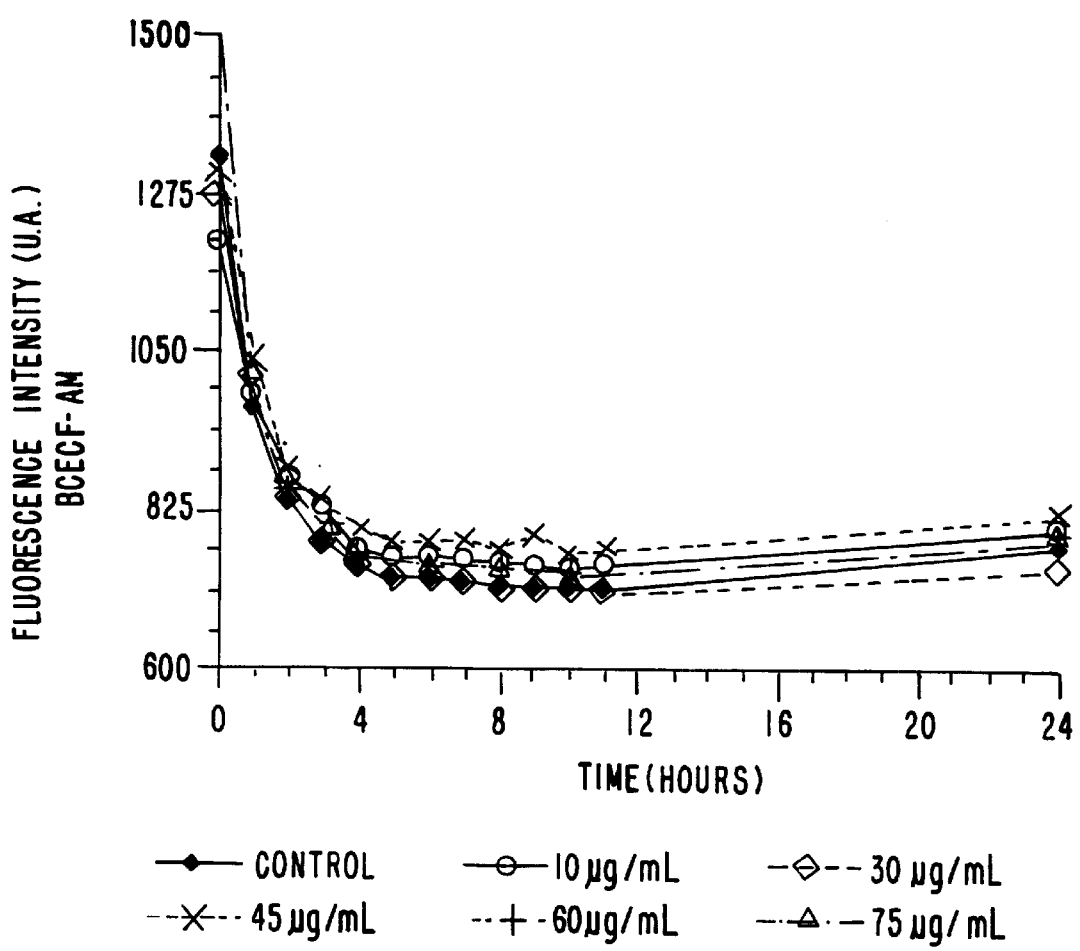
FIG. 16: Test of cytotoxicity of the PCI on the human pancreatic adenocarcinoma cell line Capan-1. 160,000 cells were placed per well in a plate with 24 wells. After 24 h of culture, the viability fluorophore, BCECF-AM, was added, as well as the doses of PCI to be tested: 0 μg/mL, 10 μg/mL, 30 μg/mL, 45 μg/mL, 60 μg/mL and 75 μg/mL. The intensity of the fluorescence was measured during 24 h. The values were determined in quadruplicate.
Figure 17:
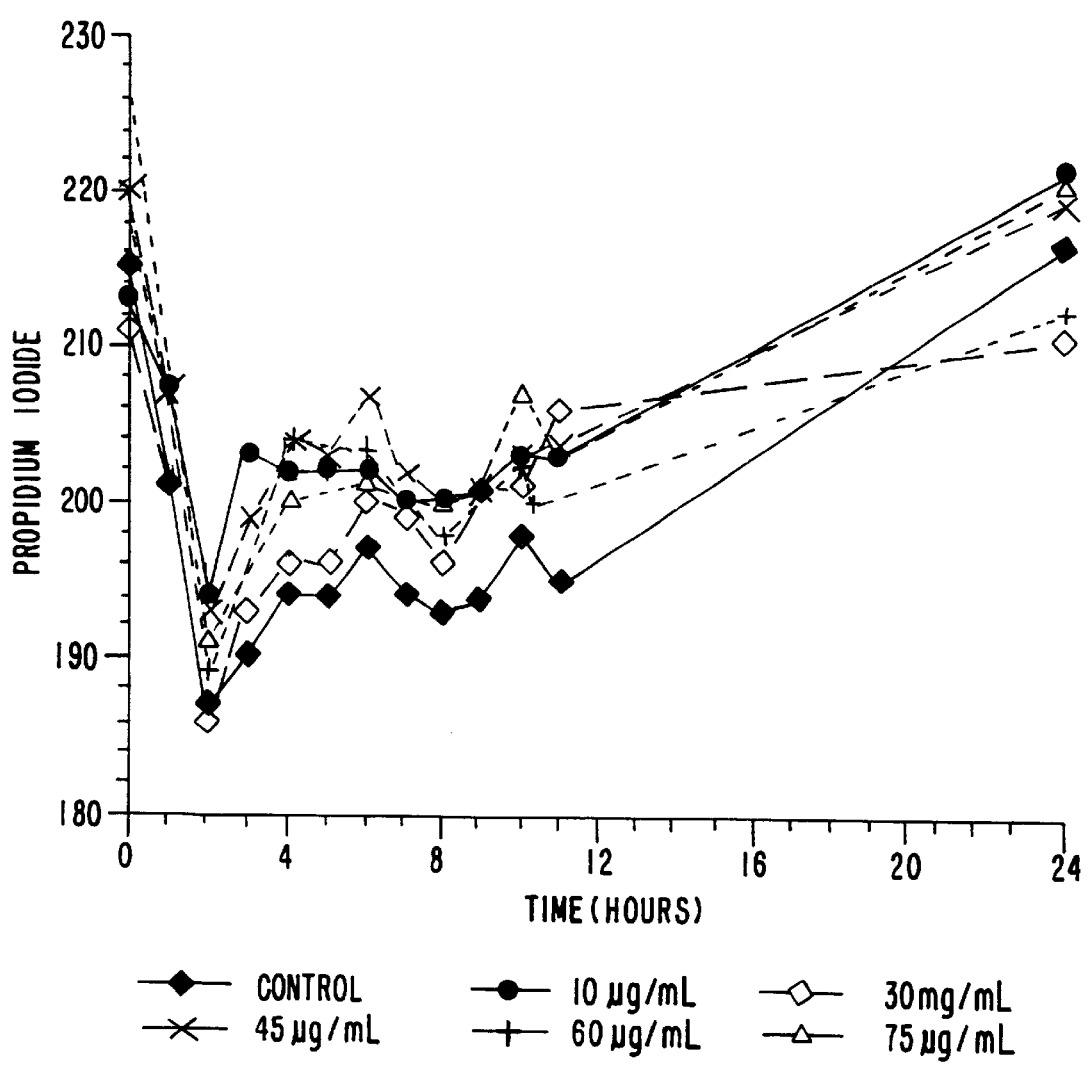
FIG. 17: Test of cytotoxicity of the PCI on the human pancreatic adenocarcinoma cell line Capan-1. 160,000 cells were placed per well in a plate with 24 wells. After 24 h of culture, the fluorophore for nucleic acids, propydium iodide, was added as well as the doses of PCI to be tested: 0 μg/mL, 10 μg/mL, 30 μg/mL, 45 μg/mL, 60 μg/mL and 75 μg/mL. The intensity of the fluorescence was measured during 24 h. The values were determined in quadruplicate. The decrease of intensity observed during the first two hours was due to the fact that the culture medium, without buffering as a result of the $CO_2$ of the incubator, interfered in the value of fluorescence of the propydium iodide.

The results obtained are presented in FIGS. 16 and 17, in which the variation of the intensity of the fluorescence for each one of the fluorophores in relation to the time for the various treatments with PCI is represented. As it can be seen in the case of BCECF-AM, which indicates the viability of the cells, there is no difference at all between control groups and treatments with PCI, no decrease of viability being observed; the decrease of intensity observed is due to the loss of fluorescence of the fluorophore along the time. No significant difference in relation to the control group is observed for propydium iodure either, and the slight increase of intensity that is observed is the same for the control group and the treatments, thus indicating that we are dealing with a spontaneous cell death which is not caused by the presence of the PCI.

4.F. Studies on the Cellular and Molecular Mechanism of Action of the PCI

In the previous studies it has been clearly established that the recombinant potato carboxypeptidase inhibitor has a clear inhibitory effect on: 1) the growth of tumor cell lines in culture, 2) the development of tumors induced in nude mice by injection of human pancreatic adenocarcinoma cells, and 3) the appearance of metastasis in liver of mice by injection of murine melanoma B16 cells. A whole series of lab experiments and computational analyses were carried out to try to gain insight into the molecular and cellular mechanisms responsible for such effects that would be relevant for the present invention.

4.F.1. PCI Internalization Tests

To find out whether the recombinant PCI is internalized by tumor cells in culture, two kinds of tests were carried out:
 a) Addition of PCI to culture media of the tumor cells and follow up PCI concentration in the culture media (in short, studies of disappearance of PCI).
 b) Labeling the PCI with a fluorophore and observation at the fluorescence microscope of tumor cells treated with such PCI at various times (in short, studies of internalization by fluorescence).

The result of these studies was that the two cell lines tested, Capan-1 and Panc-1, internalize significant amounts of PCI which is finded in a perinuclear location.

4.F.1.a. Studies of PCI Disappearance

The studies of PCI disappearance were carried out in the cell line Capan-1 by employing various concentrations of PCI.

Apart from what has been already described in Section 4.B.1., in this experiment, the materials used and the solutions required to carry out ELISAs and assays of carboxypeptidase inhibitory activity are accurately described in the bibliography cited in Section 4. A.

In three small culture flasks (of 25 cm$^2$), 5×10$^5$ cells were placed in each and they were cultivated in medium DMEM+ 10%FBS until the moment in which, through microscope observation, it could be seen that they had reached 75% of confluence. At this moment, the medium was removed and was substituted by new DMEM+10%FBS (50 µg/mL flask) and by medium with 200 µg/mL of PCI (flask 200 µg/mL). The three flasks were cultivated for a further 24 h. From each of these, samples of 100 µg/mL of culture medium were extracted at half hour intervals. In each of these samples, the existing concentration of PCI was determined by employing two methods (described in the bibliography cited in point 4.A.):
 Tests of carboxypeptidase A inhibitory activity
 ELISA.

In such tests, samples taken from the control flask at the same intervals were used as blanks.

One of the ELISAs that was done with the samples coming from the 200 µg/mL flask was carried out under special conditions in the first step (fixation of the antigens); concretely, by using a concentration of 0.5 M NaCl.

Figure 18:
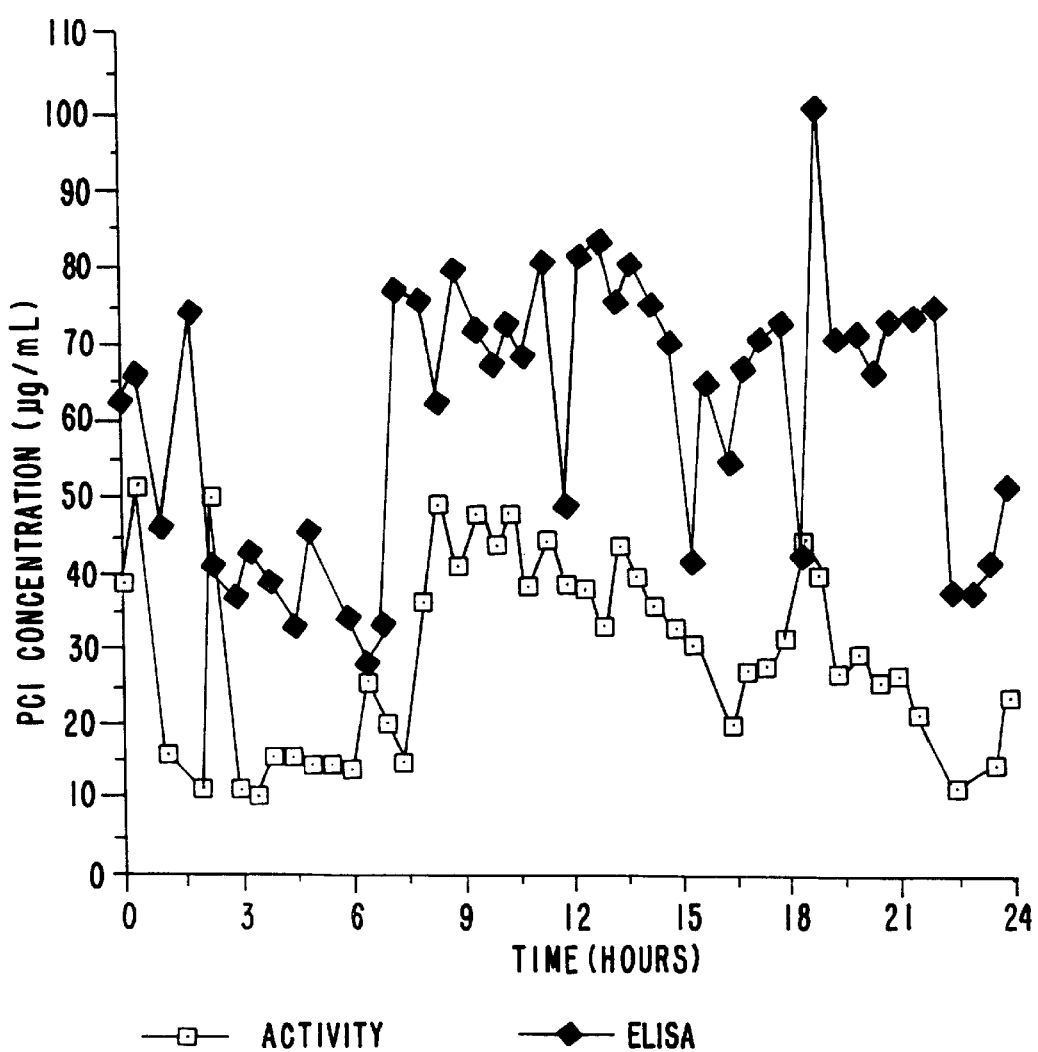
FIG. 18: Study of the presence of PCI added to the culture medium of the cell line Capan-1. $5 \times 10^5$ cells were put in a flask of 25 cm². When the cells were almost confluent, the medium was removed and half a flask plus 50 μg/mL of PCI were added. The presence of PCI in the medium was studied over a 24 h period; each point corresponds to measures taken every half hour. The concentration of PCI was determined by the inhibitory activity of the carboxypeptidase A (squares) and by ELISA with antibodies against the PCI (rhombus).

The results obtained in the case of the 50 µg/mL flask are shown in FIG. 18. The concentrations of PCI in the culture medium calculated from the tests of inhibitory activity and from the ELISA are, in general, quite coincidental, the discrepancies between both methods being probably due to the errors and imprecisions which are proper to these methods. As we observe in FIG. 18, the PCI is clearly internalized by the cells and its concentration in the culture medium markedly decreases around 1 h 30 min; and after, even more sharply, between 3 and 6 h. From this moment on, cycles of appearance and disappearance of the PCI from the culture medium seem to be observed, each between 3 and 5 h approximately.

Figure 19:
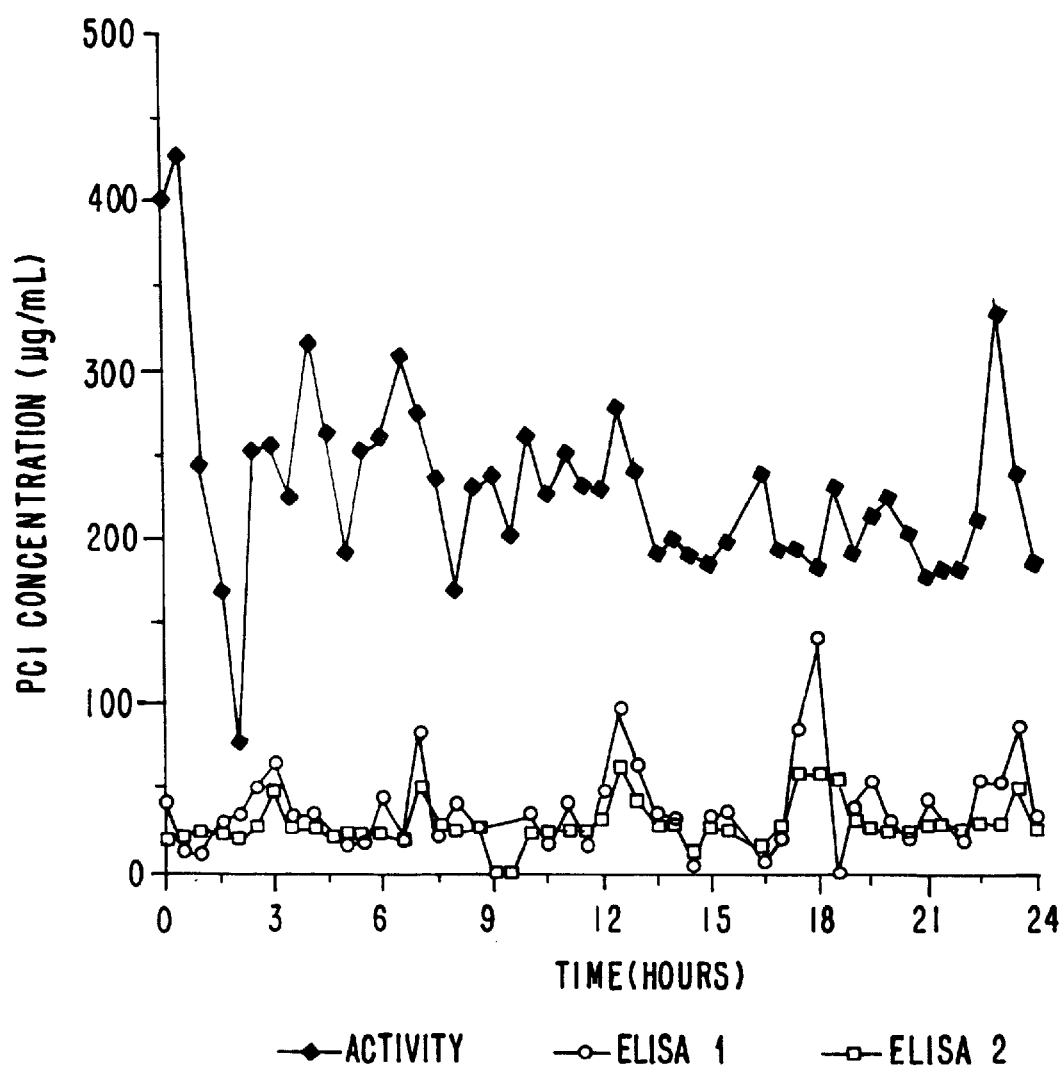
FIG. 19: Study of the presence of PCI added to the culture medium of the cell line Capan-1. $5 \times 10^5$ cells were put in a flask of 25 cm². When the cells were almost in confluence, the medium was removed and half a flask plus 200 μg/mL of PCI were added. The presence of the PCI in the medium was studied over a 24 h period; each point corresponds to measures taken every half hour. The concentration of PCI was determined by the inhibitory activity of the carboxypeptidase A (squares) and by ELISA with antibodies against the PCI (rhombus).

FIG. 19 shows the results for the flask 200 µg/mL. It can be observed, as in the previous case and especially in the measures for ELISA, repeated cycles of appearance and disappearance of PCI in the culture medium. The fact that, contrarily to the previous case, a clear difference is observed between the obtained results from the activity test and from the ELISA is very remarkable. The concentrations of PCI calculated from this last technique are five or ten times inferior and such difference cannot be explained by the errors inherent to both methods. To explain such discrepancies, an explanation based on the fact that the tests of activity are carried out in conditions of high ionic power (0.5M NaCl) was elaborated, something which does not happen in the case of ELISA. Indeed, it is possible that the PCI present in the culture medium is linked to proteins, membrane's residues, etc. and that such a union is broken under the conditions of high ionic power in the activity test. However, in the case of ELISA, this would not happen and such hypothetical proteins or residues of membrane would block PCI epitopes, so that the concentration that would be detected would be clearly inferior. This hypothesis was supported when carrying out an ELISA where the incubation of the samples (first step of the ELISA) was done under conditions of high ionic power (0.5 M NaCl), identical to that which is employed in activity tests. The result of the ELISA was that concentrations of PCI much higher than those determined by the previous ELISA and very similar to the concentrations found in activity tests were detected in the culture media.

4.F.1.b. Internalization Studies by Means of Fluorescence

In fluorescence studies, the possible internalization of PCI, labeled with a fluorophore, by Capan-1 and Panc-1 cell lines was followed by microscope observation.

In addition to the material and solutions previously described, this experiment employed:
 Rhodamine isotiocyanate (RITC) (Aldrich, Germany).
 Culture chambers/slides (Nunc, Denmark).
 PD-10 columns with Sephadex G-25 M (Pharmacia, Sweden).
 Zeiss fluorescence microscope (Germany).

a) Method for PCI Labeling with RITC

The chosen fluorophore was RITC (Rhodamine B isothiocyanate) which selectively reacts with amines by means of its isothiocyanate group. Thus, it may react with the free amino groups of the N-terminal tail or with the amino groups of the lisines 10 and 13 of the PCI molecule, producing relatively stable compounds with a spectrum of absorption and emission not too sensitive to pH. These compounds would be excitable and emit light at 546 nm.

The labeling protocol was that described by Billings, P. C. et al. (1989) *Carcinogenesis*, 10: 687–691, slightly modified:
 1. 2 mg of PCI in 0.5 M sodium bicarbonate buffer (pH 9.2) until a final concentration 1 mg/mL (solution A).
 2. 0.4 mg of RITC dissolved in milliQ grade water until a concentration 1 mg/mL (solution B).

3. Solutions A and B are mixed at room temperature for 3 h on a shaker, always protecting the solution from light.

4. It is centrifuged at 2,000×g for 1 minute so that the insoluble material is precipitated.

5. To eliminate the free RITC not linked to the PCI, the sample is passed through a PD-10 column, according to the following protocol:

Wash the column with 25 mL of milli Q grade water.

Add the sample in a volume of not more than 2.5 mL.

Elute the RITC-PCI with 4 mL of Milli Q grade water. To obtain the free RITC use an additional amount of 10 mL of water through the column.

This last step makes it possible to separate the free RITC from that linked to the PCI. The latter being eluted in the volume of exclusion of the column.

b) Quantifying the Labeled PCI

The amount of RITC linked to the inhibitor is spectrophotometrically determined (the coefficient of molar extinction of the RITC at 560 nm is of $\epsilon=22,000M^{-1}$).

The amount of labeled PCI is determined by means of an inhibition test of the carboxypeptidase A activity using the solution of free RITC which is eluted from the PD-10 column as a blank.

c) Internalization of the RITC-PCI to the Cell Cultures

In the incorporation studies of the RITC-PCI, the protocol of Billings, P. C. et al. (1989) *Carcinogenesis*, 10: 687–691, slightly modified, was followed:

1. 200,000 cells of the cell line to be studied were placed in culture chambers/slides and were left there to grow for 48 h.

2. The medium of the cells growing in exponential phase was changed and 20 or 50 µg/mL of RITC-PCI were added to the new medium, keeping it in the medium for a variable incubation time ranging from 1 minute to 4 h inside the incubator.

3. The medium was retired after the incubation and the monolayer of the cells was washed with PBS for 10 min in darkness.

4. The cells were fixed with 350 µl of a solution 50% methanol—50% acetone for 8 min at 4° C. in a dark and humid chamber.

5. The cells were washed again with PBS for 10 min in darkness.

6. The preparations were dried with absorbing paper being very careful not to touch the cells. The preparations were fitted with PBS: Glycerol (1:1) and were sealed with nail polish. Later, they were observed in the fluorescence microscope; if the observation was not immediate, the preparations were maintained at 4° C. in darkness.

Apart from the cultures of Capan-1 and Panc-1 cells to which the PCI-RITC was added, a series of control tests were carried out:

a A culture was incubated with the solution of RITC eluted from the PD-10 column, to verify if there was union or unspecific internalization of the fluorophore with the cells.

b RITC-PCI was added to a plate without cells to see if it unspecifically adhered to the plate.

c RITC-PCI was not added to a last control culture to verify the absence of fluorescence which is characteristic of the cells.

The results of the three controls were negative; that is to say, no fluorescence was detected.

In relation to PCI internalization analysis, the following results were obtained:

d) Analysis of the Efficiency of the PCI Labeled with RITC

In order to confirm that the cells really incorporate PCI, it was decided to mark it in a fluorescent way which made it possible to observe under the microscope such incorporation and study it inside the cell.

The fluorophore used was RITC, according to Billings, P. C. et al. (1989) *Carcinogenesis*, 10: 687–691. RITC reacts with the amino groups of the lisines and of the N-terminal. In both cases, the place of reaction was far from the region of PCI which interacts with the carboxypeptidase, thus being possible to determine its concentration by means of inhibition tests of the carboxypeptidase A activity. The amount of RITC incorporated by the PCI was evaluated spectrophotometrically.

The typical results obtained when labeling the PCI with RITC were that approximately each mol of PCI reacts with 0.66 mols of RITC. Since the PCI had three sites of RITC union (free amino groups), it can be stated that the probability that one should be marked is 0.22. From this it can inferred that 43% of the molecules of PCI are not labeled and that from the other 57%, 40% would be labeled in a single site and 13% in more than one site.

e) Incorporation of the RITC-PCI in Cultures of Capan-1 land Panc-1 Cells

Before starting the studies of incorporation of RITC-PCI to the cell lines, the blanks described in the methods were carried out which made it possible to verify that:

a The cells do not internalize free RITC.

b The RITC-PCI does not specifically adhered to the surface of the culture chambers.

c The cells of the tested cell lines do not present the same intrinsic fluorescence on the wave lengths as that of the RITC.

Figure 20A:
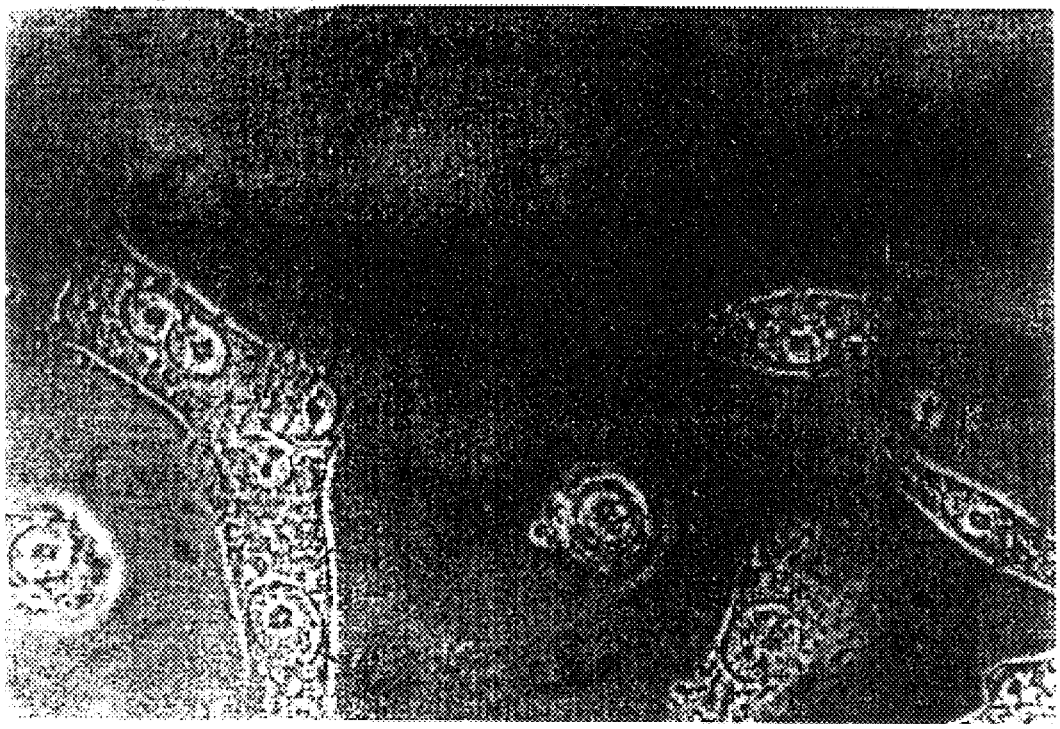
FIG. 20: Microphotography of the incorporation of RITC-PCI by cells of the cell line Capan-1 exponentially growing in a full medium supplemented with BMS at 10%. (A) Image taken with inverted microscope of phases' contrast. Cells incubated with [RITC-PCI]=20 μg/mL for 4 h. (B) Image taken with fluorescence microscope of the cells of the picture (A).
Figure 20B:

The result of the incorporation studies of RITC-PCI by Capan-1 cells offered, as a general result, that such cells presented an intense fluorescence in the microscope, revealing that they internalize significant amounts of marked PCI. The fluorescence was visualized in all the inside of the cytoplasm but with a clear accumulation around the nucleus (perinuclear localization). Such perinuclear localization already appears in cells exposed to the RITC-PCI for only 1 minute. All this may be observed in FIG. 20, where a phase contrast microphotography of the cells and one of fluorescence show us the kind of PCI internalization of the Capan-1 cells.

The exposure time required to be able to photograph the cells gives us an idea of the intensity of the labeling that is the amount of PCI captured by them. Thus, at a higher intensity, less exposure time is required. Generally speaking, the incubated cells with the same concentration of PCI presented higher labeling intensity in accordance with the length of time they had been in contact with it. Nevertheless, we have to point out that there were differences in the intensity of the fluorescence between different cells belonging to the same sample. If we compare the fluorescence microphotographies with the ones of a clear field, we might appreciate that the cells with higher intensity of the labeling presented a disintegrated core, non-spheric, and were sometimes difficult to see.

The Panc-1 cell line presented also a perinuclear labeling pattern. As a general trend, for the same periods of incubation and of concentration of RITC-PCI, the labeling of Panc-1 cells was a little less intense than for Capan-1 (exposure times a little higher were required to obtain a microphotography). Thus, it can be inferred that the amount of PCI internalized by Panc-1 cells is somewhat smaller than that internalized by Capan-1 cells f) Labeling PCIdelYVG with RITC Given the fact that proliferation tests were carried out with the PCI mutant with the C-terminal YVG deletion, and as it appeared that this one had had an effect on cell growth, the labeling of this mutant started by using a fluorophore to study the possible internalization of the labeled PCIdelYVG by the Panc-1 cell line. The labeling protocol was exactly the same as that of the wild PCI, as described in Section 4.F.1.b. The studies of incorporation of the labeled mutant were carried out as described in Section 4.F.1.c.

From the incorporation studies we may conclude that the mutant PCIdelYVG is incorporated by the cells of the human pancreatic adenocarcinoma cell line Panc-1. As in the case of the wild PCI, the labeling is visualized in all the cytoplasm, but with a clear accumulation around the nucleus.

The exposure time required to be able to photograph the cells, which gives us an idea of the intensity of the labeling and, with it, of the amount of labeled molecule captured by the cells, is slightly inferior in the case of the mutant PCIdelYVG for identical incubation times and concentrations to those of the wild PCI. This indicates that the mutant is captured by the cells but with greater difficulty than in the case of wild PCI.

4.F.2. Possible Relation with Apoptosis

To study in depth the mechanism by which the PCI produces a decrease of the growth rate of the Capan-1 cell line and based on the observed morphology of the cells treated with PCI, the possibility that the PCI would induce apoptosis (or programmed cell death) was studied.

The apoptotic cells undergo a condensation of the chromatin which is followed by a fragmentation of the nucleus in the so called apoptotic bodies (Earnshaw, W. C. (1995) *Curr, Opin. Cell Biol.,* 7: 337–343). This phenomenon is easily observable using the specific dying of the DNA with DAPI (4,6-diamine-2-phenylindol), since the apoptotic cells present a very intense labeling due to the condensation of the chromatin. In addition, the fragmented nucleus is also observed. Thus, through observation in the fluorescence microscope, we may determine whether the PCI induces apoptosis and the percentage in which this phenomenon is produced.

Apart from the material and solutions previously described, in these experiments the following equipment was employed:

Chambers/slides (Nunc, Denmark).
2% Formaldehyde (Panreac, Spain).
0.25% Triton x100 in PBS (Sigma, Spain).
DAPI (4,6-diamine-2-phenylindol) (Sigma, Spain).
Fluoropep (Biomerx, France).

The studies of possible induction of apoptosis by the PCI were done with the human pancreatic adenocarcinoma cell line Capan-1. The detailed procedure that was employed is as follows:

1. $5 \times 10^5$ cells were seed in the chambers/slides and were cultured for 3 o 4 days (until the moment in which, through microscope observation, they presented 75% of confluence). The cells were cultured in DMEM+10% FBS.

2. The conditioned medium of the cells growing in exponential phase was changed and in the new medium different concentrations of PCI were added: 0.1 $\mu$g/mL, 10 $\mu$g/mL, 50 $\mu$g/mL and 200 $\mu$g/mL. A positive control was added, cysplatinum, at a concentration of 10 $\mu$g/mL (a drug which induces apoptosis in various tumor cell lines, Borner, M. M., et al. (1995) *Cancer Res.,* 55: 2122–2128. The incubation period was 24 h.

3. The medium was removed after incubation and the chamber was washed with 2 mL of PBS.

5. Cells were fixed with 2 mL of 2% formaldehyde for 20 min at 4° C.

6. The plates were washed again with 2 mL of PBS for 5 min at room temperature.

7. Cell membranes were permeabilized with 0.25% Triton x100 in PBS for 5 min at 4° C.

8. Washed with PBS for 5 min at room temperature.

9. The cells were labeled with DAPI at a final concentration of 2 $\mu$g/mL for 50 min in darkness at room temperature.

10. The preparation was fitted with the fluoroprep medium and it was examined through the fluorescence microscope.

To confirm that a possible way of growth inhibition by the PCI might in fact be the induction of apoptosis, it was decided to treat the cells and to later carry out a specific labeling of DNA which would make it possible to distinguish the apoptotic cells from the live cells. The treatment was carried out with various doses of PCI and cysplatinum, as positive control, which was done over a 24 hour period.

The preparations were observed in the fluorescence microscope and the number of apoptotic cells and the total number of cells were counted which made it possible to calculate the % of apoptosis by means of the following formula:

% apoptosis=(number of apoptotic cells/total number of cells)×100

Figure 21:
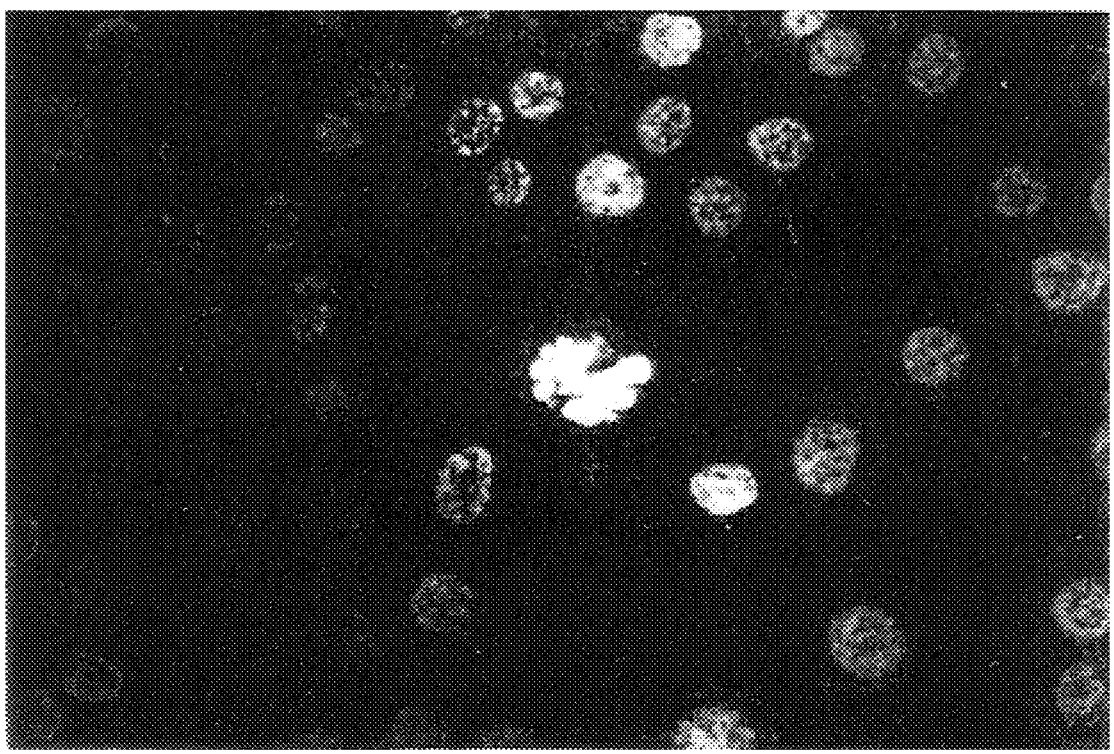
FIG. 21: Microphotography of the labeling with DAPI of Capan-1 cells. Cells that were exponentially growing were treated in full medium supplemented with BMS at 10%, with 50 μg/mL of PCI for 24 h. Picture taken by fluorescence microscope, where cellular nuclei dyed with DAPI were observed.

The results obtained, corresponding to three tests, are presented in Table 16 and FIG. 21. As it can be seen, the cysplatinum clearly induces apoptosis and, in the case of the PCI, at a concentration of 50 $\mu$g/mL causes the highest index of apoptosis, 5 times higher than the control.

Nevertheless, these levels may appear to be very low and given the fact that in the proliferation tests the inhibition of the growth is at least of 50%, this would lead us to think that possibly a longer exposure to the PCI is required to cause a higher number of cells to enter into apoptosis. However, it seems that we can confirm that the PCI would stop the growth of the tumor and not through inducing the death of the tumoral cells.

TABLE 16

Percentage of apoptosis induced by PCI on the Capan-1 cell line.

| Sample | % Apoptosis |
| --- | --- |
| Negative control (0 mg/mL PCI) | 0.08 |
| 0,1 mg/mL PCI | 0.11 |
| 10 mg/mL PCI | 0.095 |
| 50 mg/mL PCI | 0.41 |
| 200 mg/mL PCI | 0.038 |
| cysplatinum (positive control) | 5.19 |

4.F.3. Relationship with the Alteration of the Glycosylation Pattern

To verify whether the PCI when affecting cell growth may provoke metabolic changes too, we analysed the changes in a secreted protein, ribonuclease, in the human pancreatic adenocarcinoma cell line Capan-1. Apart from the mentioned material required for cell culture, this analysis was based on the detection of ribonuclease activity by means of the electrophoretic analysis in activity gels (zymograms) (Bravo, J. et al (1994) *Anal Biochem.,* 219: 82–86).

With this aim in mind, the culture medium of the proliferation tests of Section 4.B.1 was taken. Thus, a culture medium of control cells was provided for cells treated with PCI from the beginning (preanchorage) and for cells treated once they had adhered to the culture surface (postanchorage). Given the fact that the FBS contains bovine ribonuclease which would interfere in our research, these cells grew in DMEM supplemented with BMS at 10%. The procedure was as follows:

The medium was taken from the culture flasks and centrifuged at 1500 rpm for 10 min.

Not for immediate use, it was frozen at −20° C. in sterile tubes.

At the moment of the analyses, the media were unfrozen in order to have an aliquot of each sample. The concentration of total protein was determined by means of the Bradford method (Bradford, M. M. (1976) *Anal. Biochem.*, 72: 248–254).

An activity electrophoretic gel analysis (zymogram) was done, the same amount of total protein of each sample being used.

Figure 22:
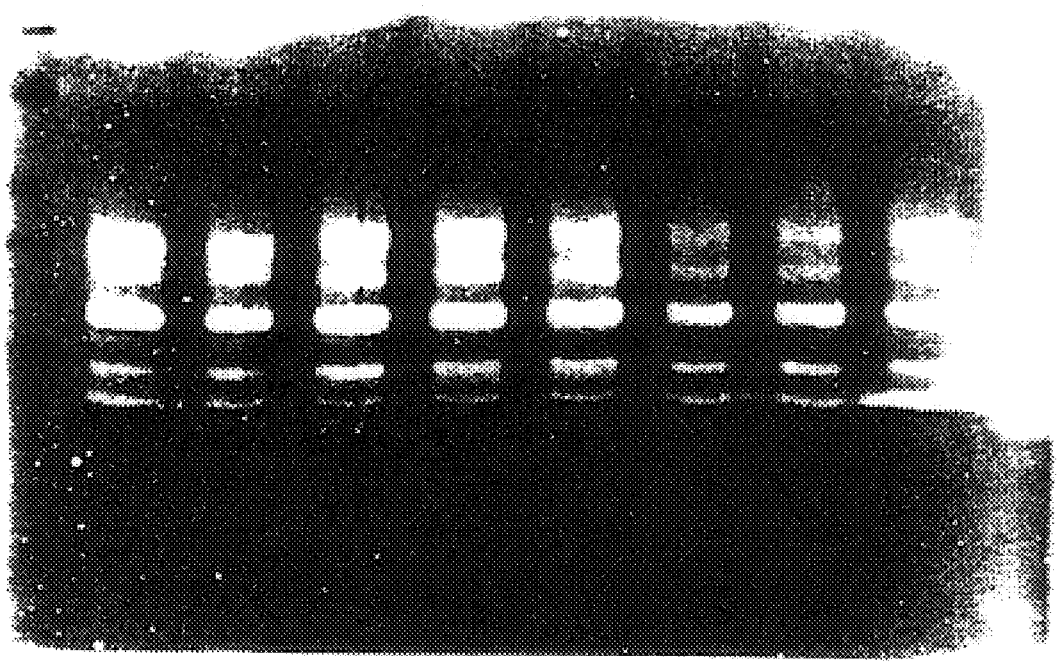
FIG. 22: Electrophoretic analysis in gels of ribonuclease activity (dyed with toluidine) of the culture mediums of the cell line Capan-1 with 2.5 μg of total protein of each sample. 1: low molecular weight markers; 2 and 3: control samples; 4, 5, 6 and 7: samples where the PCI was added after adhesion; 8 and 9: samples where the PCI was added before adhesion; 10: Ribonuclease A.

The analysis of ribonuclease secretion was done with Capan-1. The concentration of PCI employed to treat the cells pre and postadhesion was 5 µg/mL. Using the electrophoretic analysis of ribonuclease activity, the pattern of glycosylation of this protein could be observed and a certain quantification could be made. As may be observed in FIG. 22, for the line Capan-1 there is a higher secretion of ribonuclease with a higher degree of glycosylation compared to the control group, a fact that is more relevant in the situation of postadhesion than in the situation of preadhesion. These results show us that the cells, in the case of Capan-1 and in presence of PCI, are glycosylating with greater intensity and, therefore, that the glycosylation mechanism of the Golgi's apparatus is overstimulated. This suggests that signal transduction pathway could be affected.

4.F.4. Flow Cytometry Analysis of Cell Cycle Phases

The flow cytometry methodology allows us to make histograms of DNA contents from which the percentage of cells which are present in each one of the cell cycle phases can be estimated: $G_1$, S and G2/M (Ormerod, M. G. (1992) *Cytometry*, 13: 678–685; Darzynkiewicz, Z. et al. (1992) *Cytometry*, 13: 795–808).

The aim of this experiment is to determine whether the treatment of cells of the human pancreatic adenocarcinoma cell line Capan-1 with PCI produces some variation in the distribution of the cell cycle phases; that is to say, whether growth is stopped in a particular phase. In addition to the material already mentioned in Section 4.B.1., the materials and solutions required to carry out a flow cytometry test were the following:

Washing solution: PBS free of $Ca^{2+}$ and $Mg^{2+}$.

CMFH-Trypsin-EDTA buffer: 7.54 g/L NaCl, 0.37 g/L KCl, 0.09 g/L $Na_2HPO_4*7H_2O$, 0.0478 g/L $Na_2HPO_4$, 0.084 g/L $NaHCO_3$, 0.9 g/L glucose (dextrose), 5.96 g/L Hepes, trypsin at a final concentration 0.0025% and EDTA at a final concentration 2 mM. Such solution is buffered with NaOH at pH=7.4, and, afterwards, it is filtered under bell with a filter of 0.22 µm.

Cells' fixing solution: 70% ethanol at −20° C.

Propydium iodide solution: propydium iodide (PI) 50 µg/mL and ribonuclease 20 µg/mL.

Flow cytometer: EPICS-752 Flow Cytometer (Coulter Electronics Inc, Hialeah, Fla.).

The procedure which has been employed to carry out the studies of flow cytometry is detailed as follows:

1. $1 \times 10^6$ cells were placed in flasks of 25 cm² which were kept in culture for 5 days. 5 flasks were used for the various treatments to be carried out: one control group and four treatments; these were treated with 50 µg/mL of PCI at various times: 96 h, 72 h, 48 h, 24 h.

2. After the treatment, the cells were washed twice with the washing solution.

3. The cells started being detached by adding 1 mL of the CMFH-Trypsin-EDTA buffer per flask. The reaction was stopped by adding 2 mL of full medium per flask.

4. The cells were centrifuged for 5 min at 1500 rpm.

5. The cells were washed twice with PBS free of $Ca^{2+}$ and $Mg^{2+}$. In the last wash the supernatant was discarded.

6. The sediment was suspended again in 200 µL PBS free of $Ca^{2+}$ and $Mg^{2+}$; 2mL of 70% ethanol at −20° C. were added. It should be shaken lightly while pouring to avoid the formation of cell aggregates. At this point, the cells may be kept at 4° C. until they are passed through the flow cytometer, the minimum setting time being 2 h.

7. The day of the analysis by cytometer, the cells were centrifuged for 5 min at 1,500 rpm and at 4° C.

8. Wash the sediment of the cells twice with PBS free of $Ca^{2+}$ and $Mg^{2+}$.

9. Stain the cells for 15 min at 37° C. with 1 mL of the propydium iodide solution.

10. Pass the cells through the flow cytometer, stimulating them with a 488 nm laser, which detects the red fluorescence of the DNA-PI compounds.

Flow cytometry allows us to determine the percentage of cells in the cycle phases: $G_1$, S and $G_2M$. In this way, the distribution of each treatment carried out may be compared. The obtained results are shown in Table 17.

As follows from the results of the table, the PCI produces an increase in the number of cells in $G_1$. Therefore, we may conclude that the PCI has an inhibitory effect on the growth since it stops the cells in the phase $G_1$ of the cell cycle by halting their division. This fact is corroborated by the observation of an overexpression of p53 (Section 4.F.5).

TABLE 17

Results of flow cytometry. Cells of the human pancreatic adenocarcinoma cell line Capan-1 treated with 50 mg/mL of PCI added to the culture medium at different times.

| Treatment | % $G_1$ | % S | % $G_2$ M |
|---|---|---|---|
| Control | 79.2 | 14.3 | 6.4 |
| 24 h | 74.9 | 20.4 | 4.7 |
| 48 h | 85.3 | 11 | 3.7 |
| 72 h | 85.1 | 10.9 | 4 |
| 96 h | 88.5 | 7.6 | 3.9 |

4.F.5. Gene Expression Analysis of Cells Treated with PCI

To verify whether the PCI plays any role in signal transduction, studies of gene expression were carried out by Northern transfer. The probes were: β2-microglobulin, p53 and trypsin. The β2-microglobulin is a constitutive gene that is used as a sample loading control in the gel. p53 is a transcription factor which, among other functions, controls the state of the genomic DNA and the cell cycle (Bates, S. & Vousden, K. H. (1996) *Curr. Opin. Genet. Develop.*, 6: 12–19). If the DNA is damaged, p53 induces its repair and, if it is excessively damaged, it provokes programmed cellular death (apoptosis). Trypsin is a marker of pancreatic cells of the acinar type. The trypsin is not expressed by all the tumoral cells and it is believed that it is expressed by the cells with metastatic power and/or invasive power (Fernández, E. et al., (1994) *Cancer*, 73: 2285–2295). The probes employed are described as follows:

a) β2-Microglobulin

Probe obtained by PCR from human genomic DNA. It was obtained by employing the following primers:

B2M-N901-920/5: TTAGCTGTGCTCGCGCTACT (SEQ ID NO:5)

B2M-N3999-3980: TAACCACAACCATGCTTAC (SEQ ID NO:6)

which were designed from the β2-microglobulin gene. The resulting probe has 940 pb. (Gussow, D. et al. (1987) *J. Immunol.,* 139: 3132–3138).

b) p53

Probe obtained from the retrotranscription of mRNA from human cells. The insert of 1760 bp was inserted in the blanks Sal I and EcoRI sites of a pUC8 plasmid. The plasmid codes the ampicillin resistance. (Harlow, E. D. et al. (1985) *Mol. Cel. Biol.,* 5: 1601–1610).

c) Trypsin

Probe obtained from the mRNA of the trypsinogen I of rat pancreas. The insert of approximately 700 bp, pcXP4-78, was cloned in the PstI site of a PBR322 plasmid. The plasmid codes the tetracycline resistance and ampicillin sensitivity (McDonald et al. (1982) *J. Biol. Chem.,* 257: 14582–14585).

The methodology employed contains various stages, which are detailed as follows:

1. Extraction of Total RNA: Method of the Guanidine Thiocyanate

Method according to Chomczynski, P. & Sacchi, N. (1987) *Anal. Biochem.,* 162: 156–159.

In the first place, $3\times10^6$ cells of the human pancreatic adenocarcinoma cell line Capan-1 were placed in each one of the 12 flasks of 150 cm$^2$. These were divided in 3 groups of 4 flasks: a control group and two groups treated with 1 and 10 µg/mL of PCI, respectively. They were maintained in culture for 12 days period, changing their medium every 4 days, adding fresh PCI. Once the treatment was completed, the cells were trypsinized and the sediment of the cells was kept at −80° C. Afterwards, the extraction of the RNA was carried out.

To extract the RNA it is necessary to be extremely careful for any contamination of ribonuclease, which would damage the entire sample. For this reason, it is necessary to always work with clean gloves, sterilize all plastic material and use it only for extracting RNA, wash the material made out of glass with 1N NaOH and rinse it with sterile distilled water treated with diethylpyrocarbonate (DEP) (Sigma, USA), and, finally, treat all the aqueous solutions with DEP shaking for at least 6 h (DEP 0.1%) and sterilize afterwards (when sterilizing, the DEP is eliminated). The following solutions were used:

Stock Solution: 250 g of guanidine thiocyanate (Promega), 293 mL of sterile H$_2$O, 17.6 mL of 0.75 M sodium citrate pH 7, add 26.4 mL of 10% sacorsil and at 65° C. Sterilize by filtering and keep out of the light.

D solution: mixture of 0.36 mL of 2-mercaptoethanol by each 50 mL of stock solution: (4M guanidine thiocyanate, 25 mM sodium citrate pH 7, 0.5% sarcosil and 0.1M 2-mercaptoethanol).

Chloroform-isoamyl alcohol (49:1).

Phenol saturated with water.

2M sodium acetate pH 4 treated with DEP and sterilized.

0.5% SDS treated with DEP or 1 mM EDTA pH8 treated with DEP and sterile.

The following method was used to extract the RNA:

1. Use frozen tissue stored in dry ice and fresh or frozen cells. Keep all the apparatus and solutions at 4° C. Wash the glass material with 1M NaOH and rinse it with sterile water treated with DEP. Submerge the homogenizer with 1M NaOH for 10 min and rinse.

2. Homogenize the tissue (100 mg) in a sterile tube with 1 mL of solution. For the cells, add 1 mL of D solution to each conic tube and vortex for 2 min.

3. Add 0.1 mL of 2 M sodium acetate pH 4. Vortex for 5 seconds.

4. Add 1 mL of phenol. Vortex for 5 seconds.

5. Add 0.2 mL of the mixture of chloroform-isoamyl alcohol. Vortex for 10 seconds. Maintain in ice for 15 min.

6. Centrifuge in Sorvall SS-34 at 10,000 rpm, at 4° C. for 20 min.

7. To precipitate the RNA, transfer the aquous phase to a new tube and add 1 volume of isopropanol in ice (or add 2 volumes in cold ethanol). Vortex for 10 seconds and leave at −20° C. for one hour.

8. Centrifuge at 10,000 rpm at 4° C. for 20 min. Eliminate the supernatant.

9. The RNA is precipitated again as follows: dissolve the pellet of RNA in 0.3. mL of D solution. Transfer to an eppendorf and precipitate with 1 volume of isopropanol (or double volume of ethanol). Vortex 10 seconds and maintain at −20° C. for 1 hour.

10. Centrifuge at 10,000 rpm at 4° C. for 10 min. Discard the supernatant.

11. Wash the pellet with 0.5 mL of cold ethanol at 75%. Centrifuge at 10,000 rpm at 40° C. for 10 min. Discard the supernatant and dry in a rotatory evaporator for 15 min.

12. Dissolve the pellet in 50 µg of 0.5% SDS at 65° C. and maintain at this temperature for 10 min. It can also be dissolved in 1 mMEDTA, pH 8.

2. Electrophoresis with Citric Acid

The concentration of total RNA obtained is calculated as follows: 5 µL are taken as a sample and are dissolved in 0.5 mL of H$_2$O treated with DEP. The absorbancy is read at 260 nm in quartz cuvettes treated with 1N NaOH and washed with H$_2$O sterilized and treated with DEP. 50 µg of total RNA are estimated per each unit of optic density.

To verify the quality of the RNA extracted, this underwent electrophoresis in urea-citric acid gels (Frazier, M. L. et al. (1983) *Mol. Cell. Biochem.,* 56: 113–122).

10 M urea.

0.25 M citrate pH 3.5: 8.03 g of citric acid, 10 g NaOH, until 1 liter.

Loading buffer: 5 mL of citrate 0.25 M, 39 mL of urea 10M, 10 g of saccharose and 25 mg of bromophenol blue, top up with water until it reaches 50 mL.

1. Prepare a 2% agarose gel: 2 g of agarose, 60 mL of 10M urea, 10 mL of 0.25 M citrate and 30 mL of distilled water. Melt the agar in a microwave and prepare the gel using the usual method (Sambrook, J., Fritsch, E. F. and Maniatis, T. (1989) "Molecular Cloning: A Laboratory Manual", 2nd edn., Cold Spring Harbor Laboratory Press, Cold Spring Harbor, N.Y.).

2. Load from with 3 to 5 µg of total RNA per well onto a volume of 20 µL. Add 30 µg of loading buffer.

3. For the electrophoresis, prepare 1 liter of buffer: 100 mL of 0.25M citrate and 900 mL of water. Place the buffer in the bucket, be careful not to submerge the gel and make sure the buffers on either side of the bucket do not come into contact.

4. Let the gel run at 100 V until the bromophenol blue has run a distance of approximately 3 cm.

5. Dye the gel for between 15 and 30 min with 5 µg/mL of ethidium bromide in 50 mM Tris-HCl pH 7.6 (10 mg/mL). Rinse with water. Visualize in U.V. transluminator and photograph.

3. Obtention of Poly(A$^+$) RNA

In the obtention of poly(A$^+$) RNA it is necessary to be extremely careful in order to avoid contamination with ribonuclease, as no steps can be carried out in the presence of ribonuclease inhibitors and, in addition, the samples are not deproteinized either. Therefore, it is necessary to work with recently sterilized material, gloves and solutions treated with DEP and sterilized.

3.1. Columns of Oligo-dT (Frazier, M. L. et al. (1981) *Biochemistry*, 20: 367–371)

Oligo (dT) cellulose type 3 (Collaborative Research Incorporated, USA).

Binding buffer of high ionic strength; 0.5 M NaCl, 1 mM EDTA, 10 mM Tris, 0.1% sarcosil, pH 7.6. To prepare the buffer×4: 200 mL of 5M NaCl, 100 mL of 20 mM EDTA, 20 mL of 1M Tris, 10 mL of 20% sarcosil, up to 500 mL with $H_2O$. Treat with DEP and sterilize.

Buffer with low ionic strength: 10 mM Tris, 0.1% sarcosil, pH 7.6 (10 mL of 1M Tris and 5 mL of 20% sarcosil in a total volume of 1 liter), treat with DEP and sterilize in the autoclave.

4.5 M sodium acetate pH 6 treated with DEP and sterilized.

1. Prepare a sterile syringe of 1 mL covering the outlet with glass wool. Take approximately 0.5 g of oligo-dT resin and dissolve it in high ionic strength buffer 1×. Let it sediment with care, wash the column with 50 mL of buffer with high ionic strength 1×.

2. Prepare the sample. It has to start from 2 mg of total RNA to a concentration of 250 μg/mL in buffer with high ionic strength 1×; to do that, we will dilute the sample with high ionic strength buffer 4× and sterile distilled water, free from ribonuclease. Heat the sample at 70° C. for 5 min to reduce the aggregation of RNA, cool quickly in ice. Fit to buffer of high ionic strength 1× with the prepared buffer at 4× and water (do not add high ionic strength buffer to the sample before heating and cooling it).

3. Load the sample onto the column. Collect the eluted volume. Wash the column with the high ionic strength buffer 1× until the $DO_{260}$ is insignificant, about mL.

4. Elute poly($A^+$) RNA in the column with low ionic strength buffer (between 2–2.5 mL) collecting fractions of 0.5 mL. Collect fractions until the readings at 260 nm are negligible.

5. Each fraction eluted with low ionic strength buffer must be precipitated with 2 volumes of cold ethanol and 1/24 volumes of 4.5M sodium acetate pH 6. Top up the volumes to 3 mL in tubes of ultracentrifuge to facilitate later centrifugation. Keep overnight at −20° C.

6. Level off the tubes with cold ethanol. Place them in the SW 60 rotor of the Beckmann ultracentrifuge. Ultracentrifuge at 40,000 rpm for 30 min.

7. Wash the pellet with 3 mL of ethanol at 70% cold. Ultracentrifuge at 40,000 rpm (SW60 Beckmann) for 30 min.

8. Suspend again in 100 μL of sterile water free of ribonuclease. Determine the concentration by reading at 260 nm. The poly($A^+$) RNA means 5% of the total RNA. Using this method, recuperations between 50% and 75% are obtained.

3.2. Magnetospheres

The isolation system of poly($A^+$) RNA with magnetospheres (PolyATtract mRNA Isolation Systems, Promega, USA) makes it possible to isolate mRNA in 45 min starting from total RNA without using oligo(dT)cellulose columns thus eliminating the problems that this method implies. The system employs a primer of oligo (dT) biotinylated which hybridizes in solution at a high efficiency with the 3' poly($A^+$) region present in most of the eukaryote mature mRNAs. The hybrids are captured and washed at high stringency employing paramagnetic particles (PMP) together with streptavidin and a magnetic support. The mRNA is eluted from the solid phase by means of simple addition of sterile ribonuclease-free water.

20×SSC is employed: 87.7 g of NaCl, 44.1 g of sodium citrate, 500 mL of $H_2O$ and fit the pH to 7.2 with NaOH. Treat with DEP and sterilize.

1. In a sterile tube, take between 0.1–1 mg of total RNA and top it up to a volume of 500 μL with ribonuclease-free water. Place the tube in a thermic block at 65° C. for 10 min.

2. Add 3 μL of oligo primer biotinylated and 13 μL of 20×SSC to the tube containing RNA. Mix gently and incubate at room temperature until it cools completely (10 min approximately). Prepare 1.2. mL of sterile 0.5×SSC (30 μL of 20×SSC and 1.17 mL of water) and 1.4 mL of 0.1×SSC sterile (7 μL of 20×SSC and 1.393 mL of water).

3. Gently suspend again the streptavidin-PMPs until they are completely dispersed in the tube and collect them in the magnetic support until all the particles are at the side of the tube (30 seconds). Very carefully, remouve the supernatant with a pipette (do not centrifuge the particles).

4. Wash the streptavidin-PMPs three times with 0.5×SSC (0.3 mL per washing) resuspending the particles in the solution, capturing the PMPs with the magnetic support and carefully draining the solution with the help of a pipette.

5. Suspend again the magnetic particles in 0.1 mL of 0.5×SSC. Add the contents of the ANNEALING reaction. Incubate at room temperature for 10 min.

6. Capture the PMPs by employing the magnetic support and eliminate the supernatant with care, without touching the particles. Keep the RNA supernatant until you are sure that the mRNA has joined the oligo(dT) primer.

7. Wash the particles four times with 0.1×SSC (0.3 mL per washing) as in step 4. In the final washing, eliminate the aqueous phase completely.

8. To elute the mRNA, suspend again the pellet of paramagnetic particles in 0.1 mL of ribonuclease-free water. Collect the PMP in the support and transfer the eluted mRNA to a sterile eppendorf. Repeat the elution, resuspending again the particles in 0.15 mL of water. Mix this mRNA with the previous one (total volume 0.25 mL). If, during this process, we have withdraw any particle, eliminate it by centrifugation. Determine the concentration by measuring the absorbance at 260 nm in ribonuclease-free cuvettes.

4. Northern Transfer 4.1. Denaturalizing Gels in Agar and Formaldehyde

Elution buffer×10 (MOPS): 41.8 g of MOPS, 4.1. g of sodium acetate, 40 mL of 250 mM EDTA, $H_2O$ until 1 liter, adjust to pH 7 with NaOH. Filter and keep out of the light.

Denaturalizing solution for samples: 0.72 mL of 10×MOPS, 3.6 mL of 98% formamide, 1.17 mL of 37% formaldehyde and 0.51 of $H_2O$. Filter. Prepare a new solution every 3 months.

Loading buffer: 1 mL of 10×MOPS, 2.5 g of Ficoll, 5 μg of Bromophenol Blue, $H_2O$ until 10 mL.

1. Prepare the gel as follows: weigh 1.87 g of agarose (GCG-FMC), add 24 mL of elution buffer 10× and 168.8 mL of $H_2O$. Boil in the microwave until all the agar has melted. Cool to 60° C. and add 39.2 mL of 37% formaldehyde and mix. Place the agar in a Maxi-Protean equipment (Bio-Rad) with small polished glass (33×16) and teeth comb. Let the gel polymerize for 1 hour.

2. Preparation of the samples: in an eppendorf take 20 μg of total RNA dissolved in water per sample. Dry the samples in a rotatory evaporator and afterwards add 5 μL of ribonuclease-free water, prepare the markers of RNA (5 μL) as with the other samples. Add 20 μL of denaturation solution from the samples. Heat to 60° C. in a bath for 15 min and cool in ice immediately after. Add 10 μL of samples' buffer.

3. Prepare 3 litres of elution buffer and assemble the electrophoresis equipment. Load the samples with the help of an automatic pipette. Make the electrophoresis run at 70–80 V for 3 h approximately.

4. Extract the gel of the equipment and treat in a heater at 65° C. in H$_2$O treated with DEP (previously kept at 65° C.) for 30 min to eliminate the formaldehyde in the gel.

5. Cut the track corresponding to the molecular weight markers of and dye for 20 min with ethidium bromide. Unstain overnight and photograph.

4.2. Transfer

Besides the above mentioned material, in this Section, a 20×SSC solution is employed.

1. Cut the nitrocellulose filter (Schleicher & Schwell, Germany) or the Nylon filter (Amersham) to the size of the gel, three pieces of Whatman paper nr. 1 of the same size and two pieces of 33×16 cm.

2. Prepare 1 liter of 10×SSC. Submerge the filter in the solution. Place the solution 10×SSC in the tray, cover with the glass and the two Whatman papers which have to reach the bottom of the tray. Put the gel over it and, then, the filter (of nitrocellulose or nylon); eliminate the bubbles between the gel and the filter with the help of a pipette. Cover with three Whatman papers eliminating the bubbles each time and place paper napkins over these. The whole is then wrapped in transparent paper to avoid evaporation and a weight of approximately 1 Kg is placed over the paper.

3. Leave to transfer overnight.

4.3. RNA Fixing in the Filter

In the case of nitrocellulose filters, the process is as follows: the filter is taken out of the transfer and it is dried with filter paper. Afterwards, it is placed in the vacuum oven at 80° C. from 2–4 h. The filter may be kept in this way wrapped in filter paper until it is needed again. If nylon filters are used, it is not necessary to dry them after the transfer.

To fix the RNA, the filter is wrapped in transparent paper and it is placed in the U.V. light transluminator for 5 min facing the side with the RNA to the light. The filter is kept wrapped and humid ready for use. The nylon filters used make it possible for us to fix the RNA more efficiently than with nitrocellulose and may be used again with minor RNA losses.

4.4. Radiactive Labeling of the Probe

The protocol followed for the labeling of the probes with $^{32}$P is the one described by Feienberg, A. P., and Volgestein, B. (1983) *Anal. Biochem.*, 132: 6–13, which is detailed as follows:

TM solution: 250 mM Tris-HCl, 25 mM MgCl$_2$, 50 mM β-mercaptoethanol, pH 8.

DTM solution: 100 μM dATP, dTTP and dTGP in TM solution.

OL solution: 1 mM Tris and 1 mM EDTA pH 7.5+90 units/mL of oligodeoxyribonucleotides.

LS solution: 1M Hepes pH6.6: DTM: OL (25:25:7). Stock the aliquots at −20° C.

Stop solution: 10 mM EDTA, 1% SDS.

NET buffer: 100 mM NaCl, 10 mM Tris-HCl pH 7.6.

BSA Fraction V (Boehringer Mannheim, Germany) 10 mg/mL.

(α-$^{32}$P) dCTP 3000C1/mmoL, 10.0 mCi/mL (Amersham).

t-RNA (Serva, Germany) 10 mg/mL.

Molecular biology grade Sephadex G-100 (Pharmacia, Sweden).

Scintillation solution (Cytoscint TM, ICN Biomedicals Inc., USA).

2M sodium acetate pH 5.0.

1. Put between 50 and 100 μg of $^{32}$P in an eppendorf (5 μL). Dry in a rotatory evaporator for 10 min. Add 5.7 μL of LS and 1 μL of BSA.

2. Add 75 ng of probe to an eppendorf and top it up to 6.6 μL with sterile water. Make a hole in the top of the eppendorf, boil for 3–5 min. Cool in ice.

3. Add the probe to the eppendorf tube with $^{32}$P, LS and BSA.

4. Add 1 μL of DNA polymerase (Klenow), mix the contents by shaking lightly and centrifuge for a few seconds. Keep at room temperature overnight.

5. Add 25 μL of stop solution and 5 μL of t-RNA.

6. Separate the labeled probe of the free $^{32}$P-dCTP in a column of Sephadex G-100 of 5 mL in Net buffer prepared in a sterile plastic pipette of 10 mL. Load the reaction mixture and elute with NET buffer. Take 10 fractions of 0.5 mL.

7. Take 10 μL from each fraction and add 2 mL of scintillation solution, mix and read in the scintillation counter.

8. Take the first peak, add 50 μL of 2M sodium acetate pH 5 and 1 mL of ethanol to each eppendorf. Keep at −80° C. for 30 min.

9. Centrifuge at 10,000 rpm at 4° C. for 15 min. Discard the supernatant, dry the pellet and suspend again in 100 μL of TE.

10. Mix 5 μL of each eppendorf with 2 mL of scintillation solution and read the samples in the scintillation counter. Estimate the number of countings per μL.

4.5. Prehybridization

20×SSEP: 179 g of NaCl, 27.6 g of NaH$_2$PO$_4$.H$_2$O, 7.4 g EDTA and H$_2$O until 500 mL. Treat with DEP and sterilize.

50×Denhardts Solution: 5 g of Ficoll, 5 g of polyvinylpyrolidone, 5 g of BSA fraction V, and H$_2$O until 500 mL. Treat with DEP. Aliquot and freeze.

Prehybridization solution: 1 g of glycine, 1 mL of 20% SDS, 25 mL of 20×SSPE and 10 mL of 50×Denhardts Solution; top up to 100 mL with H$_2$O treated with DEP. Prepare just before use.

1. Place the filter in a hybridization bag. Add 50 mL of the prehybridization solution per filter. Eliminate the bubbles and seal the bag hermetically. Let it incubate in a bath overnight at 42° C. while being shaken.

4.6. Hybridization

20×SSPE.

50×Denhardts solution.

t-RNA: 10 mg tRNA (Serva, Germany) per mL of water treated with DEP.

Hybridization solution: 0.1 g of glycine, 2.5 mL of 20×SSEP, 0.1 mL of 20% SDS, 0.5 mL of 50×Denhardts solution, 0.25 mL of t-RNA (10 mg/mL), 4.5. mL of formamide and 2.05 of ribonuclease-free water. Prepare just before use.

1. Extract the filter from the bag and place it in Whatman paper to eliminate the remains of the prehybridization solution. Leave the filter in the paper for 5–10 min at the most and place in a new hybridization bag.

2. Prepare the hybridization solution. Take the labeled probe and estimate 1×10$^7$ cpm per filter. Place the probe in an eppendorf, make a hole in the top and boil for 3 min. Cool it quickly in ice. Add the probe to 3 mL of hybridization solution.

3. Add the solution with the denaturalized probe to the bag which contains the filter. As the solution is radioactive, you must very carefully eliminate the bubbles with the help of a pipette. Seal the bag.

4. Incubate in a bath overnight at 42° C. while being shaken.

4.7. Washings

20×SSC.

20% SDS.

1. Dry the filter of the bag with care and place in Whatman paper to eliminate the remains of the hybridization solution. Put the filter in a tray while shaking to start the washings.

2. Washings:
  a) 2×SSC (50 mL 20×SSC), 0.5% SDS (12.5 mL 20% SDS) in 500 mL. Incubate for 5 min at room temperature. Repeat once.
  b) 1×SSC (25 mL 20×SSC), 0.5% SDS (12.5 mL 20% SDS) in 500 mL. Incubate for 30 min at room temperature.
  c) 0.5×SSC (12.5 mL 20×SSC), 0.5% SDS (12.5 mL 20% SDS) in 500 mL. Incubate for 30 min at room temperature.
  d) 0.1×SSC (2.5 mL 20×SSC), 0.5% SDS (12.5 mL 20% SDS) in 500 mL. Incubate for 30 min at 42° C.

4.8. Autoradiography

Once the filter has been washed, it is placed in Whatman paper, the remains of the solution are eliminated and, in the case of nitrocellulose filters, it is put to dry in the open air. Nylon filters are not dried.

Afterwards, the filter is wrapped in transparent paper and it is placed in an exposure cassette with a Kodak X-OMAT AR film (USA) with two amplifying plates, the face which contains the RNA facing the film. The film is impressed by placing the cassette at −80° C. for the required time. The autoradiography is developed in the dark room with Kodak developer solution. The developing is stopped in acetic at 10% and it is set with Kodak fixing solution. The film is washed with water and it is dried in the open air.

4.9. Elimination of the Probe

The filters, once autoradiographed, may be reused after the elimination of the marked probe of the filter and may undergo hybridization. To do that, the following method is employed:

1. Place the filter in a new hybridization bag with 50 mL of ribonuclease-free water (treated with DEP and sterile) at 65° C. Seal the bag so that no bubbles remain inside.

2. Place the bag on a tray with boiling water.

Maintain the bag at 100° C. for 5–10 min while being shaken.

3. Extract the filter from the bag and dry it in the open air if we are dealing with nitrocellulose filters. Wrap the filter in transparent paper and expose overnight at −80° C. in the previously described conditions.

4. Verify that there is no labeling. The filter may be hybridized again.

4.10. Beta Emission Counting

The quantifying of the hybridized filters with the respective probes was done using a Betascope 601 blot Analyzer counter (Betagen, USA). The counting time was 45 min for the hybridized filter with the probe p53 and $\beta_2$-microglobuline and 2 h for the trypsin probe.

In Table 18, which is presented next, the results obtained for each of the probes in the beta counter in absence and in presence of PCI may be observed.

Assuming that the counts of the $\beta_2$-Microglobuline are an indication of the total amount of poly($A^+$) RNA, the data may be standardized as a percentage of counts of the band compared to the $\beta_2$-microglobuline counts of the same cells, giving a value which depends on the abundance of the specific mRNA in relation to the total of mRNA. The results are presented in Table 19.

TABLE 18

Results of beta counts corresponding to the Northerns of the Capan-1 cells, from the various treatments hybridated with p53, trypsin and $\beta_2$-microglobuline probes.

| Treatment | p53 | Trypsin | $\beta_2$-microglobuline |
|---|---|---|---|
| Control | 138 | 511 | 955 |
| 1 mg/mL PCI | 882 | 396 | 2183 |
| 10 mg/mL PCI | 1111 | 432 | 6287 |

TABLE 19

Counts of one band in relation to those of $\beta_2$-microglobuline

| Treatment | p53/$b_2$ | Trypsin/$b_2$ |
|---|---|---|
| Control | 0.1445 | 0.5351 |
| 1 mg/mL PCI | 0.4040 | 0.1814 |
| 10 mg/mL PCI | 0.1767 | 0.0687 |

From these data we can evaluate the relative abundance of a mRNA in the cells treated compared to the control group cells. Thus, in Table 20, the results obtained of the ratio between the standardized number of counts for a treatment and the number of counts of the control group cells are presented.

In short, when the cells are treated with a concentration of 1 μg/mL of PCI, the level of transcription of the mRNA of p53 increases 2.8 times and the level of trypsin diminishes 2.9 times. For the treatment with 10 μg/mL, it increases 1.2 the transcription of the mRNA of p53 and it decresases 7.8 times that of trypsin.

These results indicate that the treatment with PCI provokes a higher transcription of p53. Until now, such transcription level has been described for situations of cell stress such as ultraviolet and gamma radiations, heat, lack of serum in the culture medium of the cells or any carcinogen (Bates, S. & Vousden, K. H. (1996) *Curr. Opin. Genet. Develop.*, 6: 12–19). An increased level of protein p53 provokes either an induction of apoptosis or a halting in $G_1$. According to the results expressed in Sections 4.F.2. and 4.F.4, a great increase of apoptosis has not been observed; however, an increase of the number of Capan-1 cells in $G_1$ when treated with PCI has been observed. Leaving aside problems of heterogeneity of the cell line among laboratories, such cell line presents a muted p53 (Barton, C. M. et al. (1991) *British J. Cancer*, 64: 1076–1082; Berrozpe et al. (1994) *Int. J. Cancer.*, 58:185–191). This mutation may annul its potential for inducing apoptosis but not its power for halting in $G_1$ (Rowan et al (1996) *EMBO J.* 15: 827–838). In fact, this is what we are observing when treating the cells of the line Capan-1 with PCI.

TABLE 20

Quantification of the higher or lower transcription of p53 and trypsin in cells treated with various concentrations of PCI in relation to the control group cells.

| Treatment | p53 | Trypsin* |
|---|---|---|
| 1 mg/mL PCI | 2.8 | 2.9 |
| 10 mg/mL PCI | 1.2 | 7.8 |

TABLE 20-continued

Quantification of the higher or lower transcrition of p53 and trypsin in cells treated with various concentrations of PCI in relation to the control group cells.

| Treatment | p53 | Trypsin* |
|---|---|---|

*In the case of the trypsin probe, since the number of counts of the treated cells is inferior to the number of counts of the control group cells, the inverse quotient has been obtained (control/treatment) and the resulting number indicates the times that the transcription of the mRNA is inhibited by the said protein.

Thus, the treatment with PCI brought about a great decrease in the transcription of the trypsin gene, a typical protein of the acinar type (Koivunen, E. et al (1991) *Cancer Res*, 51:2107–2122).

4.F.6. Studies on Competitive Binding of the PCI to Growth Factor Receptors

With the aim of determining whether the PCI binds growth factor receptors, tests of competitive binding were carried out, for it had already been verified that the PCI was quickly and massively internalized. The possible binding of the PCI to the receptor has been studied for epidermic growth factor (EGF), since it has been proved that PCI and EGF are knotins which share a common structural core called cystine-Knot (Lin, S. L. & Nussinov, R. (1995) *Nature Med.*, 2: 835–837; Sun, P. D. (1995) *Annu. Rev. Biphys. Biomol. Struct.*, 24: 269–91). A standard protocol of binding has been followed according to the work done by Reiss, M. et al. (1991) *Cancer Res.*, 51: 6254–6262, with some modifications which are detailed below.

Apart from the material described in Section 4.B.1., the materials and solutions required for carrying out the binding test are detailed as follows:

Binding medium: DMEM–0.3% BSA–20 mM Hepes pH 7.4.

EGF: a 12 μM stock solution is prepared in a 20 mM Hepes buffer–0.3% BSA. Further dilutions are made in the binding medium. (ICN, USA.)

$^{125}$I-EGF: a stock solution in a 20 mM Hepes buffer–0.3% BSA is prepared. Further dilutions are made in the binding medium. (ICN, USA.)

PCI: a stock solution 1 mg/mL is prepared in milliQ grade $H_2O$ and further dilutions in binding medium.

Washing solutions: PBS–0.1% BSA.

Permeabilization solution: 1N NaOH–0.1% SDS.

Gamma counter (LKB, Sweden).

The studies on competitive binding of the PCI to the receptor for epidermic growth factor (EGF-R) were carried out with the human pancreatic adenocarcinoma cell line Capan-1. The detailed procedure that was employed is as follows:

1. 1.25×10$^5$ cells were seed per well in plates of 24 wells which were kept in culture for 48 h in DMEM FBS 10%. Triplicates were put for each concentration of competitor to be tested.

2. 24 h before the test, the full medium of the wells was replaced by 2 mL, per well, of DMEM without fetal serum.

3. The next day, the cells were washed, three times, with cold binding medium.

4. The cells were incubated with 70 μL of binding medium to which the concentrations of the competitor to be tested had been added. In the case of the EGF, the tested concentrations were 0, 0.005, 0.01, 0.1, 1, 10 and 100 nM. For the PCI, the tested concentrations were 0, 2.32 nM, 23.28 nM, 232.8 nM, 2328.2 nM, 11641.4 nM and 46565.7 nM which were previously used in the proliferation tests. Afterwards, 40,000 cpm (350 pM) of $^{125}$I-EFG were added. The incubation was done at 4° C. for 5 h. To determine the unspecific binding, in the case of competition with unlabeled EGF as well as with PCI, control wells were incubated with an excess of 100 times molar of unlabeled EGF (100 nM) compared to the tested $^{125}$I-EGF.

5. The cells were washed quickly three times with 500 μL of the cold washing solution.

6. They were solubilized through incubation for 30 min at room temperature with the permeabilization solution.

7. The radioactivity in the suspension was determined with a gamma counter. To determine the unspecific binding, the value of unspecific binding was deducted from the total bounded radioactivity.

In the first place, a competition between the 125I-EGF and the unlabeled EGF was carried out; this test would allow us to determine if the cell line under study, Capan-1, presents one or more types of receptor for this growth factor. From the test, the bounded radioactivity for each one of the tested concentrations of unlabeled competitor was determined. The results obtained are shown in Table 21. From these data, the binding percentage of binding (P) was determined, where 100% is the amount of specific union in absence of competitor ($B_0$). To determine the percentage, the following formula was applied:

$$P = \frac{B \times 100}{B_0}$$

where B is the amount of specific binding in presence of a specific competitor concentration.

Figure 23:
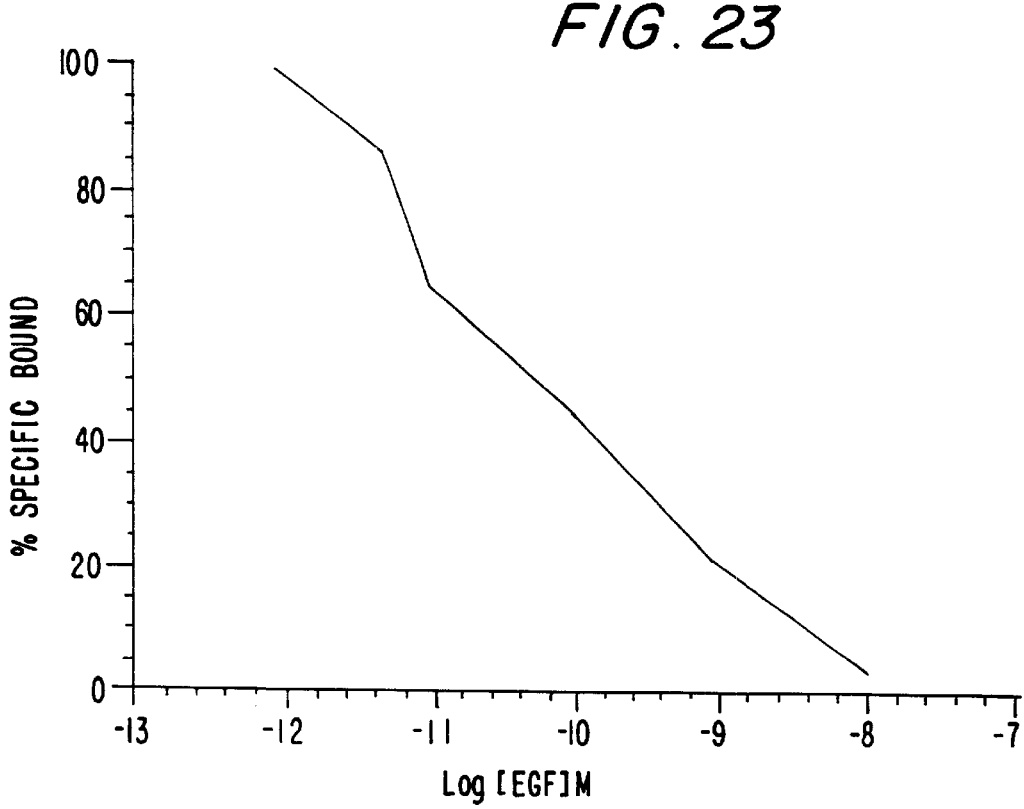
FIG. 23: Competition of cold EGF and $^{125}$I-EGF. The logarithm of the inhibitor concentration is represented versus the percentage of the specific union. Cells of the human pancreatic adenocarcinoma cell line Capan-1 were incubated with increasing concentrations of EGF in the presence of 350 pM of $^{125}$I-EGF for 5 h at 4° C.

In FIG. 23 it is observed that when representing the log [EGF] versus the binding percentage, the result is not a straight line. This result indicates that the EGF joins two types of receptors, one of high affinity and the other of low affinity. With the aim of determining the kind of binding which is taking place, a pseudo-Hill or Logit-log representation (Pratt, W. B. and Taylor, P. "Principles of Drug Action. The Basis of Pharmacology". Ed. Churchill Livingstone, N.Y., 1990) was carried out. The data of specific binding percentage are used to calculate the log(P/[100-P]), which is represented versus the logarithm of the competitor concentration.

TABLE 21

Competition of the EGF and $^{125}$I-EGF for the EGF receptors of the Capan-1 cell line.

| [EGF] nM | log [EGF] M | Specific binding (cpm) | Standard Deviation | Percentage of specific binding |
|---|---|---|---|---|
| 0.00001 | −12 | 1896.2 | 94.9 | 99.9 |
| 0.005 | −11.3 | 1641.5 | 85.0 | 86.57 |
| 0.01 | −11 | 1224.8 | 86.9 | 64.59 |
| 0.1 | −10 | 844.50 | 171.9 | 44.53 |
| 1 | −9 | 395.5 | 43.27 | 20.33 |
| 10 | −8 | 56 | 10 | 2.95 |

The resulting slope of the straight line is called pseudo-Hill coefficient. If this coefficient is equal to −1 it indicates that the competitor binds a unique type of receptor, and if the coefficient is different of −1 it indicates that the data can fit a type of competition with two receptors.

Figure 24:
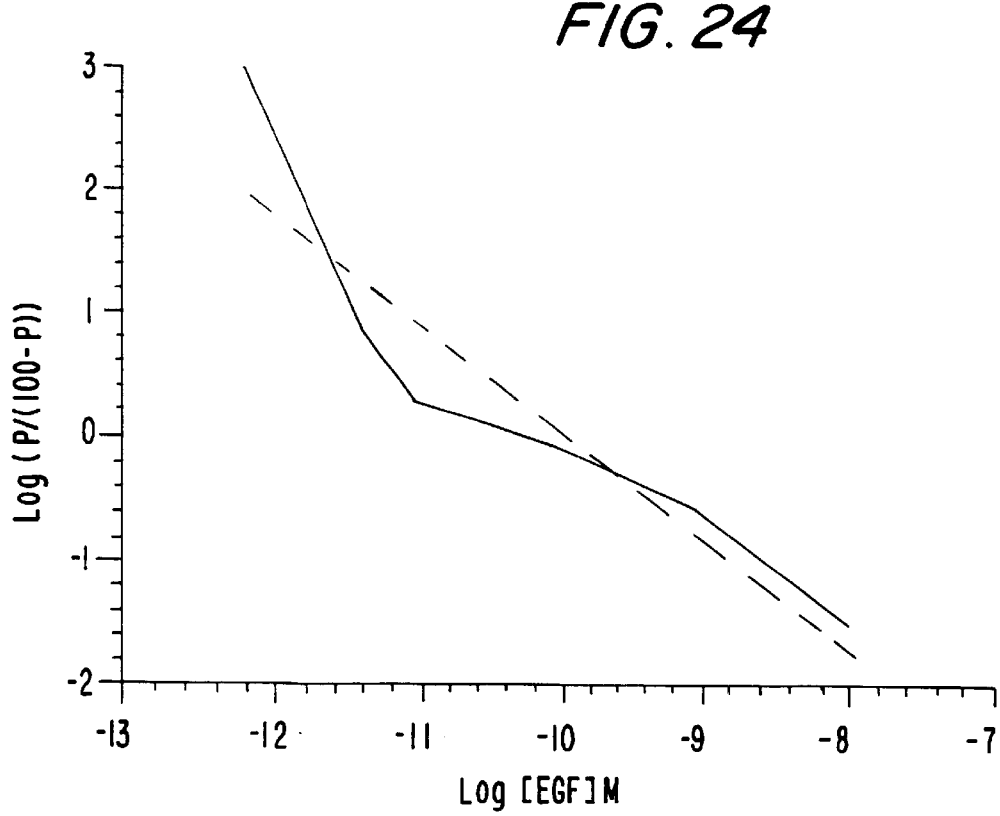
FIG. 24: Representation of Logit-log (pseudo-Hill) of competitive binding EGF/$^{125}$I-EGF. The percentage of specific union P of the competitor, EGF, is used to calculate the log(P/[100−P], which is represented against the logarithm of the competitor concentrations. Values obtained from the data of Table 21.

In Table 22, the values of Logit-log obtained from the original data may be observed and in FIG. 24 the representation of pseudo-Hill may be observed.

The equation of the straight line resulting from the graph is as follows:

$$y = -9.0949 - 0.92058x$$

with a regression coefficient r=0.90804, so that the slope of the straight line is different of −1 and, therefore, it may be considered that the EGF binds two types of receptors which makes it possible to carry out an adjustment of the data for a competition with two binding sites.

TABLE 22

Values for the representation of Logit-log.

| Log [EGF] M | Log (P/[100-P]) |
|---|---|
| −12 | 2.99 |
| −11.3 | 0.809212 |
| −11 | 0.2610825 |
| −10 | −0.095292 |
| −9 | −0.579147 |
| −8 | −1.516677 |

Figure 25:
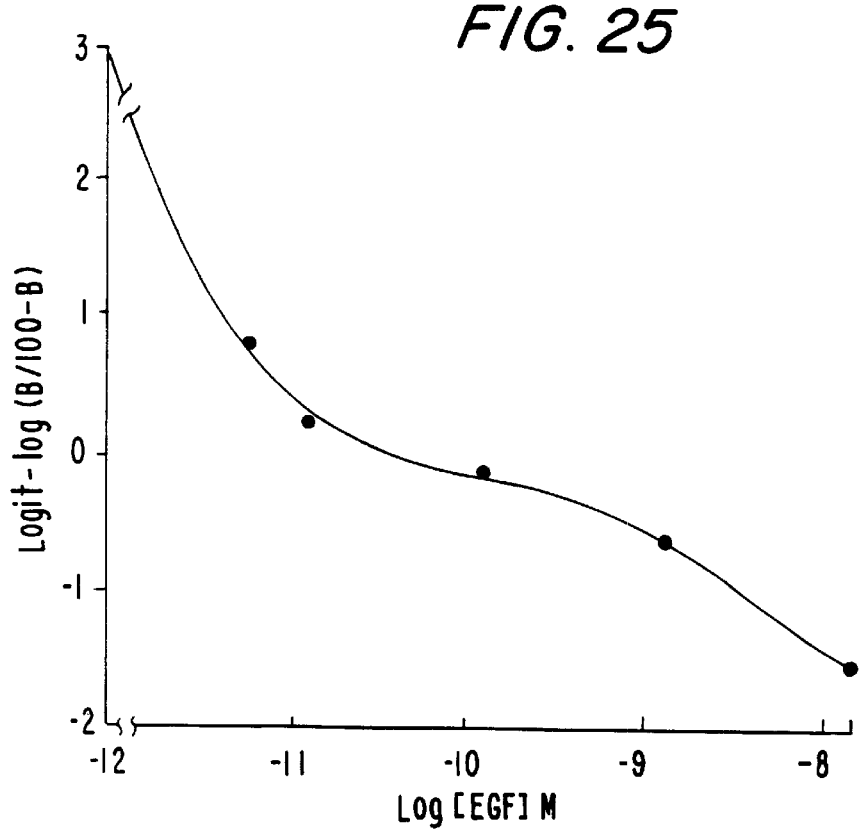
FIG. 25: Representation of Logit-log of the competition curves of cold EFG and $^{125}$I-EGF for the human pancreatic adenocarcinoma cell line Capan-1. The points have been fitted with the programme "Graphpad Inplot4" to a model of competition between two different binding sites. Each value has been determined in triplicate and, in the graph, the average value is represented. (B is equal to the percentage of specific union).

The fitting has been made using the programme Graphpad Inplot4. A non-linear fitting for competition for two binding sites is made. The logarithm of the competitor concentration has been represented versus the values of Logit-log (FIG. 25).

From the previous fitting, the value of $IC_{50}$, that is to say, the competitor concentration which inhibits 50% of the specific binding for the two types of binding was determined. Also, the percentage of the two types of binding sites was determined. The results are presented in Table 23.

Once the receptor types of the Capan-1 cells for the EGF have been characterized, a study of competition between the PCI and the $^{125}$I-EGF was performed to verify whether the PCI competes for the same receptors as the EGF. As for the previous study of competition between $^{125}$I-EGF and EGF, the bounded radioactivity for each of the tested concentrations of PCI was determined.

TABLE 23

Percentage of the two types of binding sites of the EGF in its receptors in Capan-1 cells.

| Binding site | IC50 | % Receptors |
|---|---|---|
| High affinity | 0.6 pM | 82.3 |
| Low affinity | 2.82 nM | 17.8 |

The results obtained are presented in Table 24. From these original data, the binding percentage (P) was determined.

TABLE 24

Competition of the PCI in front of $^{125}$I-EGF for EGF receptors of the Capan-1 cell line.

| [PCI] nM | log [PCI] M | Specific binding (cpm) | Standard Deviation | Percentage of specific binding |
|---|---|---|---|---|
| 1 | −9 | 1597 | 100 | 99 |
| 2.32 | −8.63 | 1503.5 | 130 | 94.14 |
| 23.2 | −7.63 | 1307 | 117 | 83.78 |
| 232.8 | −6.63 | 1250 | 212 | 80.13 |
| 2328.2 | −5.83 | 621.5 | 21.9 | 39.38 |

TABLE 24-continued

Competition of the PCI in front of $^{125}$I-EGF for EGF receptors of the Capan-1 cell line.

| [PCI] nM | log [PCI] M | Specific binding (cpm) | Standard Deviation | Percentage of specific binding |
|---|---|---|---|---|
| 11641 | −4.93 | 582.6 | 86.19 | 37.35 |
| 46566 | −4.33 | 543.33 | 88.75 | 34.83 |

Figure 26:
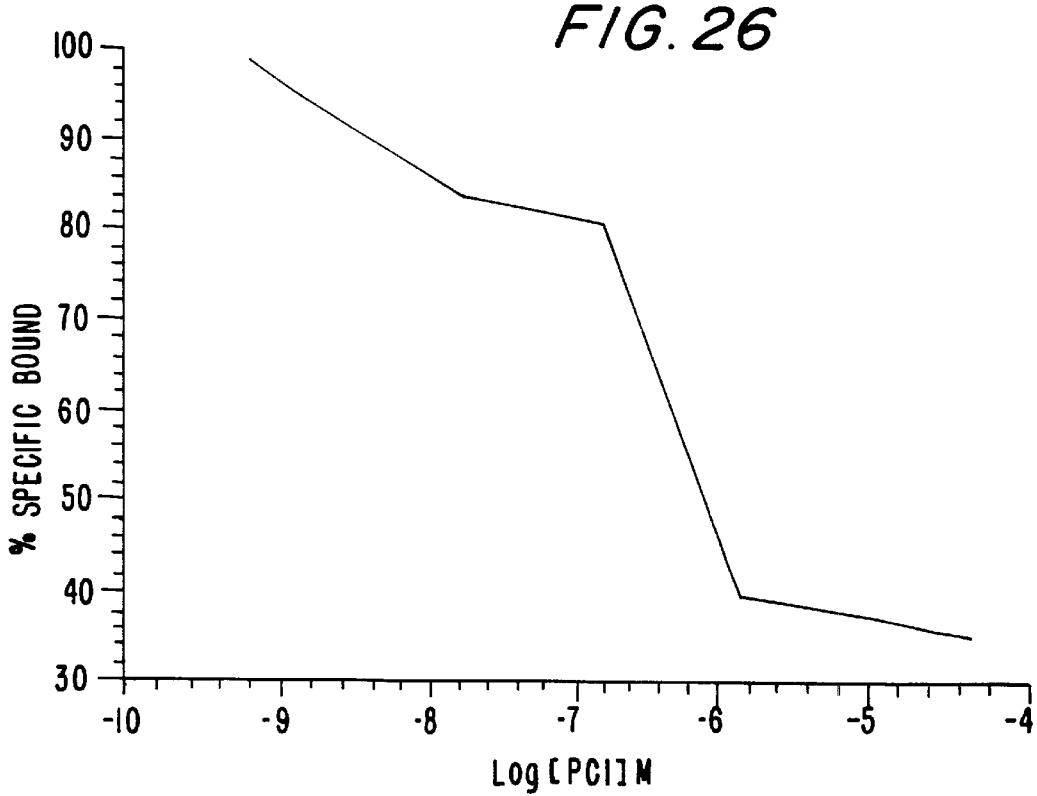
FIG. 26: PCI competing with $^{125}$I-EGF. The logarithm of the concentration of inhibitor is represented versus the percentage of specific binding. Cells of the human pancreatic adenocarcinoma cell line Capan-1 are incubated with increasing concentrations of PCI in the presence of 350 pM of $^{125}$I-EGF for 5 h at 4° C.

In FIG. 26, the results expressed in Table 24 are represented. It can be seen that, when representing the log (PCI) versus the percentage of binding in the EGF-type receptors in Capan-1 cells, it does not result in a straight line. This seems to indicate that the PCI is binding two types of receptors, one of high affinity and the other of low affinity.

In this case, a pseudo-Hill or Logit-log representation was also made to calculate the coefficient of pseudo-Hill and verify whether the PCI binds two receptors for EGF which the Capan-1 cells show.

Figure 27:
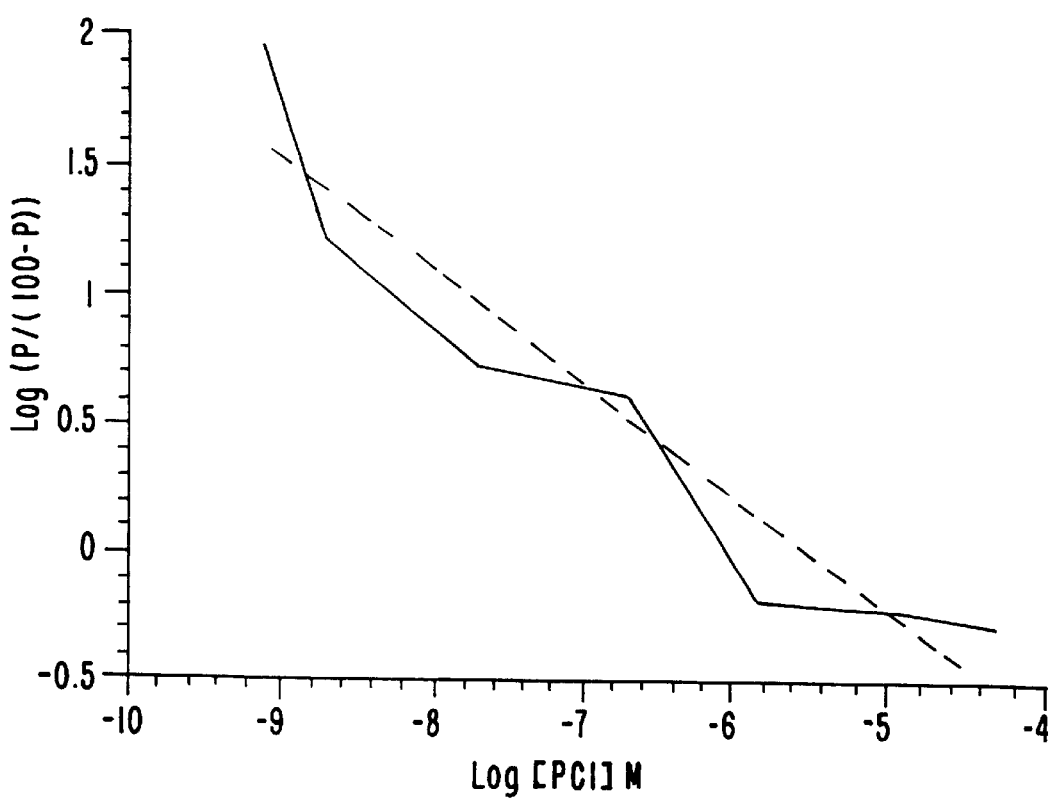
FIG. 27: Representation of Logit-log (pseudo-Hill) of competitive binding $^{125}$I-EGF/PCI. The percentage of specific union P of the competitor, PCI, is used to calculate the log(P[100−P], which is represented versus the logarithm of the competitor concentrations. Values obtained from the data of Table 24.

In Table 25, the values of Logit-log obtained from the original data may be observed and in FIG. 27 the pseudo-Hill representation is shown.

TABLE 25

Values for the Logit-log representation.

| Log [PCI] M | Log (P/[100-P]) |
|---|---|
| −9 | 1.99 |
| −8.63 | 1.205 |
| −7.63 | 0.713 |
| −6.63 | 0,605 |
| −5.83 | −0.1873 |
| −4.93 | −0.2246 |
| −4.33 | −0.272 |

The equation of the straight line resulting from the graph is as follows:

$$y = -2.4589 - 0.44789x$$

with a regression coefficient of r=0.94546

It is observed that the slope of the obtained straight line is different from −1 thus indicating that PCI is binding two different types of receptors and that it is correct to make the fitting of the data for a competition with two binding sites.

Figure 28:
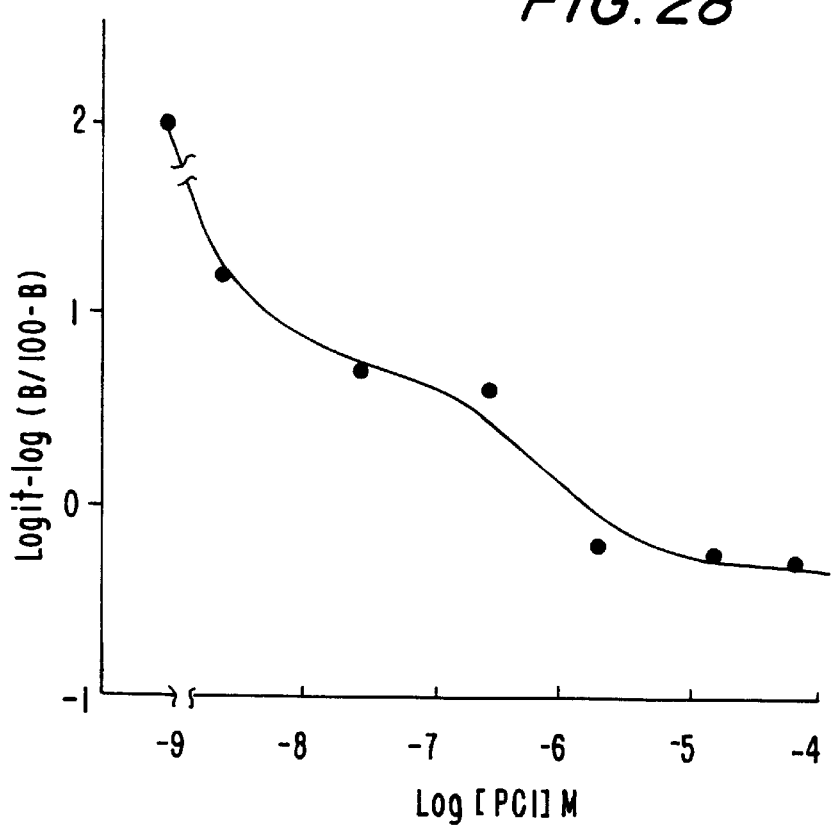
FIG. 28: Representation of Logit-log of the competition curves of the PCI and $^{125}$I-EGF for the human pancreatic adenocarcinoma cell line Capan-1. The points have been fitted with the programme "Graphpad Inplot4" to a model of competition between two different binding sites. Each value has been determined in triplicate and in the graph, the average value is represented. (B is equal to the percentage of specific binding.)

Afterwards, a representation (by means of the programme Graphpad Inplot4) with a non-linear adjustment to analyze the competition for two binding sites was carried out as had already been done for the EGF, representing the logarithm of the competitor concentration and the values of Logit-log shown in FIG. 28.

From the previous adjustment, the value of $IC_{50}$ for the two binding sites and the percentage of each type of binding sites was determined. The results are shown in Table 26.

TABLE 26

Percentage of the two types of binding sites.

| Binding site | $IC_{50}$ | % Receptors |
|---|---|---|
| High affinity | 13.96 pM | 99.7 |
| Low affinity | 0.579 mM | 0.3 |

The results described indicate the existence of two types of receptors for the EGF in the Capan-1 cells: one of low affinity and the other of high affinity; the values of $IC_{50}$ obtained for such receptors coincide with the results described in the literature (Groenen, I. C. et al. (1994) *Growth Factors*, 11: 235–257). The PCI competes with the $^{125}$I-EGF to join the receptor of such growth factor; the displacement of EGF generated by the presence of PCI is, for the most part, produced in the receptor of high affinity, the binding capacity of the PCI to such receptor being 6 times inferior to that of the EGF.

4.F.7. Study of Basal Phosphorilation of the EGF Receptor Under the Stimulus of EGF Alone or Plus PCI in the A431 and Capan-1 Cell Lines Once determined that the PCI binds the receptor of EGF by means of studies of competitive binding with the afore mentioned receptor, we began to study whether the PCI acted as an antagonist of the EGF inhibiting the phosphorilation of the receptor of the said growth factor, in its basal condition as well as under stimulation from the very same EGF. The material and protocol used have been those described by Donato, N. J. et al. (1989) *J. Cell. Biochem.*, 41: 139–157.

This type of experiments were done with two different cellular lines: A431 and Capan-1; the first one is a squamous cancer cell line which has a very high number of EGF receptors (Reiss, M. et al. (1991) *Cancer Res.*, 51: 6254–6262) and the second was the human pancreatic adenocarcinoma cell line in which we observed that the PCI competes with the EGF for the receptors of the said factor.

In addition to the material detailed in Sections 4.B.1. and 4.B.2., the material used was the following:

1M buffer of sodium phosphate pH 7.4: it was prepared by mixing 19 mL of 1M $NaH_2PO_4$ with 8 mL of 1M $Na_2HPO_4$.

Lysis buffer RIPA B: its composition is 20 mM buffer sodium phosphate pH 7.4, 1% Triton X-100, 150 mM NaCl and 5 mM EDTA. This solution is kept at 4° C.

Solution of leupeptin: a stock 10 μg/mL is prepared and kept at −20° C.

Solution 250 mM of sodium vanadate; it is kept at −20° C.

ICKA buffer: its composition is 10 mM sodium phosphate buffer pH 7.4, 150 mM NaCl and 0.1% Triton X-100. This solution is kept at 4° C.

Solution 100 nM $MnCl$. This solution is kept at 4° C.

Hepes vanadate buffer: its composition is 20 Mm Hepes pH 7.4. and 100 μM sodium vanadate.

Buffers for a polyacrylamide gel electrophoresis (PAGE-SDS) (Laemmli, U. K. (1970) *Nature*, 227: 680–685).

Solutions 2×, 3× or 5× of loading buffer for PAGE-SDS. Add 5% of β-mercaptoethanol just before use.

Solution 1M KOH. This solution is kept at room temperature.

Setting solution: 40% methanol and 10% acetic acid.

The method employed was as follows:

1. Preparation of the Cells to be Lysed 1.a. Culture the cells in petri dishes of 100 mm until reaching 70% of confluence.

1.b. Wash the cells twice with PBS tempered to 37° C. Next, add serum-free medium and let them grow for 18 h.

1.c. Wash the cells twice more with tempered PBS and add new serum-free medium. Immediately after, add PCI to the concentration which is going to be studied in the cultures to be treated and incubate for 10 min at 37° C. Next, add EGF to the cultures (5 ng/mL in the case of the Capan-1 cell line and 1 ng/mL for the A431 cell line) and incubate again for 10 min at 37° C.

1.d. Remove the culture medium and wash twice with cold PBS.

1.e. Prepare the RIPA B buffer: prepare a solution of PMSF 200 mM in ethanol. Add to the incomplete RIPA buffer (the one described in material) PMSF at a final concentration 5 mM, adjust the pH to 7.4. with 1M NaOH and filter the solution through a filter of 0.22 μm. Then, add at 1% (v:v) aprotinine, 10 μg/mL of leupeptine and 250 μg/mL of sodium vanadate. Maintain the solution of RIPA B in ice.

1.f. Add 0.5 mL of RIPA B to each plate. Detach the cells with a scraper.

1.g. Transfer the cell lysate to glass homogeneizing tubes previously cooled in ice. Homogenize 50–60 times.

1.h. Transfer to corex tubes of 15 mL previously cooled and centrifuge at 10,000 rpm for 10 min at 40° C.

1.i. Transfer the supernatant to eppendorfs and keep them in ice. Discard the pellets.

1.j. Determine the concentration of protein using the Bradford method (Bradford, M. M. (1976) *Anal. Biochem.*, 72: 248–254), diluting the samples 1:100 in water and adding the same volume of RIPA B as the volume of the sample in the dilutions to the standard tubes.

1.k. Calculate the volume of cell lysate required to obtain 250 μg of protein. Top up to 300 μL with RIPA B. Start with immunoprecipitation.

2. Immunoprecipitation 2.a. Add 5 μL of antibody for the EGF receptor (EGFR) to each sample and mix using a vortex. Incubate for 1 h in ice.

2.b. Add 50 μL of pansorbine to each sample and mix by using a vortex. Incubate for 20–30 min in ice.

2.c. Centrifuge at 13,000 rpm for 2 min at room temperature, Discard the supernatant.

2.d. Mix the pellets with a vortex and resuspend again in 1 mL of cold ICKA buffer.

2.e. Repeat steps 2.c. and 2.d. three times.

2.f. Dry the pellets with absorbant paper. Leave the pellets in ice and immediately start kinase activity test, or freeze the pellets for a short time at −70° C.

3. Kinase Activity Test Employing Immune Compounds 3.a. Prepare the reaction buffer. Each sample requires 50μL.

3.a.1. Determine the amount of cofactor ($Mn^{2+}$) to be added. The final concentration has to be 8 mM (the stock is 100 mM).

3.a.2. Calculate the required $^{32}$P-ATP. Each sample requires 10 μCi.

3.a.3. Fill up with Hepes-vanadate buffer.

3.b. Mix the dried pellets with vortex and resuspend each one again in 50 μL of the reaction buffer which has just been prepared.

3.c. Shake vigorously. Incubate for exactly 10 min at room temperature.

3.d. Stop the reaction by adding 2×, 3× or 5× of the loading buffer with␣8-mercaptoethanol. Mix the pellets well. Boil the samples for 5 min at 100° C. together with the molecular weight markers.

3.e. Centrifuge the samples at 13,000 rpm for 2 min at room temperature.

3.f. Put the samples in a 8% gel for SDS-PAGE. Discard the pellets.

3.g. Run the gel overnight at 50–60V or alternatively let it run for 3–4 h at 40–50 mA with a cooling system.

3. h. Fix the gel in the fixing solution for 30–60 in.

3.i. Boil the gel in 1M KOH for 20 min.

3.j. Transfer the gel to the fixing solution. Keep it there changing the solution every 5–10 min until the gel returns to its normal size and is transparent instead of white. Normally it lasts 30–60 min.

3.k. Dry the gel (for at least 3 h) and autoradiograph it for 10 min for the A431 cell line and 2–4 h for the Capan-1 cell line. Count the radiactivity of the filter using a beta counter.

The results obtained for the basal phosphorilation of the A431 cell line are summarized in Table 27. The kinase activity in absence of PCI (basal) is taken as 100% and the values of kinase activity have been compared in various concentrations of PCI in relation to this basal activity.

TABLE 27

Basal kinase activity of the EGF receptor after 10 min of PCI treatment of A431 cells.

| Incubation with PCI (mg/mL) | Kinase activity (%) |
| --- | --- |
| 0 | 100 |
| 1 | 68 |
| 50 | 80 |
| 50 | 78 |
| 50 | 61 |
| 100 | 29 |

As we can see, the PCI clearly decreases the basal kinase activity of the EGF receptor of the A431 cells. This inhibition of the kinase activity of the receptor is higher as the PCI concentration increases and oscillates between 20 and 70%.

For Capan-1 cells, the results of basal kinase activity are presented in Table 28; as for A431 cells, the kinase activity in absence of PCI is taken as 100% and the kinase activity of the cells treated with PCI is compared with the latter.

TABLE 28

Basal kinase activity of the EGF receptor after treatment of Capan-1 cells for 10 min with PCI.

| Incubation with PCI (mg/mL) | Kinase activity (%) |
| --- | --- |
| 0 | 100 |
| 50 | 88 |
| 50 | 90 |
| 50 | 70 |

For the Capan-1 cell line, we tested only an incubation with 50 µg/mL of PCI. An inhibition of the basal kinase activity between 10 and 30% was observed.

As for the tests of the kinase activity of the EGF receptor under the incubation with EGF alone or plus PCI, the results for the Capan-1 cells are presented in Table 29. Again, the kinase activity in absence of PCI or EGF is taken as 100% and the kinase activity of the cells treated with EGF alone or with PCI is compared with the latter.

TABLE 29

Kinase activity of the EGF receptor after the treatment of Capan-1 cells for 10 min With PCI and afterwards with EGF 5 ng/mL.

| Sample | Kinase activity (%) |
| --- | --- |
| Control | 100 |
| Treated with 50 mg/mL PCI | 70 |
| Treated with 5 ng/mL EGF | 240 |

TABLE 29-continued

Kinase activity of the EGF receptor after the treatment of Capan-1 cells for 10 min With PCI and afterwards with EGF 5 ng/mL.

| Sample | Kinase activity (%) |
| --- | --- |
| Treated with 5 ng/mL EGF + 1 mg/mL PCI | 180 |
| Treated with 5 ng/mL EGF + 10 mg/mL PCI | 170 |
| Treated with 5 ng/mL EGF + 50 mg/mL PCI | 120 |

As can be seen, the PCI not only inhibits basal kinase activity of the receptor, but also decreases kinase activity induced by the stimulation of the cells with EGF. This inhibition of the kinase activity induced by EGF increases as the dose of PCI also increases, this being 50% in the case of the PCI concentration of 50 µg/mL.

The same kind of test was carried out with the A431 cell line; that is to say, the stimulation of the kinase activity of the EGF receptor induced by EGF and the effect that the PCI has when it is incubated together with the EGF have been studied. The results are presented in Table 30 and the kinase activity has also been taken as 100% in absence of PCI or EGF and it has been compared to the kinase activity of the cells treated with EGF alone or with PCI.

TABLE 30

Kinase activity of the EGF receptor after treatment of A431 cells for ten min with PCI and, afterwards, with EGF 1 ng/mL.

| Sample | Kinase activity (%) |
| --- | --- |
| Control | 100 |
| Treated with 50 mg/ml PCI | 77 |
| Treated with 1 ng/ml EGF | 200 |
| Treated with 1 ng/ml EGF + 1 mg/mL PCI | 126 |
| Treated with 1 ng/ml EGF + 10 mg/mL PCI | 108 |
| Treated with 1 ng/ml EGF + 50 mg/mL PCI | 53 |

For the A431 cells, the PCI produces the same effect as in the case of the Capan-1 cell line, but in this case the inhibitory effect of the kinase activity of the receptor is much more noticeable since for the highest dose of PCI, 50 µg/mL, such activity is reduced to half the basal activity. Therefore, we may conclude that the PCI is an antagonist of the EGF, inhibiting the stimulating action of the EGF.

4.F.8. Computational Analysis to Determine the Topological Relationship Between the PCI and Various Polypeptidic Growth Factors from which it may Appear to be an Antagonist The results obtained with the mutant form PCIdelY37V38G39 indicate that the antitumoral action is not due, for the most part, to the protease inhibitory activity of the PCI but to some structural feature of its globular core. For instance, being related to its knotin topological pattern. To determine this fact, a computational analysis was carried out to establish this relationship using a computational programme elaborated by our research team ("KNOT-MATCH", Mas, J. et al., to be published). This programme allowed us to automatically establish the topological similitude of disulfide bridges from a protein with the existing proteins in the data bank of crystallographic structures (Protein Data Bank, PDB 1996). The programme compared the distances between the geometric centers of each disulfide bridge with the angle between the various intracatenary (or extracatenary) bridges existing in a protein with other of the PDB. Through an alignment routine, sequential or of r.m.s., a selection of those which present r.m.s. inferior to 2 Å was reached.

This analysis led to the following r.m.s. between loops defined by disulfide bridges of PCI and of other molecules as:

TGF-α from 0.65 to 1.46 Å, according to the region
EGF 0.85 Å

It is worth underlining the high degree of structural superposition existing between the PCI (especially loops 18–27 27–34) and the molecules related to growth factors. This coincidence prompted the experiments already detailed in previous Sections (4.B.2.c. and 4.F.6.) which indicate that the PCI presents affinity to the receptors of growth factors. It is also worth underlining the positional physicochemical similarity between EGF and TGF-α amino acids, which have been reported to play a key role in the EGF and TGF-α interaction with the receptor (Groenen, L. C. et al. (1994) *Growth Factors,* 11: 235–257) and those of the PCI. Table 31 shows these results.

TABLE 31

EGF and TGF-a amino acids with important function and their PCI superposition equivalent.

| PCI | P11 | S19 | G20 | W22 | F23 | W28 | N29 | S30 | A31 | R32 | T33 |
|---|---|---|---|---|---|---|---|---|---|---|---|
| EGF | Y13 | — | — | Y37 | W50 | M21 | E24 | S25 | L26 | D27 | S28 |
| TGF | — | T20 | G19 | H18 | F17 | L24 | V25 | Q26 | E27 | D28 | K29 |

These results reinforce the hypothesis that the PCI does not inhibit cell and tumoral growth because of its protease inhibitory activity but due to a mechanism of interaction with growth factor receptors, probably through its globular core of the knotin type. If so, it would be a true antagonist of growth factors. Its great stability against proteases means that it is not destroyed when being internalized or when being recycled and thus, it may act again. The implication of the topology of the knotin type of the PCI offers great possibilities for the design of minor PCI variants or peptidemimetic or organomimetic molecules with better features of formulation, pharmacokinetic and pharmacodynamic, for their therapeutic use as antitumoral agents.

What is claimed is:

1. An isolated and/or purified polypeptide variant or fragment of a potato carboxypeptidase inhibitor consisting of the amino acid sequence shown in SEQ ID NO:2, wherein said variant polypeptide is PCIdelY37V38G39, that consists of residues 1–36 of SEQ ID NO:2 and said polypeptide fragment is GPYVG, corresponding to residues 35–39 of SEQ ID NO:2.

2. A pharmaceutical composition comprising, as an active ingredient, an effective amount of the polypeptide according to claim 1, and a pharmaceutically acceptable excipient or diluent.

3. A method of treating a pre-existing cancer or tumor in a patient in need of such treatment, comprising administering to said patient an effective amount of the polypeptide variant or fragment of claim 1.

4. A method of inhibiting growth or replication of pre-existing cancer or tumor cells comprising treating the pre-existing cancer or tumor cells with an effective amount of the polypeptide variant or fragment of claim 1.

5. A method of inhibiting growth or replication of pre-existing cancer or tumor cells comprising treating the pre-existing cancer or tumor cells with an effective amount of a polypeptide that comprises SEQ ID NO:2, or a polypeptide that comprises SEQ ID NO:2 having a substitution selected from the group consisting of: residue number 11 is Tyr, residue number 19 is Thr, residue number 20 is Gly, residue number 22 is Tyr or His, residue number 23 is Trp or Phe, residue number 28 is Met or Leu, residue number 29 is Gln or Val, residue number 30 is Ser or Gln, residue number 31 is Leu or Glu, residue number 32 Leu or Asp, residue number 33 is Ser or Lys and combinations thereof.

6. The method of claim 5 wherein the polypeptide has a sequence of SEQ ID NO:2.

7. The method of claim 5, wherein said polypeptide comprises at least one of the following structural determinants of antitumor activity: a globular core stabilized by disulphide bridges of the knotin type; or the C-terminal tail of said polypeptide shown as amino acid residues 35–39 of SEQ ID NO:2.

8. The method of claim 5 wherein the pre-existing cancer or tumor is a pancreatic adenocarcinoma or an insulinoma.

9. The method of claim 5, wherein said polypeptide antagonizes a growth factor of the pre-existing cancer or tumor cells.

10. The method of claim 9, wherein said growth factor has a globular core structure stabilized by disulphide bridges of the knotin type.

11. The method of claim 9, wherein said growth factor is an EGF growth factor or an TGF-alpha growth factor.

12. The method of claim 5 wherein the pre-existing cancer or tumor cells are present in a patient in need of said treatment, and said polypeptide is administered to said patient.

13. The method of claim 12 wherein said polypeptide antagonizes a growth factor of said cancer or tumor.

* * * * *

UNITED STATES PATENT AND TRADEMARK OFFICE
CERTIFICATE OF CORRECTION

PATENT NO.    : 6,379,959 B1
DATED         : April 30, 2002
INVENTOR(S)   : Llorens Duran, Rafael et al.

It is certified that error appears in the above-identified patent and that said Letters Patent is hereby corrected as shown below:

<u>Title page,</u>
Item [75], the name of the first inventor should be -- Rafael Llorens Duran --.
Item [73], the residence of the first assignee should be -- Barcelona -- and the residence of the second assingee should be -- Girona --

Signed and Sealed this

Thirteenth Day of May, 2003

JAMES E. ROGAN
*Director of the United States Patent and Trademark Office*

SEQUENCE LISTING

```
<160> NUMBER OF SEQ ID NOS: 6

<210> SEQ ID NO 1
<211> LENGTH: 123
<212> TYPE: DNA
<213> ORGANISM: Potato
<220> FEATURE:
<221> NAME/KEY: misc_feature
<222> LOCATION: (1)..(123)
<223> OTHER INFORMATION: Gene for isoform IIa of potato carboxypeptidase
      inhibitor

<400> SEQUENCE: 1
gaacagcacg cggatccgat ctgcaacaaa ccgtgcaaga ctcacgacga ctgctccggc        60
gcttggttct gccaagcttg ctggaacagc gctcgtacct gcggcccgta cgttggttaa       120
tag                                                                    123

<210> SEQ ID NO 2
<211> LENGTH: 39
<212> TYPE: PRT
<213> ORGANISM: Potato
<220> FEATURE:
<221> NAME/KEY: misc_feature
<222> LOCATION: (1)..(39)
```

```
<223> OTHER INFORMATION: Isoform IIa of the potato carboxypeptidase
      inhibitor

<400> SEQUENCE: 2

Glu Gln His Ala Asp Pro Ile Cys Asn Lys Pro Cys Lys Thr His Asp
1               5                   10                  15

Asp Cys Ser Gly Ala Trp Phe Cys Gln Ala Cys Trp Asn Ser Ala Arg
            20                  25                  30

Thr Cys Gly Pro Tyr Val Gly
            35

<210> SEQ ID NO 3
<211> LENGTH: 39
<212> TYPE: DNA
<213> ORGANISM: Artificial Sequence
<220> FEATURE:
<221> NAME/KEY: misc_feature
<222> LOCATION: (1)..(39)
<223> OTHER INFORMATION: PCR primer for deletion mutagenesis of PCI gene

<400> SEQUENCE: 3
cgaattccgg tcgacctatt acgggccgca ggtacgagc                                39

<210> SEQ ID NO 4
<211> LENGTH: 5
<212> TYPE: PRT
<213> ORGANISM: Artificial Sequence
<220> FEATURE:
<221> NAME/KEY: misc_feature
<222> LOCATION: (1)..(5)
<223> OTHER INFORMATION: C-terminal tail of PCI protein

<400> SEQUENCE: 4

Gly Pro Tyr Val Gly
1               5

<210> SEQ ID NO 5
<211> LENGTH: 20
<212> TYPE: DNA
<213> ORGANISM: Artificial Sequence
<220> FEATURE:
<221> NAME/KEY: misc_feature
<222> LOCATION: (1)..(20)
<223> OTHER INFORMATION: b2N-N901-920/5 primer

<400> SEQUENCE: 5
ttagctgtgc tcgcgctact                                                     20

<210> SEQ ID NO 6
<211> LENGTH: 19
<212> TYPE: DNA
<213> ORGANISM: Artificial Sequence
<220> FEATURE:
<221> NAME/KEY: misc_feature
<222> LOCATION: (1)..(19)
<223> OTHER INFORMATION: B2M-N3999-3980 primer

<400> SEQUENCE: 6
taaccacaac catgcttac                                                      19
```